United States Patent
Jiang et al.

(10) Patent No.: US 8,658,192 B2
(45) Date of Patent: *Feb. 25, 2014

(54) INTEGRATED ANTIMICROBIAL AND LOW FOULING MATERIALS

(75) Inventors: Shaoyi Jiang, Redmond, WA (US); Gang Cheng, Akron, OH (US); Luo Mi, Seattle, WA (US); Hong Xue, Pleasanton, CA (US); Yuting Li, Seattle, WA (US)

(73) Assignee: University of Washington, Seattle, WA (US)

( * ) Notice: Subject to any disclaimer, the term of this patent is extended or adjusted under 35 U.S.C. 154(b) by 240 days.

This patent is subject to a terminal disclaimer.

(21) Appl. No.: 12/904,341

(22) Filed: Oct. 14, 2010

(65) Prior Publication Data

US 2011/0195104 A1    Aug. 11, 2011

Related U.S. Application Data

(63) Continuation-in-part of application No. 12/780,194, filed on May 14, 2010, now abandoned, which is a continuation of application No. PCT/US2008/084099, filed on Nov. 19, 2008, application No. 12/904,341, which is a continuation-in-part of application No. 12/274,218, filed on Nov. 19, 2008, now Pat. No. 8,268,301.

(60) Provisional application No. 60/989,073, filed on Nov. 19, 2007, provisional application No. 61/253,000, filed on Oct. 19, 2009.

(51) Int. Cl.
| | |
|---|---|
| *A01N 25/00* | (2006.01) |
| *A61K 47/48* | (2006.01) |
| *A61K 31/74* | (2006.01) |
| *A01N 37/02* | (2006.01) |
| *A01P 1/00* | (2006.01) |
| *C08F 20/60* | (2006.01) |
| *C08F 8/36* | (2006.01) |
| *C08F 8/30* | (2006.01) |
| *C08F 299/00* | (2006.01) |
| *C08F 8/26* | (2006.01) |
| *C08G 63/91* | (2006.01) |

(52) U.S. Cl.
USPC .... 424/405; 424/78.17; 525/54.1; 525/292.2; 525/328.4; 526/292.2

(58) Field of Classification Search
None
See application file for complete search history.

(56) References Cited

U.S. PATENT DOCUMENTS 2,777,872 A * 1/1957 Shacklett .................. 560/169
3,671,502 A   6/1972 Samour
(Continued)

FOREIGN PATENT DOCUMENTS

DE   10 2006 004 111 A1   8/2007
EP         0 354 984 A2    2/1990
(Continued)

OTHER PUBLICATIONS

Cheng et al., A Switchable Biocompatible Polymer Surface with Self-Sterilizing and Nonfouling Capabilities, Angew. Chem. Int. Ed. (Oct. 7, 2008) 47, pp. 8831-8834, 4 pages.*

Zhang et al. (Nonfouling Behavior of Polycarboxybetaine-Grafted Surfaces: Structural and Environmental Effects, Biomacromolecules (Sep. 12, 2008), 9: 2686- 2692.), 7 pages.*

(Continued)

*Primary Examiner* — Ernst Arnold

(74) *Attorney, Agent, or Firm* — Christensen O'Connor Johnson Kindness PLLC

(57) ABSTRACT

Cationic polymers hydrolyzable to zwitterionic polymers, monomers for making the cationic polymers, surfaces that include the polymers, and methods for making and using the cationic polymers and surfaces. The cationic polymers include counterions and/or hydrolyzable groups that release active agents.

25 Claims, 46 Drawing Sheets
(12 of 46 Drawing Sheet(s) Filed in Color)

(56) References Cited

U.S. PATENT DOCUMENTS

| | | | |
|---|---|---|---|
| 4,075,183 | A | 2/1978 | Kawakami |
| 4,138,446 | A | 2/1979 | Kawakami |
| 4,415,388 | A | 11/1983 | Korpman |
| 4,493,926 | A | 1/1985 | Williams, Jr. |
| 4,985,023 | A | 1/1991 | Blank |
| 5,204,060 | A | 4/1993 | Allenmark |
| 5,714,360 | A | 2/1998 | Swan |
| 5,919,523 | A | 7/1999 | Sundberg |
| 5,986,042 | A | 11/1999 | Irizato |
| 6,361,768 | B1 | 3/2002 | Galleguillos |
| 6,486,333 | B1 | 11/2002 | Murayama |
| 6,897,263 | B2 | 5/2005 | Hell |
| 7,291,427 | B2 | 11/2007 | Kawamura |
| 7,306,625 | B1 | 12/2007 | Stratford |
| 7,335,248 | B2 | 2/2008 | Abou-Nemeh |
| 7,737,224 | B2 | 6/2010 | Willis |
| 2003/0108513 | A1 | 6/2003 | Hell |
| 2005/0058689 | A1 | 3/2005 | McDaniel |
| 2006/0240072 | A1 | 10/2006 | Chudzik |
| 2007/0042198 | A1 | 2/2007 | Schonemyr |

FOREIGN PATENT DOCUMENTS

| | | |
|---|---|---|
| EP | 0 419 654 A1 | 4/1991 |
| EP | 0 479 245 A2 | 4/1992 |
| JP | 63-234007 A | 9/1988 |
| JP | 63234007 A | 9/1988 |
| JP | 2003504476 A | 2/2003 |
| RU | 1780673 A1 | 12/1992 |
| WO | 00/39176 A1 | 7/2000 |
| WO | 01/04201 A1 | 1/2001 |
| WO | WO 2004049095 A2 * | 6/2004 |
| WO | 2004/058837 A2 | 7/2004 |
| WO | 2004/100666 A1 | 11/2004 |
| WO | 2007/068744 A1 | 6/2007 |
| WO | 2007/099239 A2 | 9/2007 |

OTHER PUBLICATIONS

Zhang et al. (Dual-Functional Biomimetic Materials: Nonfouling Poly(carboxybetaine) with Active Functional Groups for Protein Immobilization, Biomacromolecules (2006) 7, 3311-3315), 5 pages.*
"Betaine," Wikipedia, The Free Encyclopedia, <http://en.wikipedia.org/wiki/Betaine> [retrieved Jul. 31, 2011], 1 page.
"Bromide," Wikipedia, The Free Encyclopedia, <http://en.wikipedia.org/wiki/Bromide> [retrieved Jul. 27, 2011], 3 pages.
Chang, Y., et al., "Highly Protein-Resistant Coatings From Well-Defined Diblock Copolymers Containing Sulfobetaines," Langmuir 22(5):2222-2226, Feb. 2006.
Chen, S., et al., "Controlling Antibody Orientation on Charged Self-Assembled Monolayers," Langmuir 19(7):2859-2864, Apr. 2003.
Chen, S., et al., "Strong Resistance of Oligo(phosphorylcholine) Self-Assembled Monolayers to Protein Adsorption," Langmuir 22(6):2418-2421, Mar. 2006.
Chen, S., et al., "Strong Resistance of Phosphorylcholine Self-Assembled Monolayers to Protein Adsorption: Insights Into Nonfouling Properties of Zwitterionic Materials," Journal of the American Chemical Society 127(41):14473-14478, Oct. 2005.
Communication Pursuant to Article 94(3) EPC, mailed Oct. 19, 2010, issued in related European Application No. 08851463.3, filed Nov. 19, 2008, 4 pages.
Feng, W., et al., "Adsorption of Fibrinogen and Lysozyme on Silicon Grafted With Poly(2-methacryloyloxyethyl phosphorylcholine) Via Surface-Initiated Atom Transfer Radical Polymerization," Langmuir 21(13):5980-5987, Jun. 2005.
Feng., W., et al., "Atom-Transfer Radical Grafting Polymerization of 2-Methacryloyloxyethyl Phosphorylcholine From Silicon Wafer Surfaces," Journal of Polymer Science: Part A: Polymer Chemistry 42(12):2931-2942, Jun. 2004.
International Search Report and Written Opinion mailed May 4, 2009, issued in corresponding International Application No. PCT/US2008/084099, filed Nov. 19, 2008, 13 pages.

Jiang, Y., et al., "Blood Compatibility of Polyurethane Surface Grafted Copolymerization With Sulfobetaine Monomer," Colloids and Surfaces B: Biointerfaces 36(1):27-33, Jul. 2004.
Jun, Z., et al., "Surface Modification of Segmented Poly(ether urethane) by Grafting Sulfo Ammonium Zwitterionic Monomer to Improve Hemocompatibilities," Colloids and Surfaces B: Biointerfaces 28(1):1-9, Apr. 2003.
Li, L. et al., "Protein Adsorption on Alkanethiolate Self-Assembled Monolayers: Nanoscale Surface Structural and Chemical Effects," Langmuir 19(7):2974-2982, Apr. 2003.
Li, L. et al., "Protein Adsorption on Oligo(ethylene glycol)-Terminated Alkanethiolate Self-Assembled Monolayers: The Molecular Basis for Nonfouling Behavior," Journal of Physical Chemistry B 109(7):2934-2941, Feb. 2005.
Lowe, A.B., et al., "Well-Defined Sulfobetaine-Based Statistical Copolymers as Potential Antibioadherent Coatings," Journal of Biomedical Materials Research 52(1):88-94, Jul. 2000.
"Nail Infections," Health911, <http://www.health911.com/nail-infections> [retrieved Aug. 29, 2011], 3 pages.
West, S.L., et al., "The Biocompatibility of Crosslinkable Copolymer Coatings Containing Sulfobetaines and Phosphobetaines," Biomaterials 25:1195-1204, Apr. 2004.
Yuan, J., et al., "Chemical Graft Polymerization of Sulfobetaine Monomer on Polyurethane Surface for Reduction in Platelet Adhesion," Colloids and Surfaces B: Biointerfaces 39(1-2):87-94, Nov. 2004.
Yuan, J., et al., "Improvement of Blood Compatibility on Cellulose Membrane Surface by Grafting Betaines," Colloids and Surfaces B: Biointerfaces 30(1-2):147-155, Jul. 2003.
Yuan, J., "Platelet Adhesion Onto Segmented Polyurethane Surfaces Modified by Carboxybetaine," Journal of Biomaterial Science, Polymer Edition 14(12):1339-1349, Dec. 2003.
Yuan, Y., et al., "Grafting Sulfobetaine Monomer Onto Silicone Surface to Improve Haemocompatability," Polymer International 53(1):121-126, Jan. 2004.
Yuan, Y., et al. "Grafting Sulfobetaine Monomer Onto the Segmented Poly(ether-urethane) Surface to Improve Hemocompatability," Journal of Biomaterials Science, Polymer Edition 13(10):1081-1092, Oct. 2002.
Yuan, Y., et al., "Polyurethane Vascular Catheter Surface Grafted With Zwitterionic Sulfobetaine Monomer Activated by Ozone," Colloids and Surfaces B: Biointerfaces 35(1):1-5, May 2004.
Yuan, Y., et al., "Surface Modification of SPEU Films by Ozone Induced Graft Copolymerization to Improve Hemocompatibility," Colloids and Surfaces B: Biointerfaces 29(4):247-256, Jun. 2003.
Zhang, J., et al., "Chemical Modification of Cellulose Membranes With Sulfo Ammonium Zwitterionic Vinyl Monomer to Improve Hemocompatibility," Colloids and Surfaces B: Biointerfaces 30(3):249-257, Jul. 2003.
Zhang, Z., et al., "The Hydrolysis of Cationic Polycarboxybetaine Esters to Zwitterionic Polycarboxybetaines With Controlled Properties," Biomaterials 29(36):4719-4725, Dec. 2008.
Zhang, Z., et al., "Superflow Fouling Sulfobetaine and Carboxybetaine Polymers on Glass Slides," Langmuir 22 (24):10072-10077, Nov. 2006.
Zhang, Z., "Surface Grafted Sulfobetaine Polymers Via Atom Transfer Radical Polymerization as Superlow Fouling Coatings," Journal of Physical Chemistry B 110(22):10799-10804, Jun. 2006.
Zheng, J., "Molecular Simulation Study of Water Interactions With Oligo (Ethylene Glycol)-Terminated Alkanethiol Self-Assembled Monolayers," Langmuir 20(20):8931-8938, Sep. 2004.
Zheng, J., "Strong Repulsive Forces Between Protein and Oligo (Ethylene Glycol) Self-Assembled Monolayers: A Molecular Simulation Study," Biophysical Journal 89(1):158-166, Jul. 2005.
Zhou, J., et al., "Platelet Adhesion and Protein Adsorption on Silicone Rubber Surface by Ozone-Induced Grafted Polymerization With Carbonxybetaine Monomer," Colloids and Surfaces B: Biointerfaces 41(1):55-62, Mar. 2005.
Official Action mailed Apr. 15, 2013, issued in corresponding Japanese Application No. 2010-534289, filed Nov. 19, 2008, 5 pages.

* cited by examiner

CBAA-1-ester

CBAA-3-ester

CBAA-5-ester pCBMA-1 C2 pCBMA-1 C2 pC8NMA pC8NMA pCBMA-2 pCBMA-2

CBMA-1 C2 SA pCBMA-2 pCBMA-1 C2 SA

INTEGRATED ANTIMICROBIAL AND LOW FOULING MATERIALS

CROSS-REFERENCES TO RELATED APPLICATIONS

This application claims the benefit of U.S. Provisional Application No. 61/253,000, filed Oct. 19, 2009; is a continuation-in-part of U.S. patent application Ser. No. 12/780,194, filed May 14, 2010, which is a continuation of International Patent Application No. PCT/US2008/084099, filed Nov. 19, 2008, which claims the benefit of U.S. Provisional Application No. 60/989,073, filed Nov. 19, 2007; and is a continuation-in-part of U.S. patent application Ser. No. 12/274,218, filed Nov. 19, 2008, which claims the benefit of U.S. Provisional Application No. 60/989,073, filed Nov. 19, 2007. Each application is incorporated herein by reference in its entirety.

STATEMENT OF GOVERNMENT LICENSE RIGHTS

This invention was made with Government support under Grant Nos. N00014-04-1-0409 and N00014-07-1-1036 awarded by the Office of Naval Research, Grant Nos. HDTRA1-07-1-0033 and AB06BAS759 awarded by the Defense Threat Reduction Agency, and Grant No. DMR-0705907 awarded by the National Science Foundation. The Government has certain rights in the invention.

BACKGROUND OF THE INVENTION

Microbial adhesion onto biomaterial implants and the subsequent formation of biofilms are one of the major reasons for failure of implantable biomedical devices, and about 45% of nosocomial infections are caused by biomaterial-associated infections. These nosocomial microbial infections associated with implanted biomedical devices such as implantable sensors, catheters and artificial prosthetics, typically lead to removal of the devices due to the lack of a suitable treatment, and increase the duration of hospital stays and hospitalization costs. Currently, there is a constant demand for new materials capable of preventing the colonization of microorganisms onto surfaces of implantable materials.

To reduce bacterial attachment and colonization, one method is to coat surfaces with nonfouling materials such as poly(ethylene glycol) (PEG) derivatives or zwitterionic polymers. Surfaces coated with 2-methacryloyloxyethyl phosphorylcholine (MPC) reduce the attachment of bacteria by 90%. Recent studies demonstrated that zwitterionic poly(sulfobetaine methacrylate) (pSBMA) and poly(2-carboxy-N,N-dimethyl-N-(2'-(methacryloyloxy)ethyl)ethanaminium) (pCBMA-2) efficiently reduced the colonization of *Pseudomonas aeruginosa* and *Staphylococcus epidermidis*. These materials are also proved to be highly resistant to protein adsorption from 100% serum and blood plasma. Although these non-fouling materials can significantly reduce the initial attachment and delay the colonization of microbes on the surfaces, they cannot kill or inhibit the growth of pathogenic bacteria cells once bacteria are attached to surfaces.

During implantation surgery, there is a great possibility of introducing pathogenic microbes into the patient, thereby causing the failure of implantation devices. The antimicrobial strategy is another method for preventing bacterial colonization on surfaces. Quaternary ammonium compounds (QACs) are extensively used as antimicrobial agents due to their broad antimicrobial properties. These QACs, when covalently linked to material surfaces to make the surface permanent microbiocidal, are able to efficiently kill both bacterial cells and fungal cells. However, permanent QACs coatings cannot fulfill the requirement of implantable biomaterials for non-fouling and biocompatibility. The inherent drawback of permanent QAC coatings is that they generate a fouling surface that triggers the immune response and chronic inflammation.

Despite the advances noted above, a need exists for a multifunctional polymers and that combines the advantages of non-fouling and cationic antimicrobial materials, while overcoming their respective disadvantages. The present invention seeks to fulfill this need and provides further related advantages.

SUMMARY OF THE INVENTION

The present invention provides cationic polymers that are hydrolyzable to zwitterionic polymers, cationic monomers that are polymerizable to provide the cationic polymers, surfaces coated with the cationic polymers, methods for applying the cationic polymers to surfaces, and methods for making the cationic polymers and the cationic monomers.

In one aspect, the invention provides cationic polymers that release therapeutic agents and that are hydrolyzable to zwitterionic polymers.

In one embodiment, the cationic polymer comprises:
(a) polymer backbone;
(b) a plurality of cationic centers, each cationic center covalently coupled to the polymer backbone by a first linker;
(c) a counter ion associated with each cationic center; and
(d) a hydrolyzable group covalently coupled to each cationic center through a second linker, wherein the hydrolyzable group is hydrolyzable to an anionic center to provide a zwitterionic polymer having the anionic center covalently coupled to the cationic center through the second linker, wherein at least a portion of the counter ions are antimicrobial agents, antibacterial agents, or antifungal agents, and/or wherein at least a portion of the hydrolyzable groups release an antimicrobial agent, an antibacterial agent, or an antifungal agent.

In one embodiment, the cationic polymer has the formula:

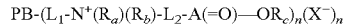

$$\text{PB-}(L_1\text{-N}^+(R_a)(R_b)\text{-}L_2\text{-A}(=O)\text{---}OR_c)_n(X^-)_n$$

wherein PB is the polymer backbone having n pendant groups $L_1$-$N^+(R_a)(R_b)$-$L_2$-$A(=O)$—$OR_c$); $N^+$ is the cationic center; $R_a$ and $R_b$ are independently selected from hydrogen, alkyl, and aryl, or taken together with $N^+$ form a cationic center; $A(=O)$—$OR_c$ is the hydrolyzable group, wherein A is selected from the group consisting of C, S, SO, P, or PO, and $R_c$ is an alkyl, aryl, acyl, or silyl group that may be further substituted with one or more substituents; $L_1$ is a linker that covalently couples the cationic center to the polymer backbone; $L_2$ is a linker that covalently couples the cationic center to the hydrolyzable group; $X^-$ is the counter ion associated with the cationic center; and n is an integer from about 10 to about 10,000; wherein at least a portion of the counter ions are antimicrobial agents, antibacterial agents, or antifungal agents, and/or wherein at least a portion of the hydrolyzable groups release an antimicrobial agent, an antibacterial agent, or an antifungal agent.

In one embodiment, the cationic polymer comprises:
(a) polymer backbone;
(b) a plurality of cationic repeating units, each repeating unit comprising a cationic centers, each cationic center covalently coupled to the polymer backbone by a first linker;
(c) a counter ion associated with each cationic center; and (d) a plurality of repeating units, each repeating unit comprising a hydrolyzable group covalently coupled to the polymer backbone by a second linker, wherein the hydrolyzable group is hydrolyzable to an anionic center to provide a zwitterionic polymer, each anionic center covalently coupled to the polymer backbone by the second linker, wherein at least a portion of the counter ions are antimicrobial agents, antibacterial agents, or antifungal agents, and/or wherein at least a portion of the hydrolyzable groups release an antimicrobial agent, an antibacterial agent, or an antifungal agent.

In one embodiment, the cationic polymer has the formula:

PB-[L$_1$-N$^+$(R$_a$)(R$_b$)(R$_e$)]$_n$[L$_2$-A(=O)—OR$_c$]$_p$(X$^-$)$_n$ wherein PB is a polymer backbone having n pendant L$_1$-N$^+$(R$_a$)(R$_b$)(R$_e$) groups and p pendant L$_2$-A(=O)—OR$_c$ groups; R$_a$, R$_b$, and R$_e$ are independently selected from alkyl and aryl, or taken together with the nitrogen to which they are attached form a cationic center; A(=O)—OR$_c$ is a hydrolyzable group, wherein A is selected from the group consisting of C, S, SO, P, or PO, and R$_c$ is an alkyl, aryl, acyl, or silyl group that may be further substituted with one or more substituents; L$_1$ is a linker that covalently couples the cationic center to the polymer backbone; L$_2$ is a linker that covalently couples the hydrolyzable group to the polymer backbone; X$^-$ is the counter ion associated with the cationic center; n is an integer from 1 to about 1,000; and p is an integer from 1 to about 1,000; wherein at least a portion of the counter ions are antimicrobial agents, antibacterial agents, or antifungal agents, and/or wherein at least a portion of the hydrolyzable groups release an antimicrobial agent, an antibacterial agent, or an antifungal agent. In one embodiment, the cationic copolymer is crosslinked.

In certain embodiments of the cationic polymers, a portion of the counter ions are antimicrobial agents.

In certain embodiments of the cationic polymers, a portion of the hydrolyzable groups release an antimicrobial agent.

In certain embodiments, the polymer is crosslinked.

In certain embodiments, the polymer is a hydrogel.

In another aspect, the invention provides surfaces that are treated with, coated with, modified by, or otherwise incorporates one or more polymers or hydrogels of the invention. In certain embodiments, the invention provides a surface of a substrate that has been treated with, coated with, modified by, or otherwise incorporates one or more polymers or hydrogels of the invention.

Methods for applying, coating, modifying, or otherwise incorporating one or more polymers or hydrogels of the invention onto a surface of a substrate are also provided. The polymers or hydrogels can be directly applied to a surface. Alternatively, in other embodiments, the surfaces can be substrates onto which the polymers or hydrogels are made by conventional polymerization techniques involving suitable monomers.

DESCRIPTION OF THE DRAWINGS

The patent or application file contains at least one drawing executed in color. Copies of this patent or patent application publication with color drawing(s) will be provided by the Office upon request and payment of the necessary fee.

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE INVENTION

Figure 1:
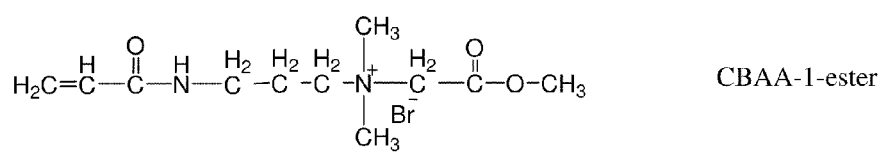
FIG. 1 illustrates the structures of three representative cationic monomers useful for making cationic polymers of the invention: three acrylamide monomers with different carboxybetaine ester groups; CBAA-1-ester, CBAA-3-ester, and CBAA-5-ester.
Figure 1:
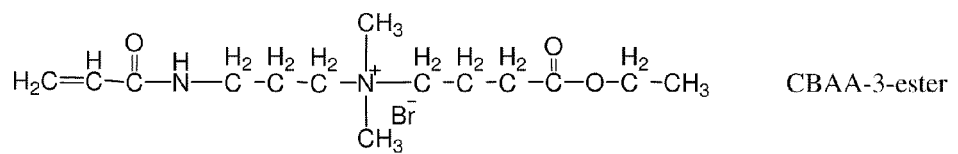
Figure 1:
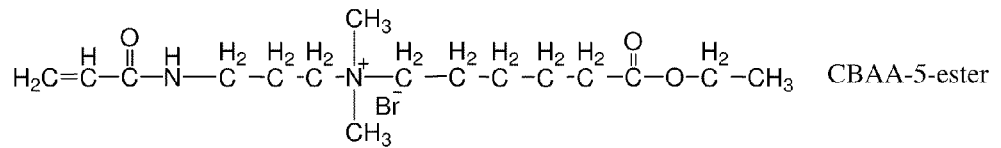

The invention provides polymers and hydrogels, materials made from the polymers and hydrogels, and methods for making and using the polymers, hydrogels, and materials made from the polymers and hydrogels.

In one aspect, the invention provides a switchable polymer surface that integrates antimicrobial and nonfouling properties and that is biocompatible. In certain embodiments, the invention provides polymers and hydrogels that are antimicrobial by virtue of their release of antimicrobial agents, and become non-fouling by virtue of their hydrolysis to provide zwitterionic polymers and hydrogels.

The polymers and hydrogels of the invention are cationic polymers having cationic centers and hydrolyzable groups. In one embodiment, the counter ion associated with the polymer's cationic center is an antimicrobial agent. In this embodiment, release of the counter ion provides antimicrobial activity. In one embodiment, the hydrolyzable group releases an antimicrobial agent. In one embodiment, the counter ion associated with the polymer's cationic center is an antimicrobial agent and the hydrolyzable group releases an antimicrobial agent.

Representative antimicrobial agents include salicylic acid, benzoic acid, lactic acid, cephalosporin, penicillin, and other antimicrobial agents known in the art. The antimicrobial agents can be used an counter ions or hydrolyzable groups.

In one embodiment, in addition to antimicrobial agents, therapeutic drugs can be used as counter ions or hydrolyzable groups. In these embodiments, the therapeutic drug is released from the polymer.

In addition to their antimicrobial activities, the cationic polymers and hydrogels are hydrolyzable to zwitterionic polymers thereby rendering surfaces to which the polymers and hydrogels are associated non-fouling.

In one aspect of the invention, cationic polymers are provided. The cationic polymers of the invention include hydrolyzable groups that can be hydrolyzed to provide zwitterionic polymers. Zwitterionic polymers are polymers having a balance of positive and negative charge. Zwitterionic polymers can be highly resistant to protein adsorption and bacterial adhesion. Due to their biomimetic nature, zwitterionic polymers, such as phosphobetaine, sulfobetaine, and carboxybetaine polymers, exhibit high biocompatibility.

The hydrogels of the invention include the cationic polymers. In certain embodiments, the hydrogel is a crosslinked hydrogel.

Controlled Hydrolysis. The variation of the structural features of the cationic polymers allows for their controlled hydrolysis and the control of the biological, chemical, and mechanical properties. The rate of hydrolysis can be significantly affected by and controlled by the selection of the nature of the hydrolyzable group (e.g., for esters, —OR).

As described below, in certain embodiments, the cationic polymers of the invention advantageously release functional groups on hydrolysis. For example, for cationic esters of the invention, hydrolysis ester releases an —OR group. In these embodiments, the released group can be a therapeutic agent (e.g., an antimicrobial agent, an antibacterial agent, an antifungal agent). Similarly, in certain embodiments, the cationic polymers can release their counter ions (V), which can also be therapeutic agents (e.g., an antimicrobial agent, an antibacterial agent, an antifungal agent).

For applications as antimicrobial agents, antimicrobial cationic polymers can be converted to zwitterionic polymers, leaving no toxic residues in the environment or no killed microbes on a surface.

It will be appreciated that the hydrolyzable group can be cleaved not only by hydrolysis, but also by cleavage (e.g., degradation or erosion) that occurs by other means. The cationic polymers can be converted to their corresponding zwitterionic polymers by environmental changes due to enzymatic catalysis, redox, heat, light, ionic strength, pH, and hydrolysis, among others.

Representative cationic polymers of the invention and their corresponding zwitterionic polymer counterparts are described below.

Cationic Polymers

The cationic polymers of the invention include hydrolyzable groups that, when hydrolyzed, provide anionic groups that render the polymer zwitterionic. In each polymer, the number of hydrolyzable groups is substantially equal to the number of cationic groups such that, when the hydrolyzable groups are hydrolyzed, in the resulting polymer is zwitterionic. As used herein, the term "zwitterionic polymer" refers to a polymer having substantially equal numbers of cationic groups and anionic groups.

In one embodiment, the cationic polymer is a homopolymer. In another embodiment, the cationic polymer is a copolymer.

Cationic Homopolymers

Representative cationic homopolymers of the invention have formula (I):

$$PB\text{-}(L_1\text{-}N^+(R_a)(R_b)\text{-}L_2\text{-}A(=O)\text{---}OR_c)_n(X^-)_n \qquad (I)$$

wherein PB is the polymer backbone having n pendant groups (i.e., $L_1$-$N^+$($R_a$)($R_b$)-$L_2$-$A$(=O)—$OR_c$);

$N^+$ is the cationic center; $R_a$ and $R_b$ are independently selected from hydrogen, alkyl, and aryl groups, or taken together with $N^+$ form a cationic center;

$A(=O)$—$OR_c$ is the hydrolyzable group, wherein A is C, S, SO, P, or PO, and $R_c$ is an alkyl, aryl, acyl, or silyl group that may be further substituted with one or more substituents;

$L_1$ is a linker that covalently couples the cationic center to the polymer backbone;

$L_2$ is a linker that covalently couples the cationic center to the hydrolyzable group;

$X^-$ is the counter ion associated with the cationic center; and n is from about 10 to about 10,000, wherein at least a portion of the counter ions are antimicrobial agents, antibacterial agents, or antifungal agents, and/or wherein at least a portion of the hydrolyzable groups release an antimicrobial agent, an antibacterial agent, or an antifungal agent.

The average molecular weight of the polymers of formula (I) is from about 1 kDa to about 1,000 kDa.

Hydrolysis of the cationic polymer of formula (I) provides zwitterionic polymer having formula (II):

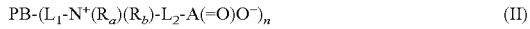
$$PB\text{-}(L_1\text{-}N^+(R_a)(R_b)\text{-}L_2\text{-}A(=O)O^-)_n \qquad (II)$$

wherein PB, $L_1$, $N^+$, $R_a$, $R_b$, $L_2$, A, and n are as described above, and $A(=O)O^-$ is the anionic group.

In this embodiment, the polymer of formula (I) includes n pendant groups and can be prepared by polymerization of monomers having formula (III):

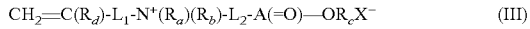
$$CH_2=C(R_d)\text{-}L_1\text{-}N^+(R_a)(R_b)\text{-}L_2\text{-}A(=O)\text{---}OR_cX^- \qquad (III)$$

wherein $L_1$, $N^+$, $R_a$, $R_b$, $A(=O)OR_c$, and $L_2$, and $X^-$ are as described above, $R_d$ is selected from hydrogen, fluorine, trifluoromethyl, C1-C6 alkyl, and C6-C12 aryl groups.

Cationic Copolymers

As noted above, in one embodiment, the cationic polymers of the invention are cationic copolymers. Representative cationic copolymers of the invention provide polyampholytes on hydrolysis. As used herein, the term "polyampholyte" refers to a copolymer having a polymer backbone, a plurality of positively charged repeating units, and a plurality of negatively charged repeating units (i.e., provided by hydrolysis of the polymer's hydrolyzable groups to provide anionic centers, thereby rendering the cationic polymer a zwitterionic polymer). In the practice of the invention, these copolymers may be prepared by polymerization of an ion-pair comonomer.

In one embodiment, the polyampholyte is substantially electronically neutral. As used herein, the term "substantially electronically neutral" refers to a copolymer that imparts advantageous nonfouling properties to a surface to which the copolymer is attached. In one embodiment, a substantially electronically neutral copolymer is a copolymer having a net charge of substantially zero (i.e., a copolymer about the same number of positively charged repeating units and negatively charged repeating units). In one embodiment, the ratio of the number of positively charged repeating units to the number of the negatively charged repeating units is from about 1:1.1 to about 1:0.5. In one embodiment, the ratio of the number of positively charged repeating units to the number of the negatively charged repeating units is from about 1:1.1 to about 1:0.7. In one embodiment, the ratio of the number of positively charged repeating units to the number of the negatively charged repeating units is from about 1:1.1 to about 1:0.9.

In one embodiment, the cationic polymer comprises:
(a) polymer backbone;
(b) a plurality of cationic repeating units, each repeating unit comprising a cationic centers, each cationic center covalently coupled to the polymer backbone by a first linker;
(c) a counter ion associated with each cationic center; and
(d) a plurality of repeating units, each repeating unit comprising a hydrolyzable group covalently coupled to the polymer backbone by a second linker, wherein the hydrolyzable group is hydrolyzable to an anionic center to provide a zwitterionic polymer, each anionic center covalently coupled to the polymer backbone by the second linker, wherein at least a portion of the counter ions are antimicrobial agents, antibacterial agents, or antifungal agents, and/or wherein at least a portion of the hydrolyzable groups release an antimicrobial agent, an antibacterial agent, or an antifungal agent.

Representative cationic copolymers of the invention have formula (IV):

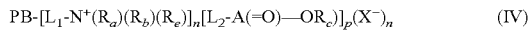

wherein
PB is the polymer backbone having n pendant $L_1$-$N^+(R_a)(R_b)(R_e)$ groups and p pendant $L_2$-$A(=O)$—$OR_c$, groups;
$R_a$, $R_b$, and $R_e$ are independently selected from alkyl and aryl, or taken together with the nitrogen to which they are attached form a cationic center;
$A(=O)$—$OR_c$ is the hydrolyzable group, wherein A is C, S, SO, P, or PO, and $R_c$ is an alkyl, aryl, acyl, or silyl group that may be further substituted with one or more substituents;
$L_1$ is a linker that covalently couples the cationic center $[N^+(R_a)(R_b)(R_e)]$ to the polymer backbone;
$L_2$ is a linker that covalently couples the anionic center $[A(=O)$—$OR_c]$ to the polymer backbone;
$X^-$ is the counter ion associated with the cationic center;
n is an integer from 1 to about 1,000;
p is an integer from 1 to about 1,000; and
m is an integer from 1 to 20,
wherein at least a portion of the counter ions are antimicrobial agents, antibacterial agents, or antifungal agents, and/or
wherein at least a portion of the hydrolyzable groups release an antimicrobial agent, an antibacterial agent, or an antifungal agent.

In the formula (IV), $R_e$ is as described above for $R_a$ and $R_b$.
In formula (IV), PB, DHP, $L_1$, $L_2$, $L_3$, $N^+$, $R_a$, $R_b$, A(=O)$OR_c$, and $X^-$ are as described above.

As noted above, in certain embodiments, the copolymers are substantially electronically neutral. In one embodiment, n is about equal to p. In one embodiment, n=p.

Hydrolysis of the cationic polymer of formula (IV) provides zwitterionic polymer having formula (V):

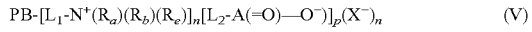

wherein PB, $L_1$, $N^+$, $R_a$, $R_b$, $R_e$, $L_2$, A, $X^-$, n, and p are as described above, and $A(=O)O^-$ is the anionic group.

The cationic copolymers of the invention are prepared by polymerization of ion-pair comonomers. A representative ion-pair comonomer useful in the invention has formulas (VI) and (VII):

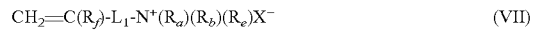

wherein $L_1$, $L_2$, $N^+$, $R_a$, $R_b$, $R_e$, A(=O)$OR_c$, and $X^-$ are as described above, and $R_d$ and $R_f$ are independently selected from the group consisting of hydrogen, fluorine, trifluoromethyl, and C1-C6 alkyl.

The following is a description of the polymers and monomers of formulas (I)-(VII) described above.

In the above formulas, PB is the polymer backbone. Representative polymer backbones include vinyl backbones (i.e., —C(R')(R")—C(R''')(R'''')—, where R', R", R''', and R'''' are independently selected from hydrogen, alkyl, and aryl) derived from vinyl monomers (e.g., acrylate, methacrylate, acrylamide, methacrylamide, styrene). Other suitable backbones include polymer backbones that provide for pendant cationic groups that include hydrolyzable groups that can be converted to zwitterionic groups, and backbones that include cationic groups and that provide for pendant hydrolyzable groups that can be converted to zwitterionic groups. Other representative polymer backbones include peptide (polypeptide), urethane (polyurethane), and epoxy backbones.

Similarly, in the above formulas, $CH_2=C(R_d/R_f)$— is the polymerizable group. It will be appreciated that other polymerizable groups, including those noted above, can be used to provide the monomers and polymers of the invention.

In the above formulas, $N^+$ is the cationic center. In certain embodiments, the cationic center is a quaternary ammonium (N bonded to $L_1$; $R_a$, $R_b$, and $L_2$). In addition to ammonium, other useful cationic centers ($R_a$ and $R_b$ taken together with N) include imidazolium, triazaolium, pyridinium, morpholinium, oxazolidinium, pyrazinium, pyridazinium, pyrimidinium, piperazinium, and pyrrolidinium.

$R_a$, $R_b$, and $R_e$ are independently selected from hydrogen, alkyl, and aryl groups. Representative alkyl groups include C1-C10 straight chain and branched alkyl groups. In certain embodiments, the alkyl group is further substituted with one of more substituents including, for example, an aryl group (e.g., —$CH_2C_6H_5$, benzyl). In one embodiment, $R_a$ and $R_b$ are methyl. In one embodiment, $R_a$, $R_b$, and $R_e$ are methyl. Representative aryl groups include C6-C12 aryl groups including, for example, phenyl. For certain embodiments of the above formulas, $R_a$ and $R_b$ (and $R_e$) are taken together with $N^+$ form the cationic center.

$L_1$ is a linker that covalently couples the cationic center to the polymer backbone. In certain embodiments, $L_1$ includes a functional group (e.g., ester or amide) that couples the remainder of $L_1$ to the polymer backbone (or polymerizable moiety for the monomers). In addition to the functional group, $L_1$ can include an C1-C20 alkylene chain. Representative $L_1$ groups include —C(=O)O—$(CH_2)_n$— and —C(=O)NH—$(CH_2)_n$—, where n is 1-20 (e.g., 3).

For the cationic homopolymers, $L_2$ is a linker that covalently couples the cationic center to the hydrolyzable group (or anionic group for the zwitterionic polymer). $L_2$ can be a C1-C20 alkylene chain. Representative $L_2$ groups include —$(CH_2)_n$—, where n is 1-20 (e.g., 1, 3, or 5).

For the cationic copolymers, $L_2$ is a linker that covalently couples the polymer backbone to the hydrolyzable group (or anionic group for the zwitterionic polymer). $L_2$ can be a C1-C20 alkylene chain. Representative $L_2$ groups include —$(CH_2)_n$—, where n is 1-20 (e.g., 1, 3, or 5).

The hydrophobicity and the rate of hydrolysis of the cationic polymers of formula (I) can be controlled by $L_1$ and/or $L_2$. The greater the hydrophobicity of $L_1$ or $L_2$, the slower the hydrolysis of the hydrolyzable group and the conversion of the cationic polymer to the zwitterionic polymer.

$A(=O)$—$OR_c$ is the hydrolyzable group. The hydrolyzable group can be an ester, such as a carboxylic acid ester (A is C), a sulfinic acid ester (A is S), a sulfonic acid ester (A is SO), a phosphinic acid ester (A is P), or a phosphonic acid ester (A is PO). The hydrolyzable group can also be an anhydride. $R_e$ is an alkyl, aryl, acyl, or silyl group that may be further substituted with one or more substituents.

Representative alkyl groups include C1-C30 straight chain and branched alkyl groups. In certain embodiments, the alkyl group is further substituted with one of more substituents including, for example, an aryl group (e.g., —$CH_2C_6H_5$, benzyl). In certain embodiments, $R_c$ is a C1-C20 straight chain alkyl group. In one embodiment, $R_c$ is methyl. In another embodiment, $R_c$ is ethyl. In one embodiment, $R_c$ is a C3-C20 alkyl. In one embodiment, $R_c$ is a C4-C20 alkyl. In one embodiment, $R_c$ is a C5-C20 alkyl. In one embodiment, $R_c$ is a C6-C20 alkyl. In one embodiment, $R_c$ is a C8-C20 alkyl. In one embodiment, $R_c$ is a C10-C20 alkyl. For applications where relatively slow hydrolysis is desired, $R_c$ is a C4-C20 n-alkyl group or a C4-C30 n-alkyl group.

Representative aryl groups include C6-C12 aryl groups including, for example, phenyl including substituted phenyl groups (e.g., benzoic acid).

Representative acyl groups (—C(=O)$R_e$) include acyl groups where $R_e$ is C1-C20 alkyl or C6-C12 aryl.

Representative silyl groups (—$SiR_3$) include silyl groups where R is C1-C20 alkyl or C6-C12 aryl.

In certain embodiments of the invention, the hydrolysis product $R_cO^-$ (or $R_cOH$) is a therapeutic agent (e.g., an antimicrobial agent, such as salicylic acid (2-hydroxybenzoic acid), benzoate, lactate, and the anion form of antibiotic and antifungal drugs).

In certain other embodiments, the hydrolysis product $R_cO^-$ (or $R_cOH$) is a lactate, glycolate, or amino acid.

The rate of hydrolysis of the cationic polymers of formula (I) can also be controlled by $R_c$. The slower the hydrolysis of the hydrolyzable group due to, for example, steric and/or kinetic effects due to $R_c$, the slower the conversion of the cationic polymer to the zwitterionic polymer.

$X^-$ is the counter ion associated with the cationic center. The counter ion can be the counter ion that results from the synthesis of the cationic polymers or the monomers (e.g., $Cl^-$, $Br^-$, $I^-$). The counter ion that is initially produced from the synthesis of the cationic center can also be exchanged with other suitable counter ions to provide polymers having controllable hydrolysis properties and other biological properties.

The rate of hydrolysis of the cationic polymers can be controlled by the counter ion. The more hydrophobic the counter ion, the slower the hydrolysis of the hydrolyzable group and the slower the conversion of the cationic polymer to the zwitterionic polymer. Representative hydrophobic counter ions include carboxylates, such as benzoic acid and fatty acid anions (e.g., $CH_3(CH_2)_nCO_2^-$ where n=1-19); alkyl sulfonates (e.g., $CH_3(CH_2)_nSO_3^-$ where n=1-19); salicylate; lactate; bis(trifluoromethylsulfonyl)amide anion ($N^-(SO_2CF_3)_2$); and derivatives thereof. Other counter ions also can be chosen from chloride, bromide, iodide, sulfate; nitrate; perchlorate ($ClO_4$); tetrafluoroborate ($BF_4$); hexafluorophosphate ($PF_6$); trifluoromethylsulfonate ($SO_3CF_3$); and derivatives thereof.

Other suitable counter ions include hydrophobic counter ions and counter ions having therapeutic activity (e.g., an antimicrobial agent, such as salicylic acid (2-hydroxybenzoic acid), benzoate, lactate, and the anion form of antibiotic and antifungal drugs).

For the monomers, $R_d$ is selected from hydrogen, fluoride, trifluoromethyl, and C1-C6 alkyl (e.g., methyl, ethyl, propyl, butyl). In one embodiment, $R_d$ is hydrogen. In one embodiment, $R_d$ is methyl. In another embodiment, $R_d$ is ethyl.

The variation of the structural features of the cationic polymers allows for their controlled hydrolysis and the control of the biological, chemical, and mechanical properties. The structural features of the cationic polymers noted above that can be varied to achieve the desired controlled hydrolysis of the polymer include $L_1$, $L_2$, $R_a$, $R_b$, A, $R_c$, and $X^-$. In general, the more hydrophobic the polymer or the noted structural feature, the slower the hydrolysis of the cationic polymer to the zwitterionic polymer.

Homopolymers, Random Copolymers, Block Copolymers.

The cationic polymer of the invention include homopolymers, random copolymers, and block copolymers.

In one embodiment, the invention provides cationic homopolymers, such as defined by formula (I), prepared by polymerizing a cationic monomer, such as defined by formula (III). It will be appreciated that the advantageous properties associated with cationic polymers of the invention including those polymers defined by formula (I) can be imparted to other polymeric materials.

In one embodiment, the invention provides random copolymers prepared by copolymerizing two different cationic monomers of formula (III).

In another embodiment, the invention provides random copolymers that include cationic repeating units prepared by copolymerizing one or more cationic monomers of the invention defined by formula (III) with one or more other monomers (e.g., hydrophobic monomers, anionic monomers, or zwitterionic monomers, such as phosphorylbetaine, sulfobetaine, or carboxybetaine monomers).

In one embodiment, the invention provides block copolymers having one or more blocks comprising cationic repeating units and one or more other blocks. In this embodiment, the one or more blocks that include cationic repeating units include only cationic repeating units (e.g., homo- or copolymer prepared from cationic monomers of formula (III)). Alternatively, the one or more blocks that include cationic repeating units include cationic repeating units and other repeating units (e.g., hydrophobic, anionic, zwitterionic repeating units).

Other Suitable Polymers

The invention also provides the following polymers.

In one embodiment, the cationic polymer has the following structure:

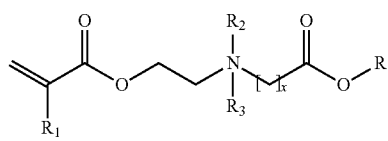

$R_1$=—H, —$CH_3$, —$C_2H_5$
$R_2$=no atom, —H, —$CH_3$, —$C_2H_5$
$R_3$=—H, —$CH_3$, —$C_2H_5$
x=1-8.
R=any alkyl chain, aromatic or lactate or glycolate $R_4$=—H, —CH$_3$, —C$_2$H$_5$
Y=1-10
Z=0-22
or C(=O)R'
R'=any alkyl chain or aromatic group.
In another embodiment, the cationic polymer has the following structure:

n>5
x=1-5
y=1-5
$R_1$=H, or alkyl chain
$R_2$=no atom, H, or alkyl chain
$R_3$=alkyl chain.
In another embodiment, the invention provides a polymer having the following structure:

$R_1$ is any alkyl chain
$R_3$ is any alkyl chain
$R_2$, $R_4$ is any alkyl chain
x=1-18
y=1-18
n>3.
In another embodiment, the invention provides a polymer having the following structure:

R is alkyl chain
x=1-18
y=1-18
n>3.
In another embodiment, the invention provides a polymer having the following structure:

R=any alkyl chain
x=0-11
n>3.
In another embodiment, the invention provides a polymer having the following structure:
n>3
x=1-10
R=any alkyl chain, aromatic or lactate or glycolate.

$R_4$=—H, —CH$_3$, —C$_2$H$_5$
y=1-10
z=0-22
or C(=O)R'
R'=any alkyl chain, aromatic group.
In another embodiment, the invention provides polymers having the following structure:

n>3
x=1-6
y=0-6
R=any alkyl chain, aromatic or lactate or glycolate)

$R_4$=—H, —CH$_3$, —C$_2$H$_5$
y=1-10
z=0-22
or C(=O)R'
R'=any alkyl chain, aromatic group.

In another embodiment, the invention provides a polymer having the following structure:

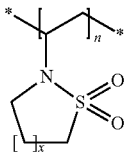

n>5
x=0-5.

In another embodiment, the invention provides a polymer having the following structure:

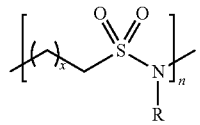

x=0-17
n>5
R=H or alkyl chain.

In another embodiment, the invention provides a polymer having the following structure:

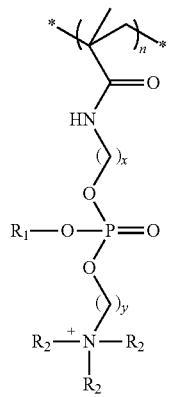

n>5
$R_2$=H or any alkyl chain, e.g., methyl
x, y=1-6
$R_1$=any alkyl chain,

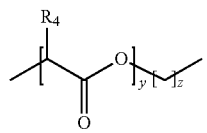

$R_4$=—H, —$CH_3$, —$C_2H_5$
y=1-10
z=0-22

In another embodiment, the invention provides a polymer having the following structure:

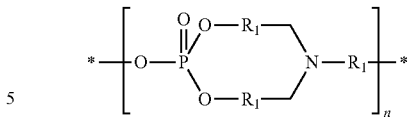

n>3
$R_1$=any alkyl chain.

Three representative cationic monomers of formula (III) useful for making cationic polymers of formula (I), and ultimately the zwitterionic polymers of formula (II) are illustrated in FIG. 1. Referring to FIG. 1, three positively charged polyacrylamides having pendant groups that bear cationic carboxybetaine ester groups are illustrated. The three monomers have different spacer groups ($L_2$: $CH_2)_n$—) between the quaternary ammonium groups (cationic center) and the ester (hydrolyzable) groups: CBAA-1-ester (n=1); CBAA-3-ester (n=3); and CBAA-5-ester (n=5). Polymerization of the monomers provides the corresponding cationic polymers. The three monomers were polymerized using free radical polymerization to form linear polymers, or using surface-initiated ATRP to prepare polymer brushes on SPR sensors. The polymers with different spacer groups ($L_2$) and ester groups were expected to have different chemical, physical and biological properties. The synthesis of the three monomers and their polymerizations are described in Example 1.

Figure 2:
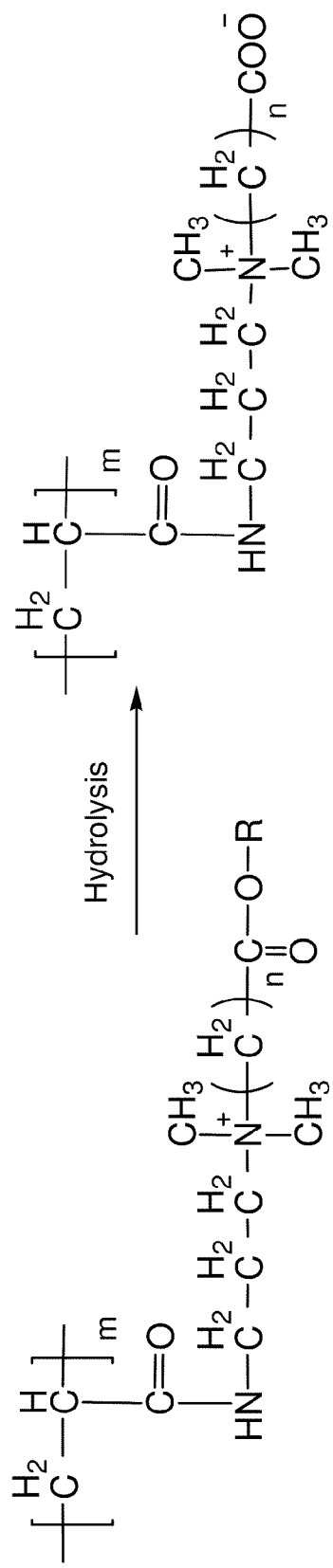
FIG. 2 illustrates the hydrolysis of a representative cationic polymer of the invention: hydrolysis of a cationic polycarboxybetaine ester to zwitterionic polycarboxybetaine.
Figure 3:
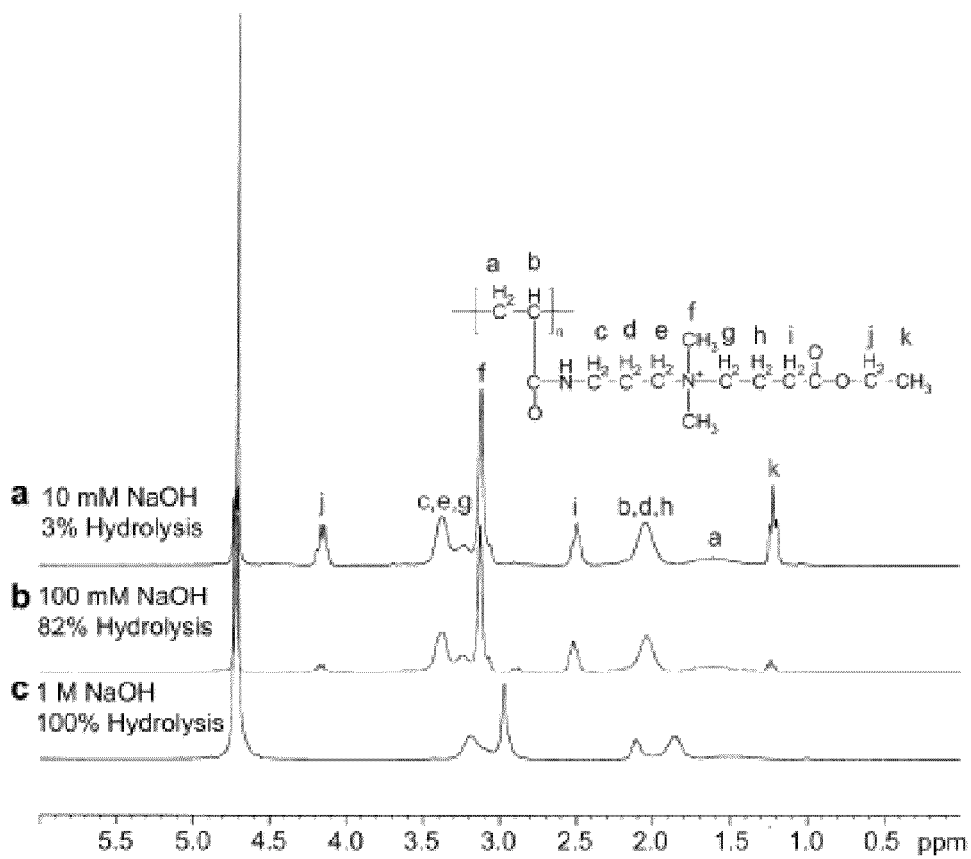
FIG. 3 compares the $^1$H NMR spectra of the hydrolysis of a representative cationic polymer of the invention, poly-CBAA-3-ester, after one-hour treatment in a solution with the sodium hydroxide concentration of (a) 10 mM (3% hydrolysis), (b) 100 mM (82% hydrolysis), and (c) 1 M (100% hydrolysis).
Figure 4:
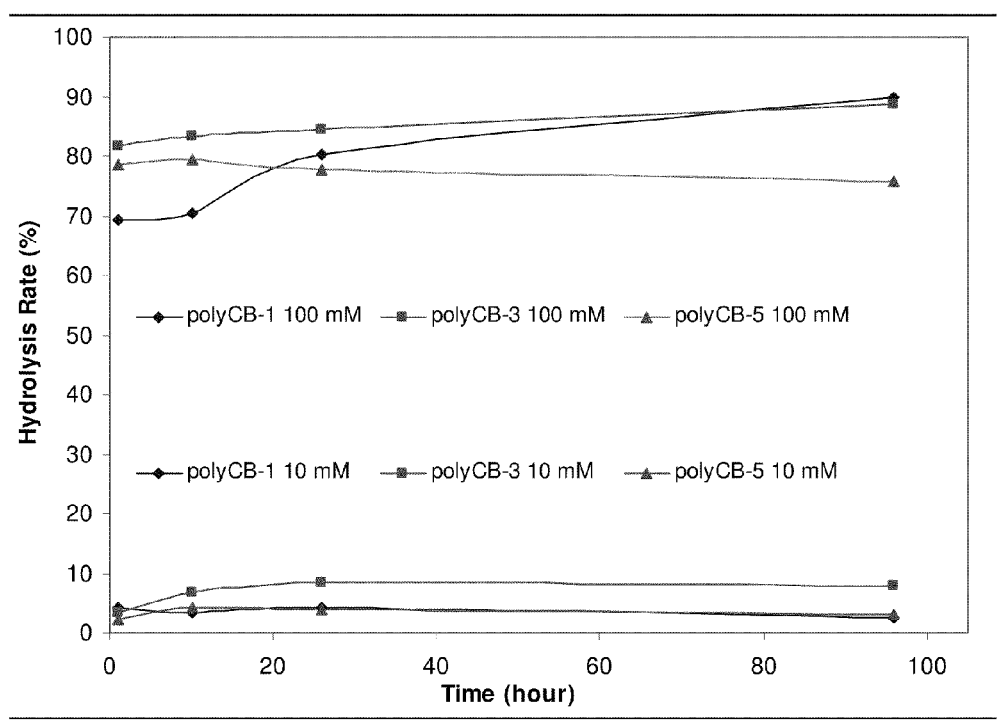
FIG. 4 compares the hydrolysis rates of representative cationic polymers of the invention at 10 mM and 100 mM aqueous sodium hydroxide.

For the linear polymers polymerized via free radical polymerization, their molecular weights were measured using gel permeation chromatography (GPC) in aqueous solutions. PolyCBAA-1-ester, polyCBAA-3-ester, and polyCBAA-5-ester had average molecular weights of 14 kDa, 13 kDa, and 9.6 kDa, respectively Hydrolysis of the cationic polymers provides the zwitterionic polymers (i.e., zwitterionic polycarboxybetaines). The hydrolysis of representative cationic polymer of the invention is described in Example 2 and illustrated schematically in FIG. 2. In FIG. 2, n is 1, 3, or 5 (corresponding to polyCBAA-1-ester, polyCBAA-3-ester, and polyCBAA-5-ester, respectively). The three carboxybetaine ester polymers were dissolved under different sodium hydroxide concentrations and their hydrolysis behavior was studied. After a period of time, the hydrolysis rate of the polymers was analyzed by measuring the retaining ester groups on the polymer using $^1$H NMR. All the three polymers are stable in water and no evident hydrolysis was detected after four days. The concentration of NaOH is crucial for the hydrolysis of the carboxybetaine ester polymers. FIG. 3 illustrates the NMR spectra of polyCBAA-3-ester after a one-hour treatment with three different concentrations of NaOH. For NaOH solution with a concentration of 10 mM, only slightly hydrolysis was detected (ca. 3%). For 100 mM NaOH solution, about 82% polymer was hydrolyzed. For the NaOH concentration of 1 M, the polymer was totally hydrolyzed in one hour. FIG. 4 graphs the hydrolysis rate under 100 mM or 10 mM NaOH as a function of time. Referring to FIG. 4, under these two NaOH concentrations, most hydrolysis happens in the first hour. After that, the hydrolysis rate changes only slightly with the time.

As noted above, the hydrolysis rate of the cationic polymers of the invention can be controlled by modifying their structures. To obtain the different hydrolysis behavior, cationic polymers having varying structure parameters such as ester groups (hydrolyzable groups), spacer groups ($L_1$ and $L_2$), and counter ions ($X^-$). Hydrolysis behavior can also be controlled by varying polymer molecular weight or copolymerizing with other monomers. Hydrolyzable ester groups (such as t-butyl and alkyl substituted silyl) or anhydride groups can be easily hydrolyzed under acidic or basic condition. Changing spacer groups ($L_2$: —$CH_2$)$_n$—) between the quaternary ammonium groups (cationic center) and the ester (hydrolyzable) groups also can tune the hydrolysis rate. Short spacers can increase the hydrolysis rate. In addition, counter ions, such as hydrophilic anions (e.g., $Cl^-$, $Br^-$, $I^-$, $SO_4$) also increase the hydrolysis rate, and low polymer molecular weight and copolymerization with other hydrophilic monomers also help to increase the hydrolysis rate.

Protein Adsorption

The hydrolyzable cationic polymers of the invention can advantageously be used as materials effective in reducing protein adsorption to surfaces treated with the polymers. The cationic polymers can be used to prepare low-fouling surfaces. These surfaces can be advantageously employed for devices in environments where the protein adsorption to device surfaces are detrimental.

To demonstrate the utility of representative cationic polymers of the invention in providing surfaces having low protein adsorption, polymer brushes were prepared from representative cationic polymers as described in Example 3 and their protein adsorption measured.

The three monomers (CBAA-1-ester, CBAA-3-ester, and CBAA-5-ester) were grafted on the surfaces of a SPR sensor using surface-initiated ATRP. The polymer brushes had a thickness of 5-20 nm estimated from XPS analysis. Protein adsorption from a 1 mg/mL fibrinogen solution on the three polymer brushes was measured using SPR. Fibrinogen is a sticky protein and plays an important role in platelet aggregation and blood clotting on biomaterials. Fibrinogen adsorption was 195 ng/cm$^2$, 255 ng/cm$^2$, and 600 ng/cm$^2$ for polyCBAA-1-ester, polyCBAA-3-ester, and polyCBAA-5-ester, respectively (see FIGS. 5A-5C). All three polymers have evident protein adsorption due to their positive charges. PolyCBAA-1-ester had relatively lower fibrinogen adsorption due to its higher hydrophilicity compared to the other two esters having more hydrophobic $L_2$ (i.e., C3 and C5, respectively). With the increase in $L_2$ from methylene to propylene to pentylene, the hydrophobicity of the polymer increases, leading to higher fibrinogen adsorption.

Figure 5A:
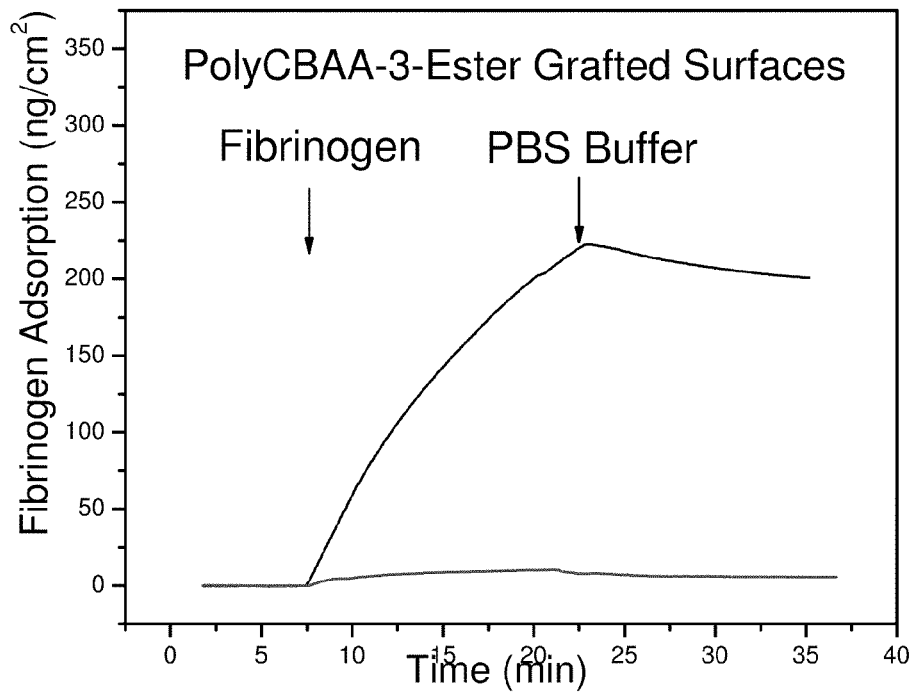
FIGS. 5A-5C are SPR sensorgrams for fibrinogen adsorption on the surfaces grafted with representative polymers of the invention: polycarboxybetaine esters before and after hydrolysis; (a) polyCBAA-1-ester, (b) polyCBAA-3-ester, and (c) polyCBAA-5-ester. The surfaces with polymer brushes were hydrolyzed with a 100 mm NaOH solution for 1-2 h.
Figure 5B:
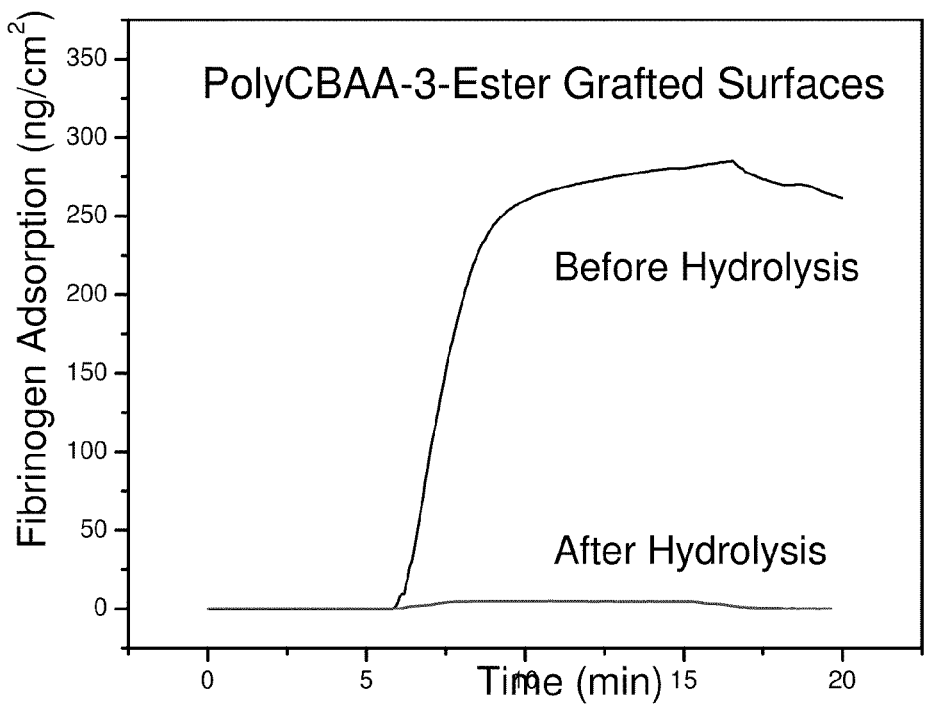
Figure 5C:
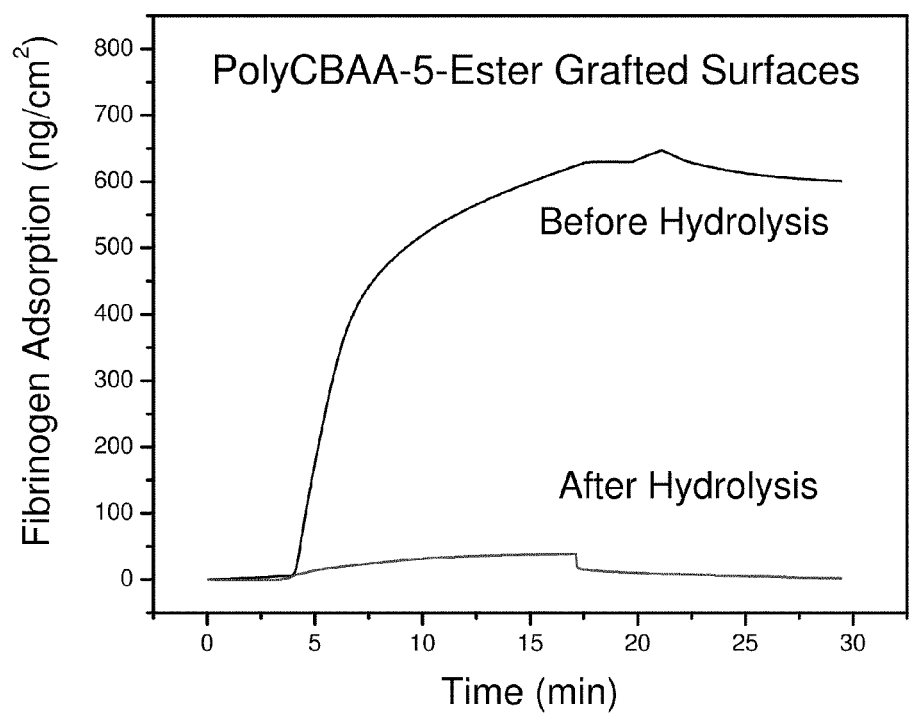

After hydrolysis at 100 mM for 1-2 hours, surface properties were dramatically changed. FIGS. 5A-5C illustrate that the surfaces grafted with each of the three polymers were converted to surfaces that were highly resistant to fibrinogen adsorption. On the surfaces with hydrolyzed polyCBAA-1-ester and hydrolyzed polyCBAA-3-ester, fibrinogen adsorption is less than 0.3 ng/cm$^2$, which is the detection limit of the SPR. Fibrinogen adsorption on hydrolyzed polyCBAA-5-ester was about 1.5 ng/cm$^2$. By controlling hydrolysis, the polymer-grafted surfaces can change their properties from high protein adsorption to strongly resistant to protein adsorption. Moreover, resulting surfaces with zwitterionic polymers after hydrolysis are biocompatible and highly resistant to nonspecific protein adsorption from blood plasma/serum and bacterial adhesion/biofilm formation.

Antimicrobial Properties

The hydrolyzable cationic polymers of the invention exhibit antimicrobial properties. The evaluation of antimicrobial properties of representative cationic polymers of the invention is described in Example 4.

To evaluate the antimicrobial properties of the cationic polycarboxybetaine esters, polymer solutions of polyCBAA-1-ester, polyCBAA-3-ester, and polyCBAA-5-ester were incubated with *E. coli*. It was found that at a concentration of 2 mM (repeat unit molar concentration), polyCBAA-1-ester, polyCBAA-3-ester, and polyCBAA-5-ester present a live cell percentage of 95%, 87.3%, and 46.2%, respectively (see FIG. 6). Antimicrobial activities appears to increase with the increase in the length of $L_2$. After hydrolysis, the zwitterionic polymers, polyCBAA-1, polyCBAA-3, and polyCBAA-5, exhibit a live cell percentage of 93.7%, 96.3% and 95.3%, respectively, indicating that the antimicrobial activity decreases with the hydrolysis of the cationic polymers (i.e., polycarboxybetaine esters) to the zwitterionic polymers (i.e., polycarboxybetaines).

Several amphiphilic polycations have been investigated for their antibacterial activities. The alkyl pendent chain length of the polycations was studied to compare the bactericidal efficiency of different polycations. It is found that the polymers with quaternary amine groups and longer hydrophobic pendant chains have better antimicrobial activities due to higher hydrophobicity. Small molecular quaternary ammonium compounds (QMCs) with carboxybetaine esters were found to have rapid bactericidal action when they have longer hydrocarbon groups. These QMCs could bind to the outer membrane and cytoplasmic membrane of enterobacteria and permeate into the bacterial membranes. The antimicrobial effect is increased with increasing the spacer length ($L_2$) of the cationic polymers (e.g., polycarboxybetaine esters) of the invention.

The antimicrobial efficacy of the polyCBAA-5-ester is comparable to that of other quaternized polymers with similar alkyl chain length. Higher antimicrobial efficacy can be achieved with longer alkyl chain lengths (e.g., $C_1$-$C_{20}$).

For conventional antimicrobial coatings, the killed microbes and adsorbed proteins usually accumulate on the surfaces and dramatically decrease their antimicrobial activities. In contrast, antimicrobial coatings made from the cationic polymers of the invention are hydrolyzed to zwitterionic polymers to provide surfaces that are highly resistant to the adsorption of various biomolecules. These zwitterionic polymers are nontoxic, biocompatible, and nonfouling, both as bulk materials and surface coatings.

Representative crosslinked zwitterionic polymers of the invention, polycarboxybetaines hydrogels, were non-cytotoxic and contain less than 0.06 units (EU)/mL of endotoxin using a *Limulus Amebocyte* Lysate (LAL) endotoxin assay kit (Cambrex Bioscience. Walkerville, Md.). The polycarboxybetaine hydrogels were implanted subcutaneously within mice for up to four weeks. The results showed that the polycarboxybetaines have in vivo biocompatibility comparable to that of poly(2-hydroxyethyl methacrylate (polyHEMA) hydrogels, a well-accepted model biomaterial for implantation. The nontoxic properties of the zwitterionic polymers convert the toxicity of their cationic polymer precursors and further provide nonfouling properties that can prevent dead microbes and adsorbed proteins from accumulating on the surface.

Cationic Polymer Coatings and Their Use in Medical Devices

The cationic polymers of the invention, hydrolyzable to zwitterionic polymers, can be advantageously used as coatings for the surfaces of a variety of devices including, for example, medical devices. In this embodiment, the cationic polymers of the invention provide switchable biocompatible polymer surfaces having self-sterilizing and nonfouling capabilities.

Figure 7:
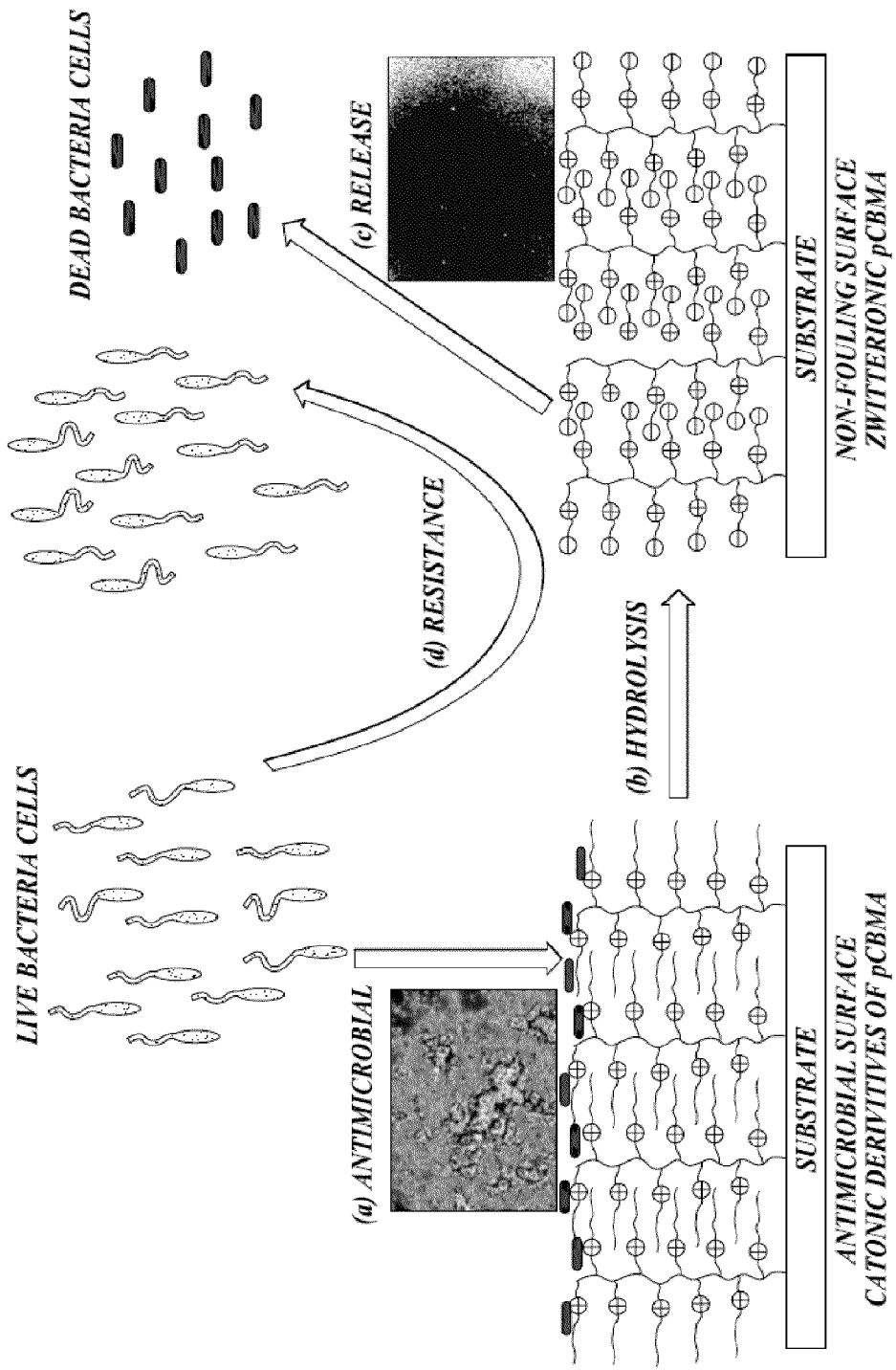
FIG. 7 is a schematic illustration of a representative surface of the invention coated with a cationic polymer. The surface switches from an antibacterial surface to a non-fouling surface upon hydrolysis: (a) antimicrobial cationic pCBMA-1 C2 effectively kills bacteria, (b) pCBMA-1 C2 is converted to non-fouling zwitterionic pCBMA-1 upon hydrolysis, (c) killed bacteria remaining on the surface is released from non-fouling zwitterionic pCBMA-1 demonstrating that (d) zwitterionic pCBMA-1 itself is highly resistant to bacterial adhesion.
Figure 8:
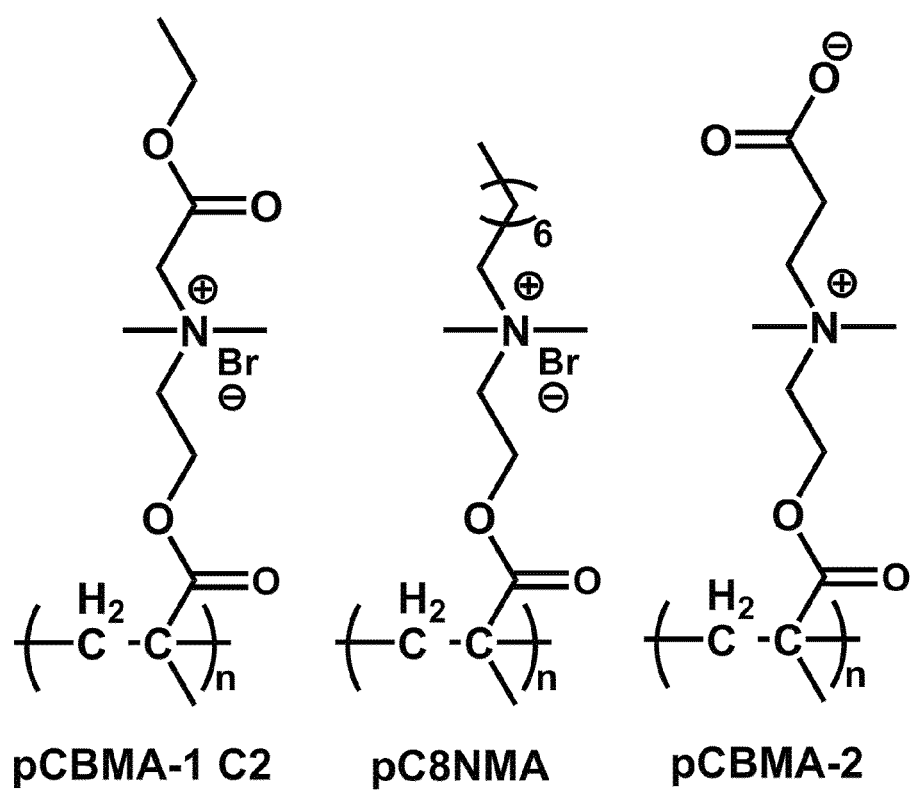
FIG. 8 illustrates the chemical structures of a representative cationic polymer of the invention, switchable pCBMA-1 C2; antimicrobial cationic pC8NMA; and non-fouling zwitterionic pCBMA-2.

FIG. 7 is a schematic illustration of a switchable biocompatible polymer surfaces having self-sterilizing and nonfouling capabilities. Referring to FIG. 7, antimicrobial surface (a) is a surface coated with a representative cationic polymer of the invention (i.e., pCBMA-1 C2, see FIG. 8) that effectively kills bacteria. On hydrolysis (b) the representative cationic polymer is converted to a nonfouling zwitterionic polymer (i.e., pCBMA-1, the carboxylate corresponding to pCBMA-1 C2 ester) and dead bacteria remaining on the surface are released (c) from the nonfouling zwitterionic polymer (i.e., pCBMA-1) to provide a surface coated with the zwitterionic polymer, which is highly resistant to bacterial adhesion (d).

The materials of the invention (e.g., polymers, hydrogels) are advantageously used to coat surfaces to provide biocompatible, antimicrobial, and nonfouling surfaces. Accordingly, in another aspect, the invention provides devices and materials having a surface (i.e., one or more surfaces) to which have been applied (e.g., coated, covalently coupled, ionically associated, hydrophobically associated) one or more materials of the invention. Representative devices and carriers that may be advantageously treated with a material of the invention, modified to include a material of the invention, or incorporates a material of the invention include:

particle (e.g., nanoparticle) having a surface treated with, modified to include, or incorporates a material of the invention;

drug carrier having a surface treated with, modified to include, or incorporates a material of the invention;

non-viral gene delivery system having a surface treated with, modified to include, or incorporates a material of the invention;

biosensor having a surface treated with, modified to include, or incorporates a material of the invention;

devices for bioprocesses or bioseparations, such as membranes for microbial suspension, hormone separation, protein fractionation, cell separation, waste water treatment, oligosaccharide bioreactors, protein ultrafiltration, and diary processing having a surface treated with, modified to include, or incorporates a material of the invention;

implantable sensor having a surface treated with, modified to include, or incorporates a material of the invention;

subcutaneous sensor having a surface treated with, modified to include, or incorporates by a material of the invention;

implant, such as a breast implant, cochlear implant, and dental implant having a surface treated with, modified to include, or incorporates a material of the invention;

contact lens having a surface treated with, modified to include, or incorporates a material of the invention;

tissue scaffold having a surface treated with, modified to include, or incorporates a material of the invention;

implantable medical devices, such as an artificial joint, artificial heart valve, artificial blood vessel, pacemaker, left ventricular assist device (LVAD), artery graft, and stent having a surface treated with, modified to include, or incorporates a material of the invention; and medical devices, such as an ear drainage tube, feeding tube, glaucoma drainage tube, hydrocephalous shunt, keratoprosthesis, nerve guidance tube, urinary catheter, tissue adhesive, and x-ray guide having a surface treated with, modified to include, or incorporates by a material of the invention.

Microbial adhesion onto implanted biomaterials and the subsequent formation of biofilms is one of the major causes of biomedical device failure. The use of antimicrobial and nonfouling coatings are two strategies for the prevention of the attachment and spreading of microorganisms on the surfaces of implantable materials. Antimicrobial surfaces containing covalently linked quaternary ammonium compounds (QACs) have proved to be able to efficiently kill a variety of microorganisms. A major problem with QAC surfaces is the attachment of dead microorganisms remaining on antimicrobial coatings, which can trigger an immune response and inflammation, and block its antimicrobial functional groups. In addition, such antimicrobial coatings can not fulfill the requirements of nonfouling and biocompatibility as implantable biomaterials. Poly(ethylene glycol) (PEG) derivatives or zwitterionic polymers have been extensively used as nonfouling materials to reduce bacterial attachment and biofilm formation. However, the susceptibility of PEG to oxidation damage has limited its long-term application in complex media. Zwitterionic materials such as poly(sulfobetaine methacrylate) (pSBMA) are able to dramatically reduce bacterial attachment and biofilm formation and are highly resistant to nonspecific protein adsorption, even from undiluted blood plasma and serum. Although zwitterionic coatings can reduce the initial attachment and delay colonization of microbes on surfaces, there is a possibility of introducing pathogenic microbes into the patient during implantation operations and catheter insertions, which results in the failure of implanted devices; the use of antimicrobial agents will then be necessary to eliminate these microbes. Surface-responsive materials have been developed for a broad spectrum of applications, but it is still a great challenge to develop biocompatible materials that have both antimicrobial and nonfouling capabilities.

Other representative substrates and surfaces that may be advantageously treated with a material of the invention, modified to include a material of the invention, or incorporates a material of the invention include fabrics and such as in clothing (e.g., coats, shirts, pants, undergarments, including such as worn by hospital and military personnel), bedding (e.g., blankets, sheets, pillow cases, mattresses, and pillows), toweling, and wipes.

Other representative substrates and surfaces that may be advantageously treated with a material of the invention, modified to include a material of the invention, or incorporates a material of the invention include working surfaces such as tabletops, desks, and countertops.

As noted above, in one embodiment, the present invention provides a switchable polymer surface coating that combines the advantages of both nonfouling surface and that can kill greater than 99.9% of *Escherichia coli* K12 in one hour, with 98% of the dead bacterial cells released when the cationic derivatives are hydrolyzed to nonfouling zwitterionic polymers. pCBMA-1-C2 (cationic polymer of formula (I) where $L_1$ is —C(=O)OCH$_2$CH$_2$—, $L_2$ is —CH$_2$—, $R_c$ is CH$_2$CH$_3$, and X$^-$ is Br$^-$) control coatings were grafted by surface-initiated atom transfer radical polymerization (ATRP) onto a gold surface covered with initiators. The thicknesses of the obtained polymer coatings, as measured by atomic force microscopy (AFM), were 26-32 nm (Table 1).

TABLE 1

Film thicknesses (av ± std dev.) of pCBMA-1 C2, pC8NMA, and pCBMA-2 grafted onto gold-coated glass slides by ATRP and fibrinogen adsorption on these surfaces measured by SPR before and after hydrolysis under different conditions.

| | pCBMA-1 C1 | pC8NMA | pCBMA-2 |
|---|---|---|---|
| polymer brush thickness (nm) | (31.2 ± 2.4) | (27.8 ± 2.8) | (26.1 ± 2.5) |
| protein adsorption (ng cm$^{-2}$) | | | |
| 0 h | 229.2 | 243.4 | 1.5 |
| 24 h H$_2$O | 189.9 | — | — |
| 24 h CHES (pH 9.0) | 114.9 | — | — |
| 24 h CAPS (pH 10.0) | 0 | 285.1 | 0.7 |

Figure 9:
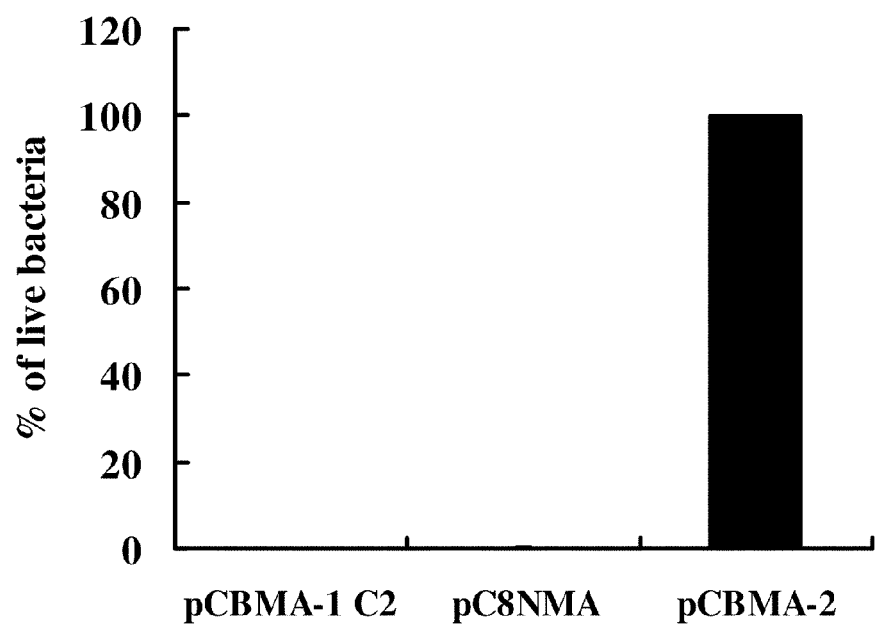
FIG. 9 is a graph comparing bactericidal activity of pCBMA-1 C2 and pC8NMA against E. coli K12. The percentage of live E. coli K12 colonies that grew on the surfaces coated with antimicrobial polymers is relative to the number of colonies that grew on the pCBMA-2 control (n=3).
Figure 10A:
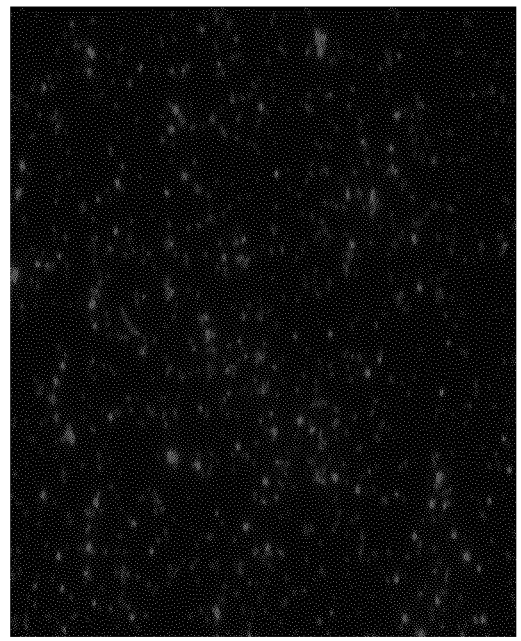
FIGS. 10A-10F are fluorescence microscopy images of attached E. coli K12 cells (red color) from a suspension with 10$^{10}$ cellsmL$^{-1}$ for one-hour exposure to the surfaces covered with various polymers: (a), (c), and (e) are for pCBMA-1 C2, pC8NMA pCBMA-2, respectively, before hydrolysis and (b), (d), and (f) are for the same polymers, respectively, after hydrolysis. Hydrolysis was for 8 days with 10 mM CAPS (pH 10.0).
Figure 10B:
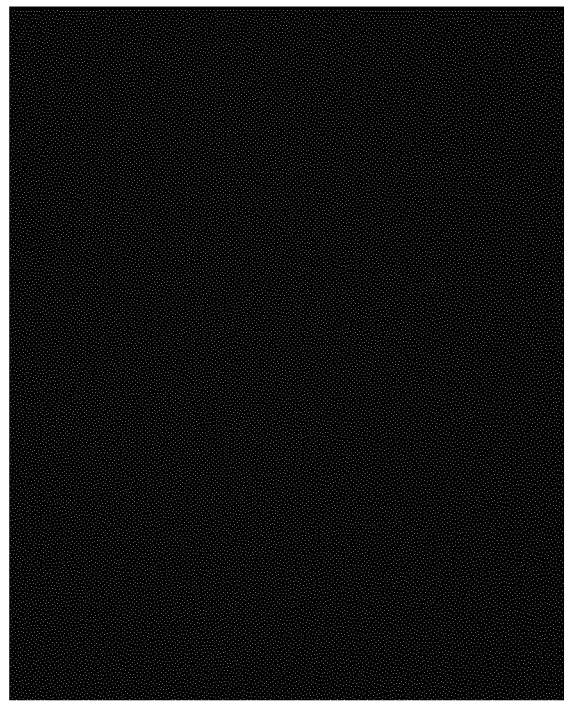
Figure 10C:
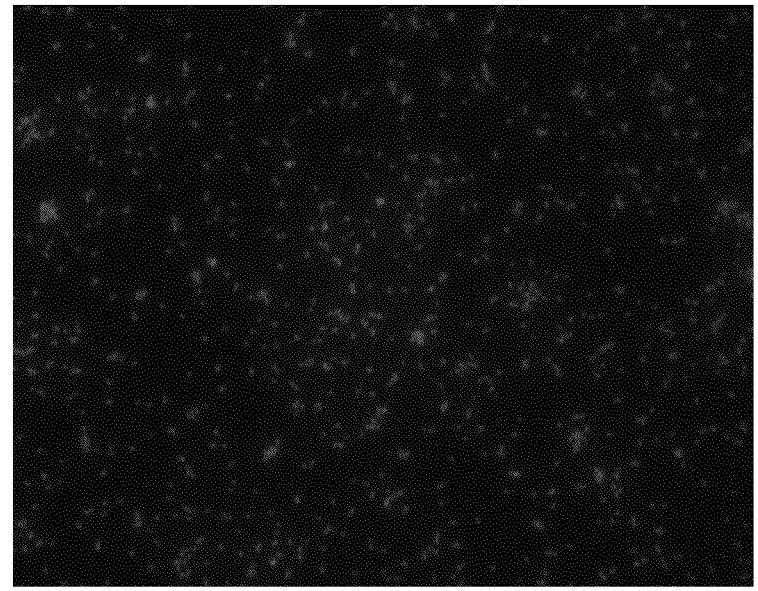
Figure 10D:
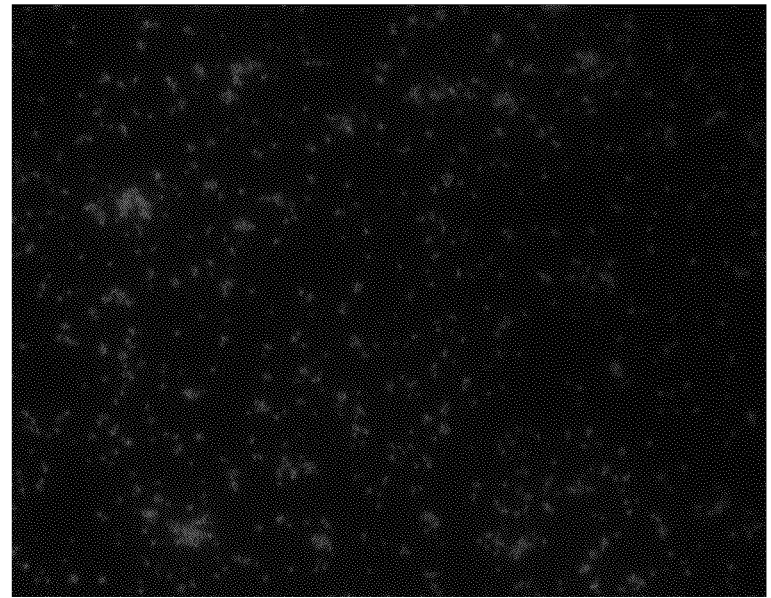
Figure 10E:
Figure 10F:
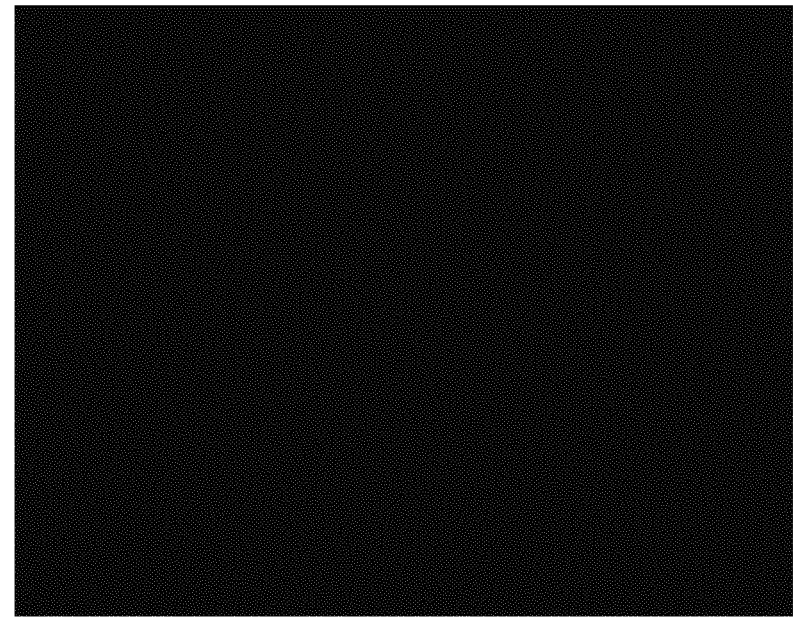

The bactericidal activity of pCBMA-1 C2 surfaces was determined using *E. coli* K12, according to a modified literature procedure (Tiller et al., *Proc. Natl. Acad. Sci. USA* 98:5981, 2001). The permanently cationic poly(methacryloyloxyethyl-dimethyloctylammonium bromide) (pC8NMA, cationic control, (see FIG. 8) and the zwitterionic poly(2-carboxy-N,N-dimethyl-N-[2'-(methacryloyloxy)ethyl]ethanaminium) (pCBMA-2, zwitterionic control, see FIG. 8) were used as the positive and the negative control surfaces, respectively. The antimicrobial efficiency was defined as the amount of live cells on the tested surfaces relative to those on the pCBMA-2 surface. FIG. 9 shows that pCBMA-1 C2 and pC8NMA surfaces kill greater than 99.9% and 99.6%, respectively, of the E. coli in one hour relative to pCBMA-2 surfaces. The total number of live bacterial cells on the gold surface, which was also used as a negative-control surface, is similar to that on the pCBMA-2 surface.

Figure 11:
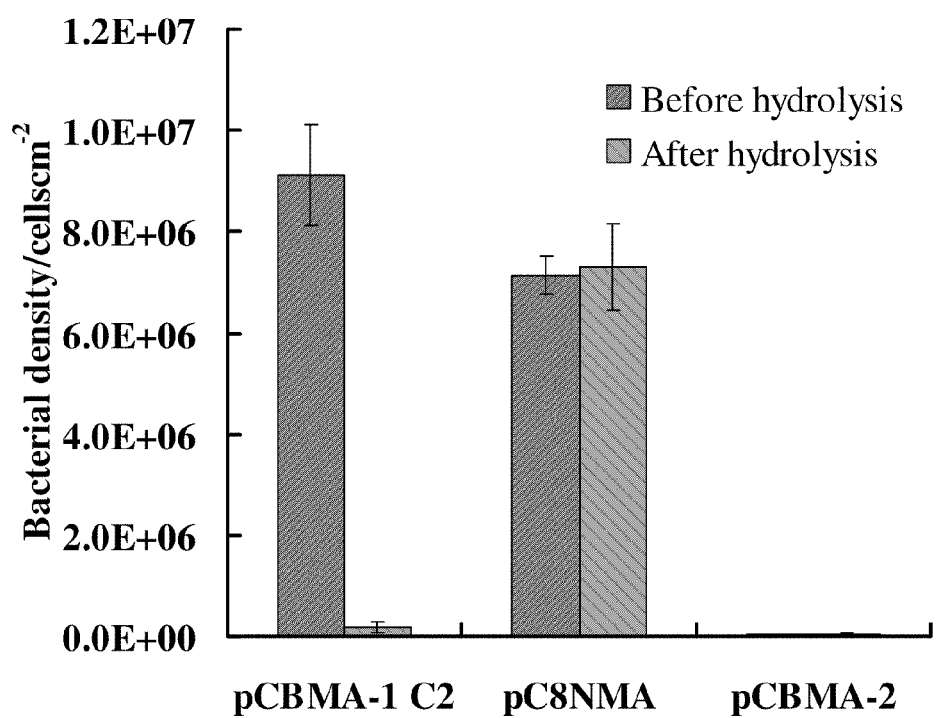
FIG. 11 is a graph comparing the attachment of E. coli K12 from a suspension with 10$^{10}$ cells mL$^{-1}$ for one-hour exposure to pCBMA-1 C2, pC8NMA, and pCBMA-2 before and after hydrolysis (n=3).

The attachment and release of E. coli K12 were tested on the pCBMA-1 C2 surfaces before and after hydrolysis. Cationic pC8NMA and zwitterionic pCBMA-2 were used as the negative and the positive nonfouling control surfaces, respectively, and as the positive and the negative antimicrobial control surfaces, respectively. FIGS. 10A-10F show that large amounts of bacteria were attached to the cationic pCBMA-1 C2 and pC8NMA surfaces before hydrolysis, whereas very few bacterial cells were attached to the zwitterionic pCBMA-2 surface. In contrast to pC8NMA, pCBMA-1 C2 released the majority of cells after hydrolysis while pCBMA-2 remained nonfouling FIG. 11 shows quantitative data for the amount of bacterial cells remaining on all three polymer surfaces before and after hydrolysis. There were similar amounts of bacterial residues on both cationic pCBMA-1 C2 and pC8NMA surfaces before hydrolysis, while the amount of attached cells on the pCBMA-2 surface is less than 0.3% of that on both cationic pCBMA-1 C2 and pC8NMA surfaces. To test the release of bacterial residues, the three surfaces were incubated in N-cyclohexyl-3-aminopropanesulfonic acid (CAPS) buffer (10 mM, pH 10.0) at 37° C. for 8 days. The pCBMA-1 C2 surfaces were hydrolyzed to poly(N-(carboxymethyl)-N,N-dimethyl-2-[(2-methyl-1-oxo-2-propen-1-yl)-oxy]ethanaminium) (pCBMA-1) and 98% of the dead bacterial cells were released. In contrast, no release of the dead cells was observed on pC8NMA surfaces (p>0.1) while pCBMA-2 surfaces retained very low bacterial adhesion.

The release of the attached bacterial cells is dependent on the conversion of cationic pCBMA-1 C2 into zwitterionic pCBMA-1. Hydrolysis rate of betaine esters is influenced by several factors, such as the length of the spacer ($L_2$) between the quaternary amine and the carboxyl groups, the nature of the hydrolyzable group, temperature, and pH value. The majority of polymer chains of the ester group used were hydrolyzed. The hydrolysis rate of the betaine esters is also slower after bacterial cells and proteins are attached to the surface. pCBMA-1 C2, which has one methylene spacer ($L_2$), was chosen and the experimental temperature was set at 37° C. to achieve a fast hydrolysis rate and to provide a physiologically relevant temperature. The protein adsorption results (see Table 2) showed that the clean, cationic pCBMA-1 C2 surface was hydrolyzed into a nonfouling zwitterionic surface after only 24 h at 37° C. and pH 10.0, while it took 48 h to form a nonfouling surface and release bacterial residues after the attachment of bacteria from an E. coli K12 suspension of $10^7$ cells $mL^{-1}$. When bacterial cells were attached to the pCBMA-1 C2 surface from a suspension of $10^{10}$ cells $mL^{-1}$, the release of attached bacteria took eight days under the same hydrolysis conditions.

Figure 12A:
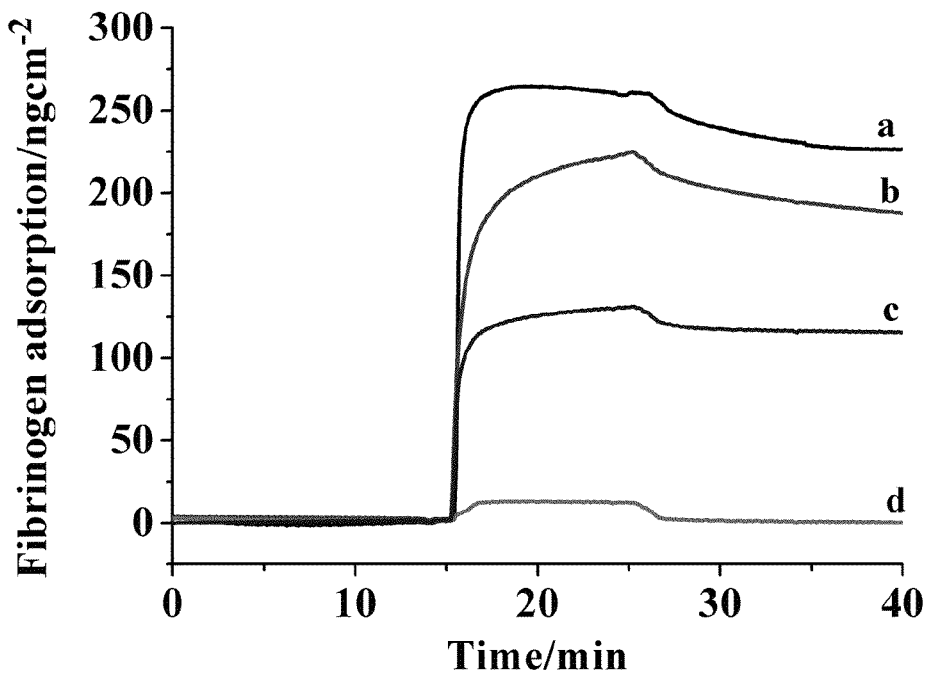
FIG. 12A compares SPR sensorgrams showing the adsorption of 1 mg mL$^{-1}$ fibrinogen in PBS buffer on the surfaces grafted with pCBMA-1 C2 via ATRP (a) before hydrolysis, and (b), (c) and (d) after 24 hr hydrolysis with water, 10 mM CEHS at pH 9.0, and 10 mM CAPS at pH 10.0, respectively.
Figure 12B:
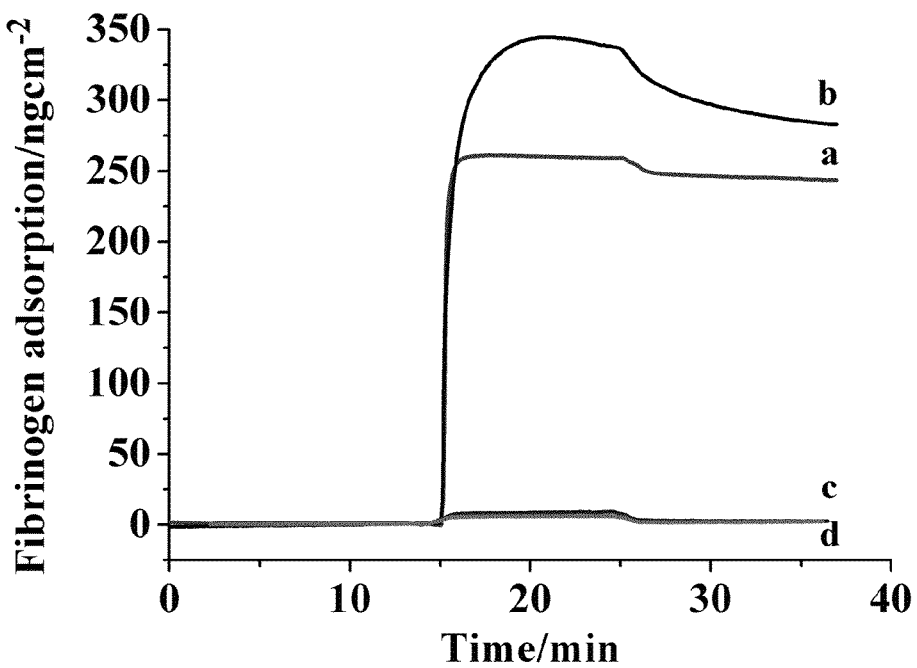
FIG. 12B compares SPR sensorgrams showing the adsorption of 1 mg mL$^{-1}$ fibrinogen in PBS buffer on the surfaces grafted with pC8NMA (a) before and (b) after 24 hr incubation with 10 mM CAPS at pH 10.0, and on the surfaces grafted with pCBMA-2 (c) before hydrolysis and (d) after 24 h of hydrolysis with 10 mM CAPS at pH 10.0.

Nonspecific protein adsorption on various surfaces was measured by a surface plasmon resonance (SPR) sensor to determine the nonfouling characteristics of the surfaces (see Table 2). Hydrolysis conditions for pCBMA-1 C2 and control surfaces were investigated in situ in the SPR sensor. FIGS. 12A and 12B show representative SPR sensorgrams for fibrinogen adsorption on pCBMA-1 C2 and control surfaces over time. The fibrinogen adsorption on pCBMA-1 C2 before hydrolysis was 229.2 ng $cm^{-2}$. After 24 h of incubation with CAPS buffer (pH 10.0), there was no measurable protein adsorption on the pCBMA-1 C2 surface, which indicated that pCBMA-1 C2 was completely hydrolyzed to nonfouling zwitterionic pCBMA-1. In contrast, hydrolysis of pCBMA-1 C2 was not complete after 24 h incubation in either water or N-cyclohexyl-2-aminoethanesulfonic acid (CEHS) buffer (pH 9.0). As shown in FIG. 12B, high fibrinogen adsorption was observed on the pC8NMA surface before and after the surface was incubated with CAPS buffer (pH 10.0) for 24 h at 37° C. However, under identical conditions, the pCBMA-2 surface still exhibited excellent nonfouling properties, with less than 2 ng $cm^{-2}$ fibrinogen absorption. This result indicates that the obtained zwitterionic surfaces are highly resistant to protein adsorption and are qualified as ultralow fouling surfaces, which are required for the surface coatings of implantable medical devices.

In this embodiment, the invention provides a switchable polymer surface that integrates antimicrobial and nonfouling properties and is biocompatible. The representative cationic polymer (i.e., precursor of pCBMA) is able to kill bacterial cells effectively and switches to a zwitterionic nonfouling surface and releases dead bacterial cells upon hydrolysis. Moreover, the resulting nonfouling zwitterionic surface can further prevent the attachment of proteins and microorganisms and reduce the formation of a biofilm on the surface. The switchable process from antimicrobial to nonfouling surfaces can be tuned through adjusting the hydrolysis rate of these polymers for specific requirements of applications.

Figure 13:
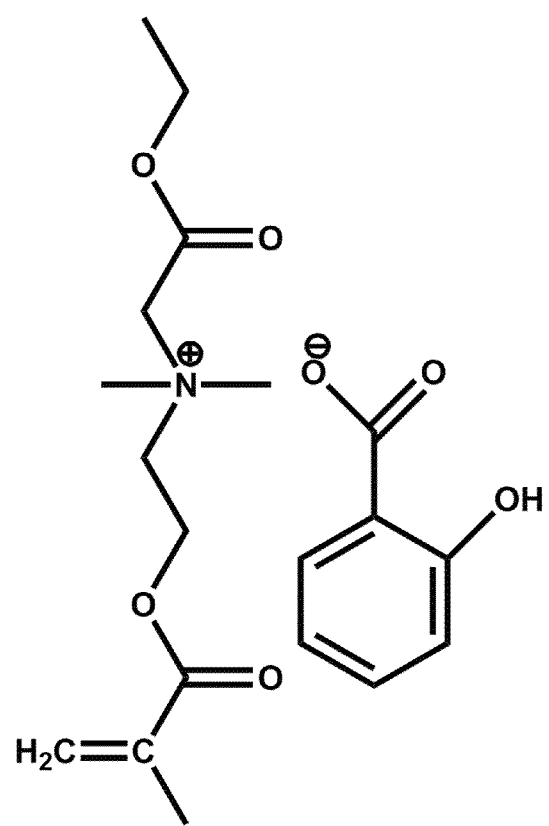
FIG. 13 illustrates the structure of a representative cationic monomer useful for making cationic polymers of the invention: CBMA-1 C2 SA, the ethyl ester of CBMA-1 having a salicylate counter ion.
Figure 14:
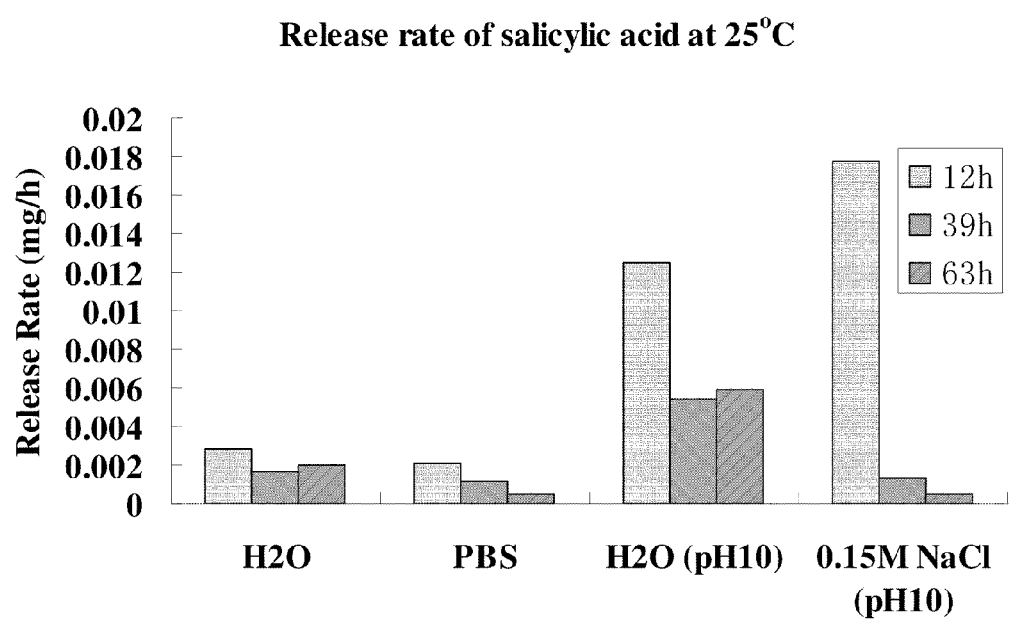
FIG. 14 compares the release rate (mg/h) of salicylic acid over time (12 h, 39 h, and 63 h) at 25° C. under four conditions from hydrogels prepared by polymerizing CBMA-1 C2 SA: (a) water, neutral pH; (b) phosphate buffered saline (PBS); (c) water, pH 10; and (d) 0.15 M aqueous sodium chloride, pH 10.
Figure 15:
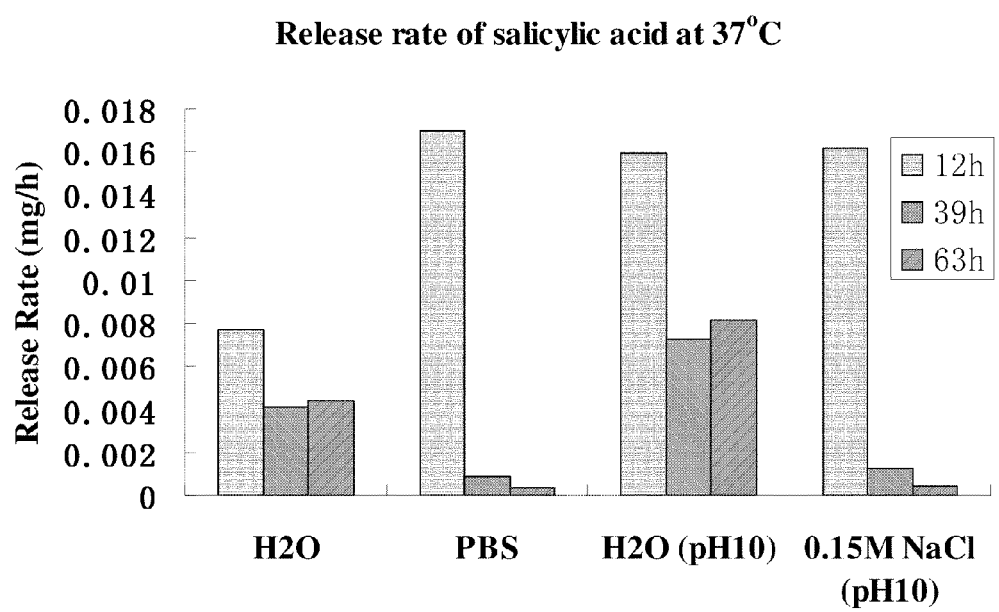
FIG. 15 compares the release rate (mg/h) of salicylic acid over time (12 h, 39 h, and 63 h) at 37° C. under four conditions from hydrogels prepared by polymerizing CBMA-1 C2 SA: (a) water, neutral pH; (b) phosphate buffered saline (PBS); (c) water, pH 10; and (d) 0.15 M aqueous sodium chloride, pH 10.

As noted above, the cationic polymers of the invention can include a hydrophobic counter ion or a counter ion having therapeutic activity (e.g., antimicrobial or antibacterial activity. A representative polymer having a salicylate counter ion (polyCBMA-1 C2) can be prepared from the monomer illustrated in FIG. 13: CBMA-1 C2 ("1" indicates one carbon between two charged groups and "C2" indicates C2 ester). PolyCBMA-1 C2 hydrogel loaded with salicylic acid (SA) as its counter ion was prepared by copolymerizing 1 mM CBMA-1 C2 SA monomer (FIG. 13) with 0.05 mM tetraethylenglycoldimethacrylate in 1 ml of solvent (ethylene glycol:water:ethanol=1:2:1) at 65° C. for 2 hours. The resulting hydrogel was soaked in DI water for 12 hours. The hydrogel was cut into round disks with 1 cm diameter. The hydrogel disks were then transferred into solutions with different pH and ionic strength and incubated at 25° C. or 37° C. At different time points the aqueous phase was completely removed and new solutions were added. The release of SA into the aqueous phase was measured by high performance liquid chromatography (HPLC). The release rate of SA is defined as the amount of released SA divided by time (mg/h). The release rate of SA from pCBMA-1 C2 SA hydrogel depends on temperature, ionic strength, and pH. FIG. 14 and FIG. 15 indicated that higher pH promotes the release of SA and that increased ionic strength can slightly increase the release rate of SA. By comparing FIG. 14 and FIG. 15, it can be observed that the elevated temperature results in a faster release of SA in water and phosphate buffered saline (PBS). The release rate of SA decreases as a function of time for all the conditions.

Cationic Polymer Coatings and Their Use in Wound Dressings

The cationic polymers useful in the invention, hydrolyzable to zwitterionic polymers, can be advantageously incorporated into hemostatic wound dressings. The cationic polymers useful in the invention provide switchable biocompatible polymer surfaces having self-sterilizing and nonfouling capabilities.

Accordingly, in another aspect, the invention provides wound dressings and related materials having a surface (i.e., one or more surfaces) to which have been applied (e.g., coated, covalently coupled, ionically associated, hydrophobically associated) one or more materials of the invention. Representative wound dressings and related materials devices are advantageously treated with a material of the invention, modified to include a material of the invention, or incorporate a material of the invention.

As noted above, the present invention provides switchable biocompatible polymer surfaces having self-sterilizing and non-fouling capabilities based on the cationic polymers useful in the invention (e.g., pCBMA ester). See FIG. 7. Antimicrobial cationic pCBMA ester can prevent bacterial infection and is converted to biocompatible and water-absorbent zwitterionic pCBMA upon hydrolysis.

In one embodiment, the wound dressing includes a hydrogel. In this embodiment, the hydrogel includes both a zwitterionic polymer as well as a cationic polymer (i.e., a cationic zwitterionic precursor polymer). The cationic zwitterionic precursor polymers are used for hemostatic and antimicrobial actions while the zwitterionic polymers are used as wound fluid adsorbents. After action, cationic zwitterionic precursor polymers are converted to nontoxic, non-sticky, and biocompatible zwitterionic polymers upon hydrolysis (controllable hydrolysis rates). In one embodiment, the wound dressing hydrogels can be prepared from two monomers (CBMA and CBMA ester) via polymerization or from just one monomer (CBMA ester) by partially hydrolyzing the pCBMA ester hydrogel.

Figure 16:
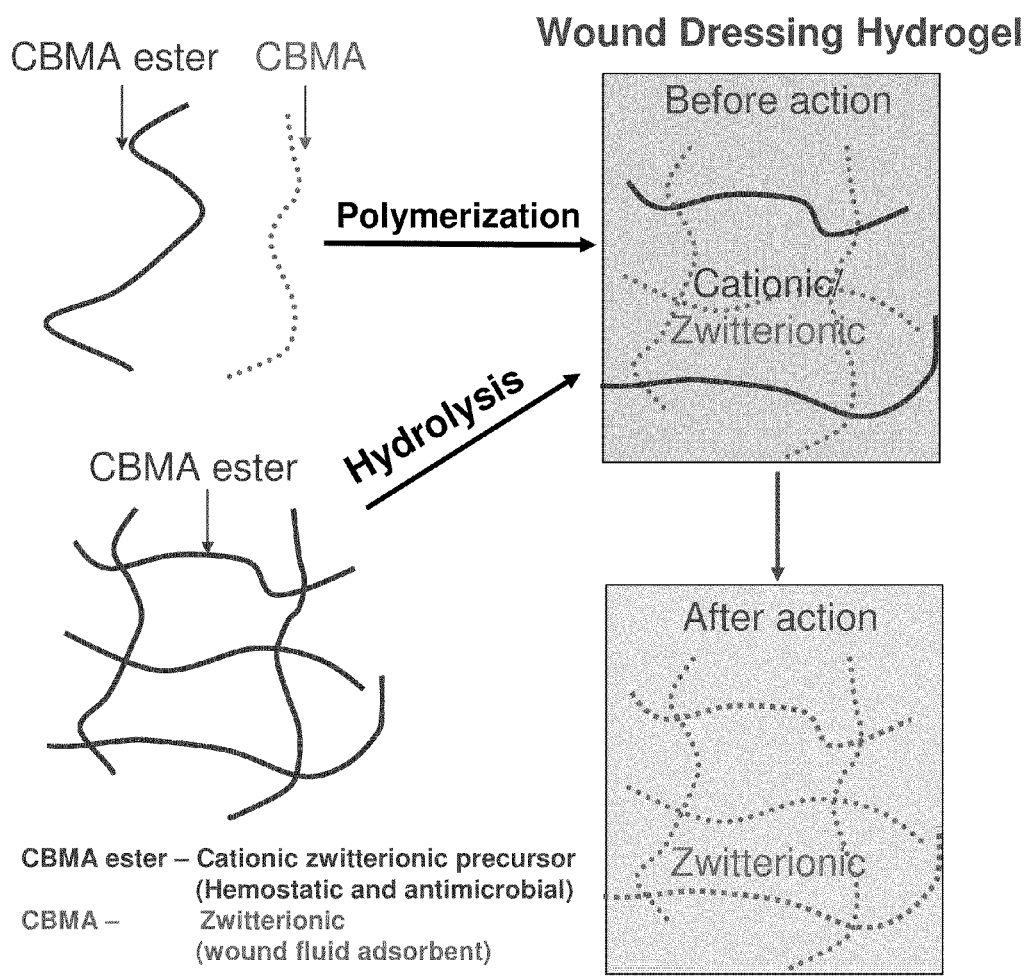
FIG. 16 illustrates schematic representative wound dressing hydrogels of the invention containing both zwitterionic and cationic zwitterionic precursor polymers. The cationic zwitterionic precursor polymers are useful for hemostatic and antimicrobial actions and the zwitterionic polymers are useful for wound fluid adsorbents. After action, cationic zwitterionic precursor polymers are converted to nontoxic, non-sticky, and biocompatible zwitterionic polymers by hydrolysis. These wound dressing hydrogels can be prepared from two monomers (e.g., CBMA and CBMA ester) via polymerization or from just one monomer (CBMA ester) by partially hydrolyzing the corresponding pCBMA ester hydrogel.

A representative wound dressing hydrogel of the invention is schematically illustrated in FIG. 16.

In one embodiment, the invention provides wound dressings based on an integrated formulation containing both cationic (e.g., pCBMA ester) and zwitterionic (e.g., pCBMA) polymers. These wound dressings containing both cationic and zwitterionic polymers improve hemorrhage control and survival, promote wound healing, and remove bacteria. The advantages of the wound dressings include (a) multiple hemostatic, antimicrobial, wound fluid-absorbent, and wound healing functions with high efficacy since cationic polymers (e.g., pCBMA ester) can attract red blood cells and kill bacteria while the zwitterionic polymer (e.g., pCBMA) can absorb wound fluids; (b) add-on wound fluid adsorbent capability, non-sticky, biocompatibility, and nontoxicity even at high concentrations when cationic polymers are converted to zwitterionic polymers upon hydrolysis; (c) simplicity, reproducibility, and low-cost since they can be prepared from only one or two monomers (i.e., CBMA ester and CBMA).

The wound dressings of the invention are based on cationic polymers hydrolyzable to zwitterionic polymers. The wound dressings include switchable polymer surfaces described above have both self-sterilizing and non-fouling/biocompatible capabilities. This cationic zwitterionic precursor polymer has unique performance as coatings on a surface or as additives to a solution. On hydrolysis, the cationic polymers are converted to zwitterionic polymers that are highly resistant to nonspecific protein adsorption from undiluted blood plasma and serum and bacterial adhesion/biofilm formation. The zwitterionic polymer hydrolysis products are also highly biocompatible with tissues from in vivo animal studies. The wound dressing includes a switchable polymer surface integrating antimicrobial and nonfouling/biocompatible properties. The antimicrobial cationic zwitterionic precursor surface can effectively kill bacterial cells and then switch to a non-fouling and biocompatible zwitterionic surface (see FIG. 7).

Figure 17A:
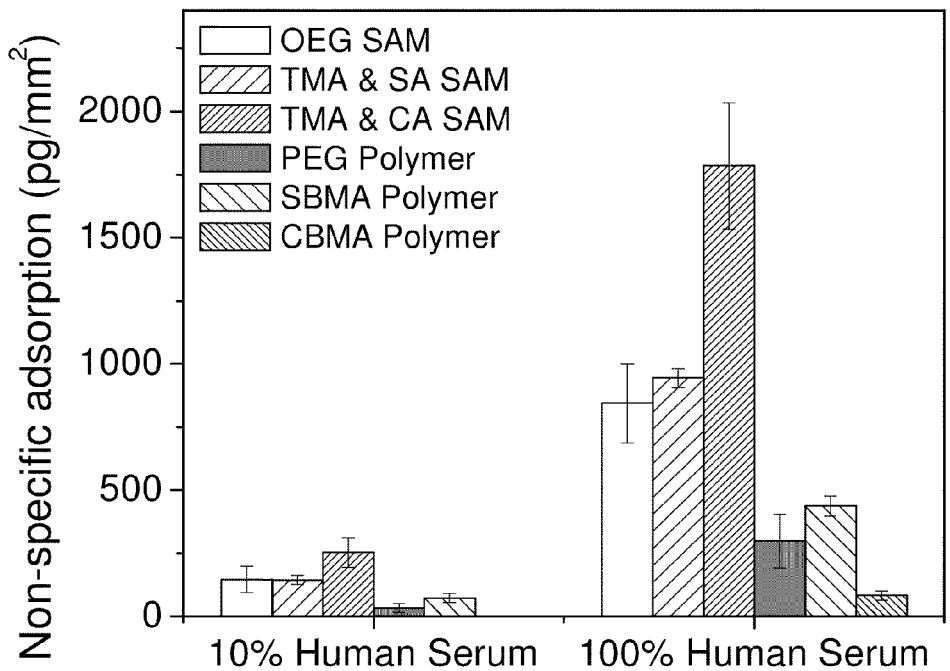
FIGS. 17A-17B illustrate the SPR response for nonspecific adsorption of 10% human serum in PBS and 100% human serum (17A) and non-specific adsorption of 10% human plasma in PBS and 100% human serum (17B). Error bars represent the standard error of the mean. An adsorbed protein monomer is equivalent to 2,500 pg/mm$^2$.
Figure 17B:
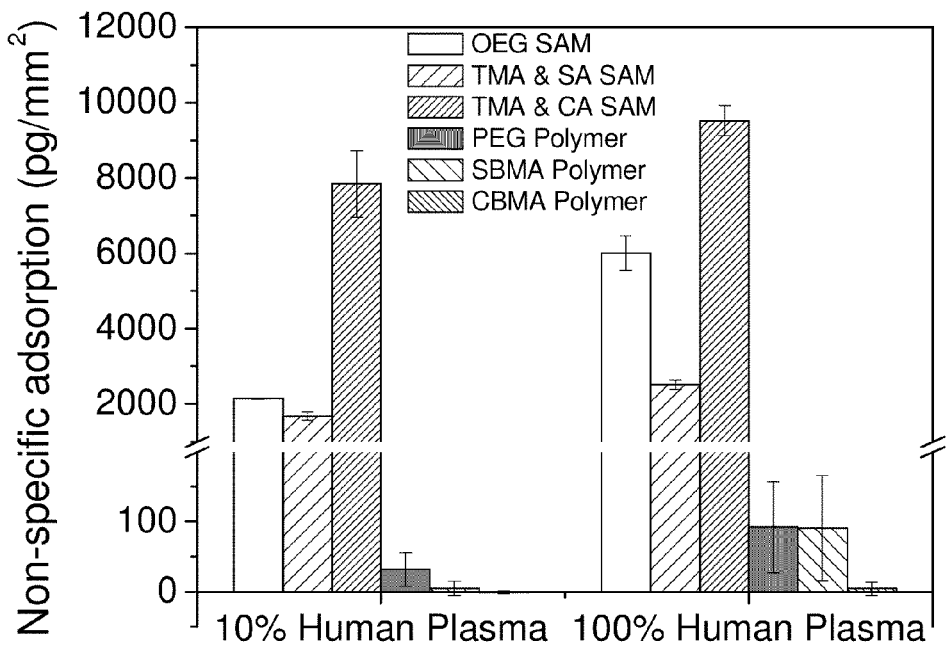
Figure 18:
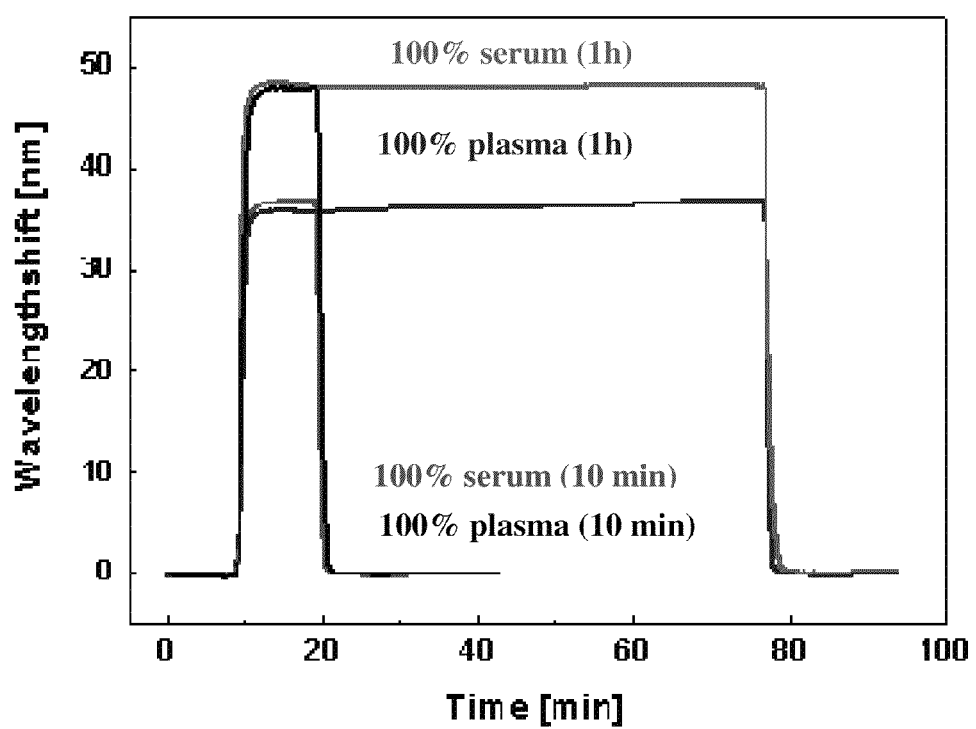
FIG. 18 illustrates the resistance of a representative zwitterionic polymer, CBAA-2, to nonspecific protein adsorption from 100% blood plasma and 100% serum (<0.3 ng/cm$^2$ adsorbed proteins).
Figure 19A:
FIGS. 19A-19H compares microscopy images of accumulated $P.$ $aeruginosa$ on surfaces treated with pCBMA (FIGS. 19C-19H, days 1, 3, 5, 7, 10, and 11, respectively) with untreated (FIG. 19A) and OEG SAM-modified glass substrates (FIG. 19B) (as references) in growth medium over an 11-day growth period.
Figure 19B:
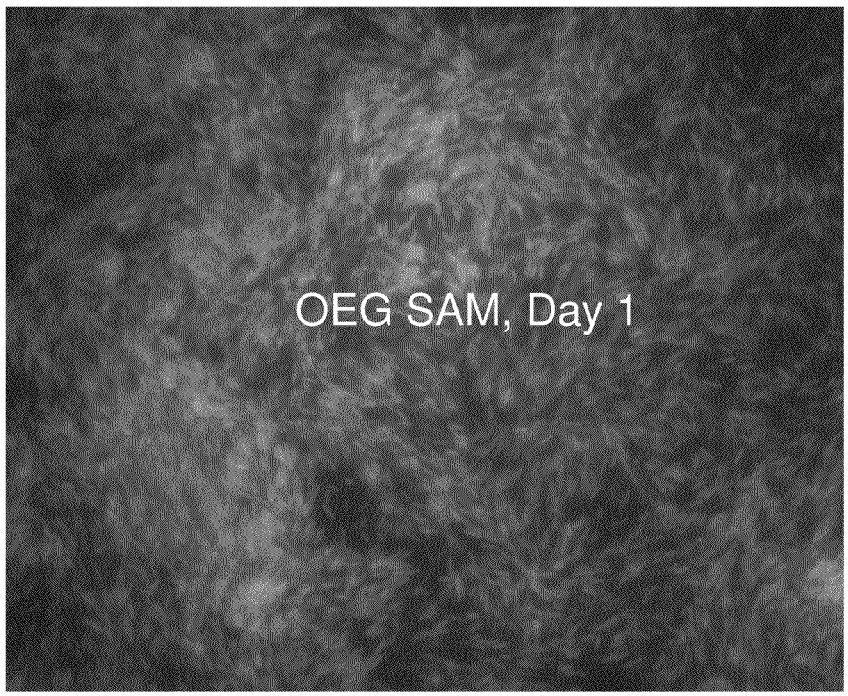
Figure 19C:
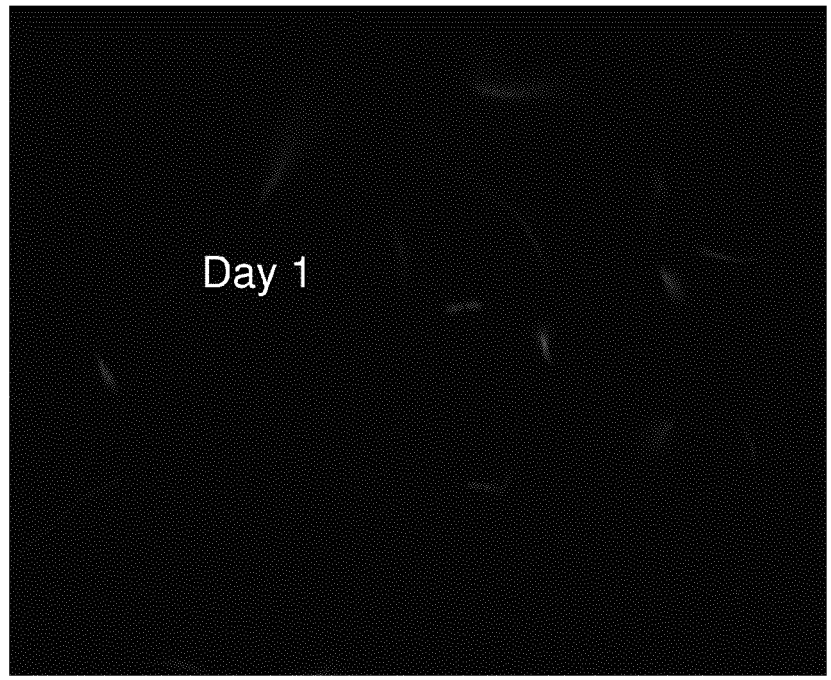
Figure 19D:
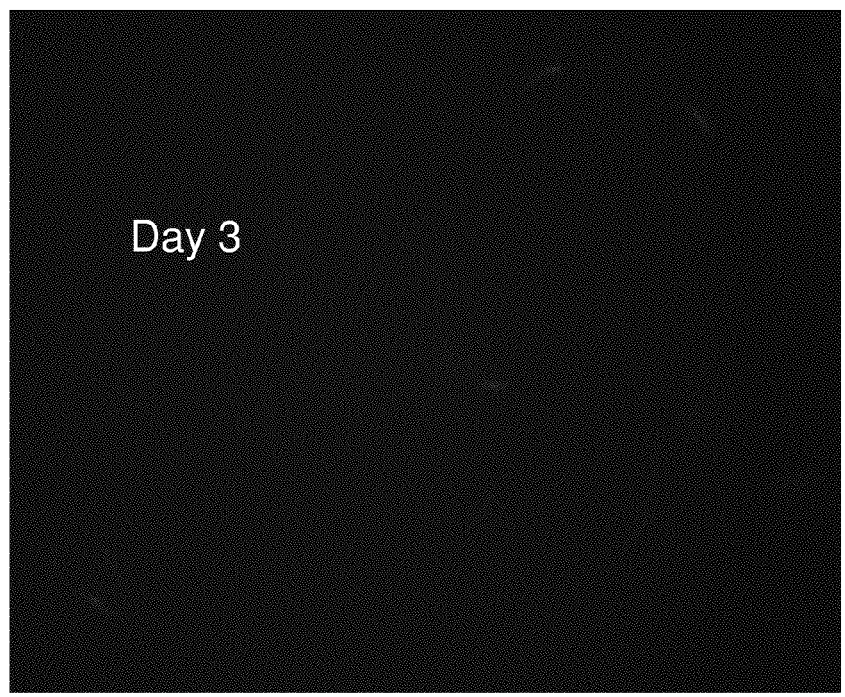
Figure 19E:
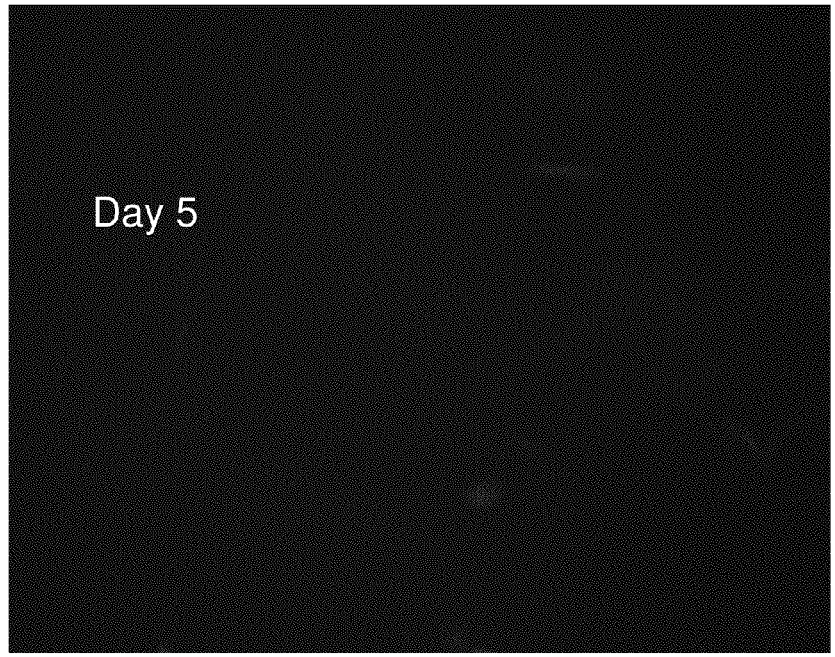
Figure 19F:
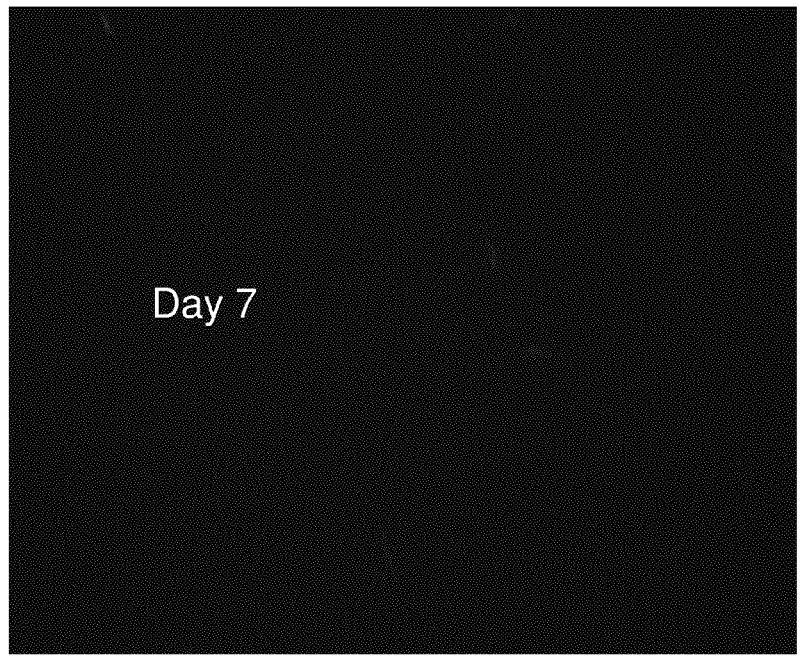
Figure 19G:
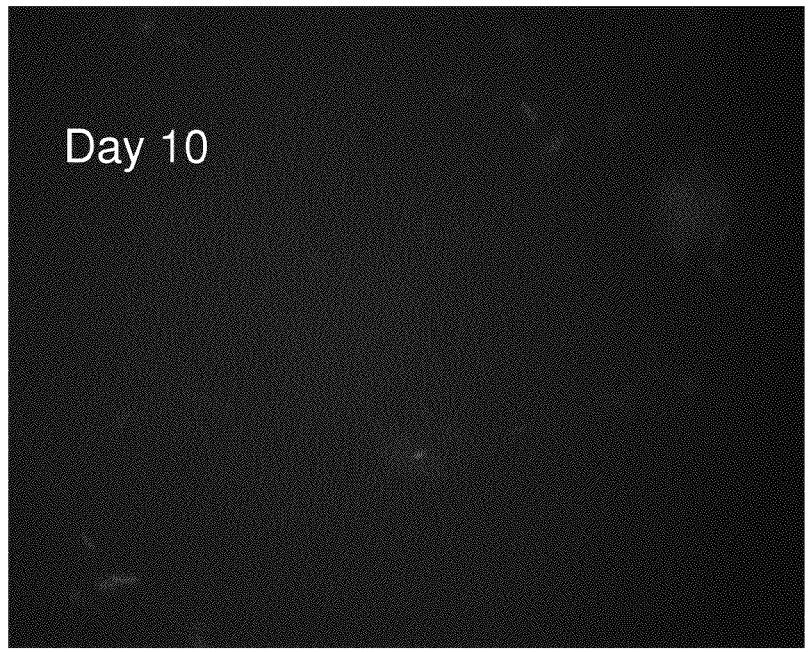
Figure 19H:
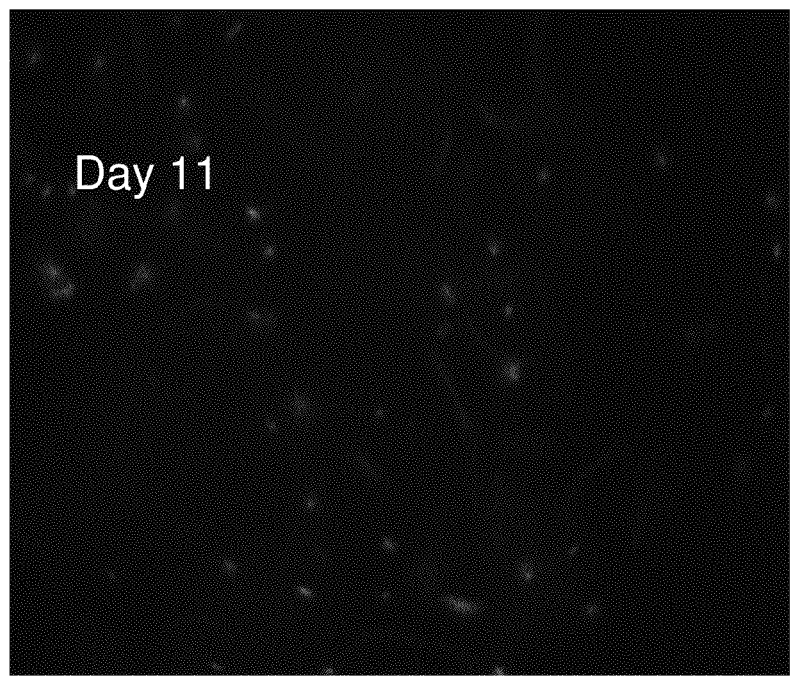

Six representative cationic polymers useful in the invention and SAM modifications were evaluated for their interactions with human serum and plasma. Human serum and plasma are components of human blood, comprised of a complex mixtures of hundreds of proteins. FIGS. 17A and 17B show sensor responses to human serum and human plasma, respectively. pCBMA had the best non-specific resistance to the test media. A pCBMA surface had an improved resistance to nonspecific protein adsorption from human plasma or serum over the poly[oligo(ethylene glycol) methacrylate] (pOEGMA) and poly(sulfobetaine methacrylate) (pSBMA) (See FIGS. 17A and 17B). While protein adsorption from 10% serum is generally low, the difference among several surfaces studied to resist nonspecific protein adsorption from 100% plasma and serum is enormous as shown in FIGS. 17A and 17B. With the optimization of film thickness and density, pCBMA can highly resist 100% blood plasma and serum to the level that is undetectable by SPR (See FIG. 18).

Microbial adhesion and the subsequent formation of biofilm are critical issues for many biomedical applications. Therefore, the development of surfaces that resist the initial adhesion of bacteria is the first step towards the effective prevention of long-term biofilm formation. The accumulation of *P. aeruginosa* on pSBMA modified glass chips formed with a silane initiator and surface-initiated ATRP indicates that pSBMA grafted surfaces show strong resistance to bacterial adhesion and biofilm formation for one day. *Pseudomonas aeruginosa* PAO1 with a GFP expressing plasmid was used for long-term adhesion and biofilm formation studies. There is an absence of attached bacteria after exposure to *P. aeruginosa* for a long period of time, while *P. aeruginosa* is readily attached to the unmodified portion of glass or oligo (ethylene glycol) (OEG) self-assembled monolayer (SAM) modified substrates. These studies were performed in a laminar flow chamber in situ.

FIGS. 19A-19H are representative microscopy images of the accumulated *P. aeruginosa* on pCBMA-treated surfaces in the growth medium over an 11-day growth period. On the bare and OEG-modified glass surfaces, very quick bacterial adhesion and subsequent biofilm formation of *P. aeruginosa* were observed (see FIGS. 19A and 19B, respectively). A confluent biofilm was formed by the second day on these two control surfaces. However, the surface concentration of adherent *P. aeruginosa* on the pCBMA-coated glass was very small ($<<10^6$ cell/mm$^2$). Over the 11-day growth mode experiments, there was no observed biofilm formation (see FIGS. 19C-19H). It is believed that the ability of zwitterionic pCBMA materials to resist protein adsorption and inhibit bacterial adhesion is due to its strong hydration via ionic solvation.

In one embodiment, the wound dressings of the invention include hydrogels containing cationic polymers (zwitterionic precursors) of the invention and zwitterionic polymers.

Dried hydrogels as wound dressings can be prepared in two ways: (1) forming a chemical or IPN gel from zwitterionic monomers (e.g., CBMA) and cationic monomers (e.g., CBMA ester monomers) (a more controllable way) and (2) forming a chemical gel from the cationic monomer (pCB ester monomer) first and then partially hydrolyzing the product hydrogel (e.g., pCBMA ester hydrogel) to mixed cationic and zwitterionic hydrogel (pCBMA ester/pCBMA hydrogel) (a more economic way).

Figure 20:
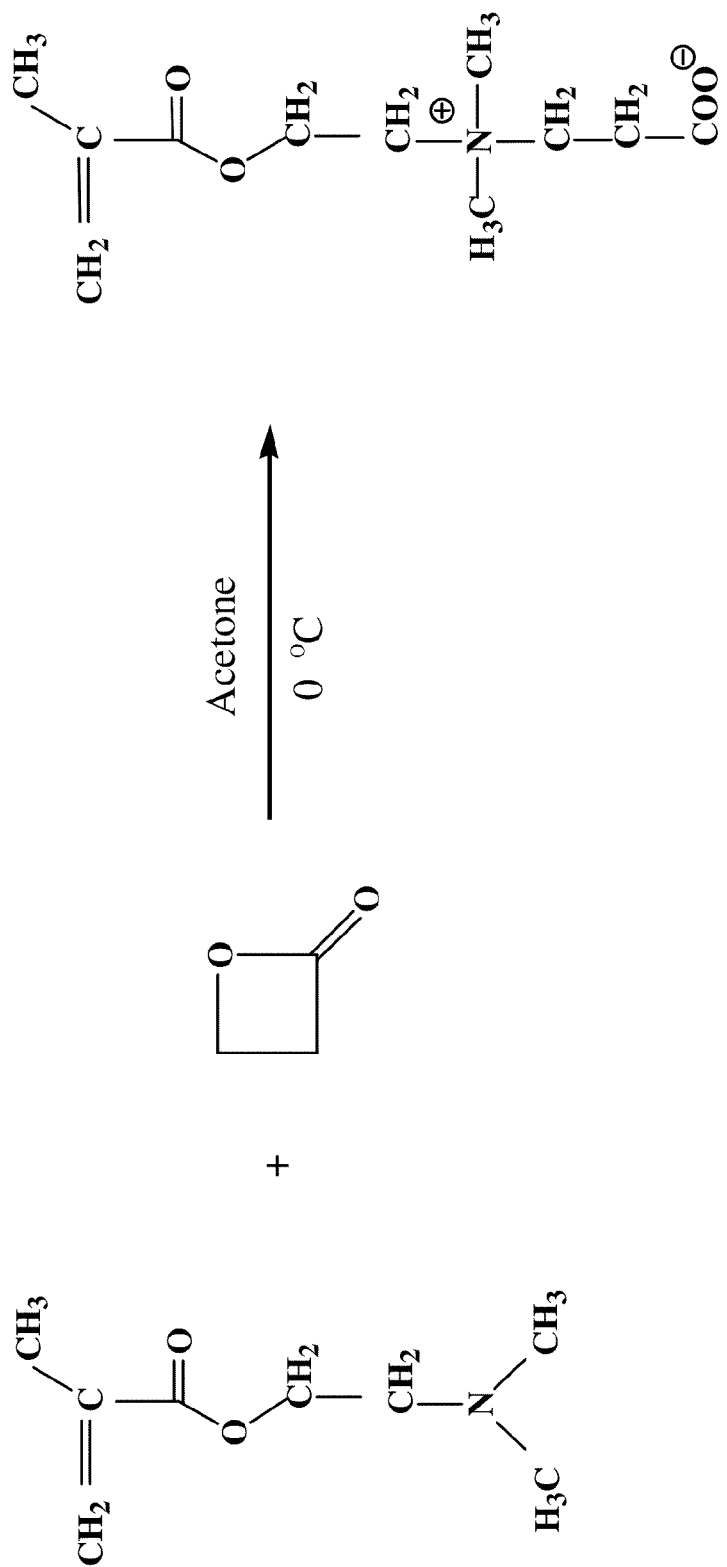
FIG. 20 is a schematic illustration of the preparation of a zwitterionic CBMA monomer.

A representative hydrogel can be prepared from carboxybetaine methacrylate (CBMA) and cationic zwitterionic precursor monomers. CBMA monomer can be synthesized by the reaction of 2-(N,N'-dimethylamino)ethyl methacrylate (DMAEMA) and β-propiolactone with anhydrous acetone as solvent at low temperature (see FIG. 20). The purity (>99%) can be monitored by nuclear magnetic resonance (NMR) and elemental analysis. Alternatively, carboxybetaine acrylamide (CBAA) can be similarly prepared and used. Similar to CBMA, CBAA monomer can be synthesized by the reaction of N-(3-dimethylaminopropyl)acrylamide (DMAPAA) and β-propiolactone with anhydrous acetone as solvent at low temperature.

Figure 21:
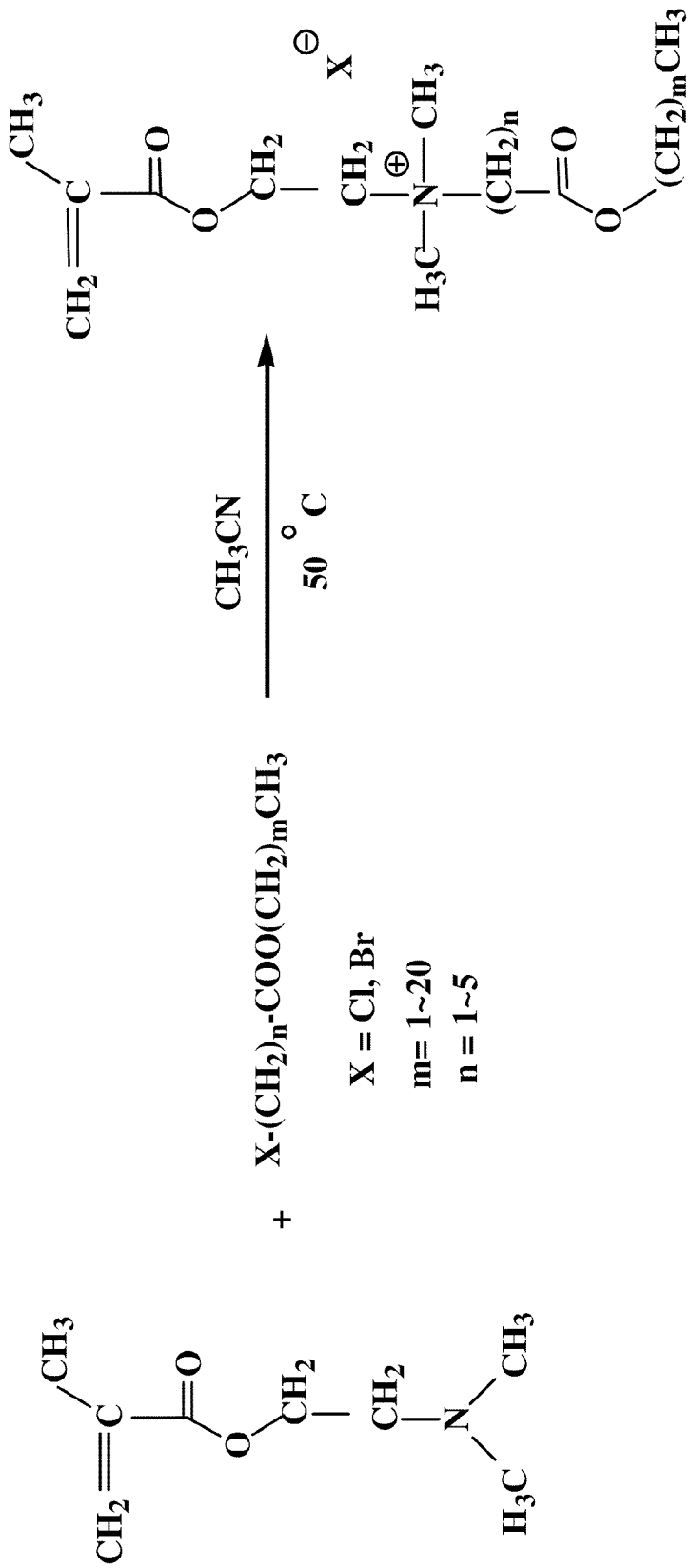
FIG. 21 is a schematic illustration of the preparation of representative cationic polymers useful in the invention, CBMA ester monomers (m=1-20 and n=1-5).

Cationic zwitterionic precursor monomer (i.e., CBMA ester) can be synthesized by quaternization reaction from DMAEMA and alkyl chloro (or bromo) carboxylates using anhydrous acetonitrile as solvent (see FIG. 21).

CBMA was synthesized by DMAEMA and β-propiolactone with anhydrous acetone as solvent at low temperature using ice-bath as cooling method (yield ~90%).

Figure 22:
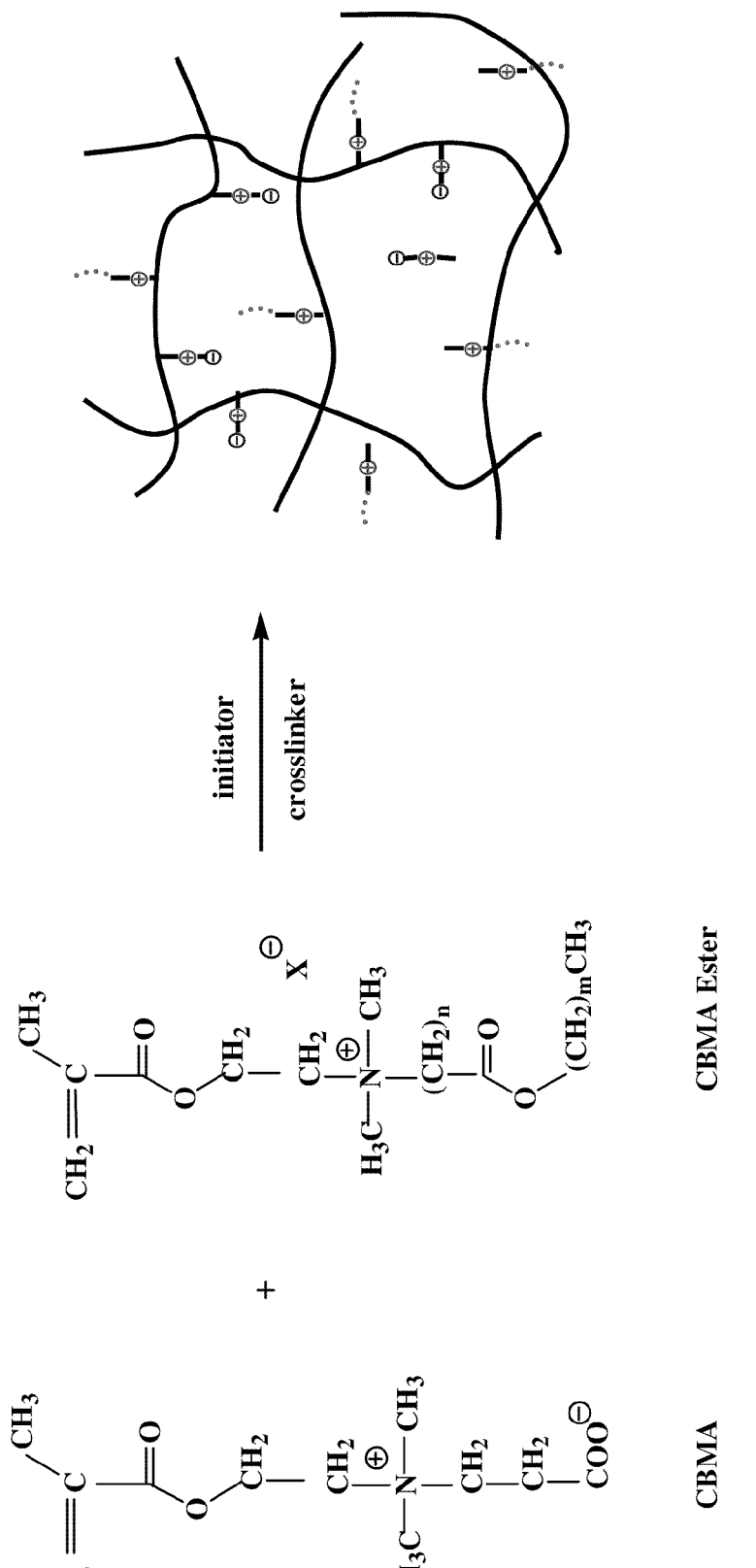
FIG. 22 is a schematic illustration of the preparation of representative hydrogels of the invention from the zwitterionic monomer illustrated in FIG. 20 and the cationic monomer illustrated in FIG. 21: pCBMA ester/pCBMA chemical hydrogels.

Representative hydrogels can be prepared from zwitterionic (e.g., CBMA) and cationic (e.g., CBMA ester) monomers. The polymerization of the monomers is illustrated schematically in FIG. 22. CBMA, CBMA ester and 4 mol % N,N'-methylene-bisacrylamide (MBA, as a cross-linker) are dissolved in deionized water ([M] 10 wt %). To this solution, 0.2 wt % ammonium peroxodisulfate and 1.0 wt % N,N,N', N'-tetramethylethylenediamine (TMEDA, as an accelerator) is added as redox initiators. TMEDA is chosen since it is an initiator for reaction at room temperature. Polymerization is performed at room temperature for 24 hr. After the gelation is completed, the gel is immersed in an excess amount of deionized water for 3 days to remove the residual unreacted monomers. Swollen polymer gels are dried at room temperature for 1 day, and these samples are further dried with freeze drying method or in vacuum oven for 2 days at WC.

Figure 23:
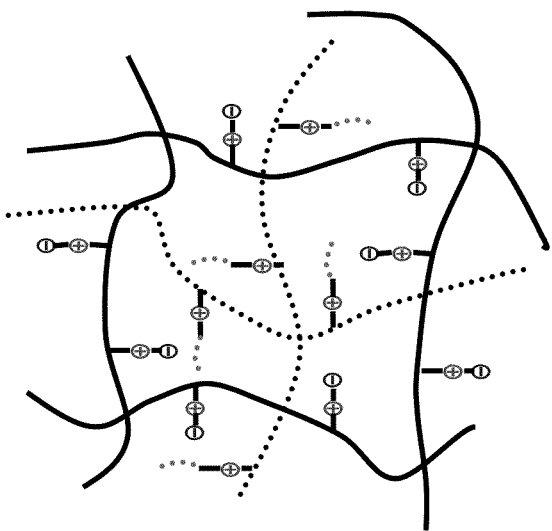
FIG. 23 is a schematic illustration of the preparation of representative IPN hydrogels of the invention from the zwitterionic monomer illustrated in FIG. 20 and the cationic monomer illustrated in FIG. 21: CBMA ester/pCBMA IPN hydrogels.
Figure 23:
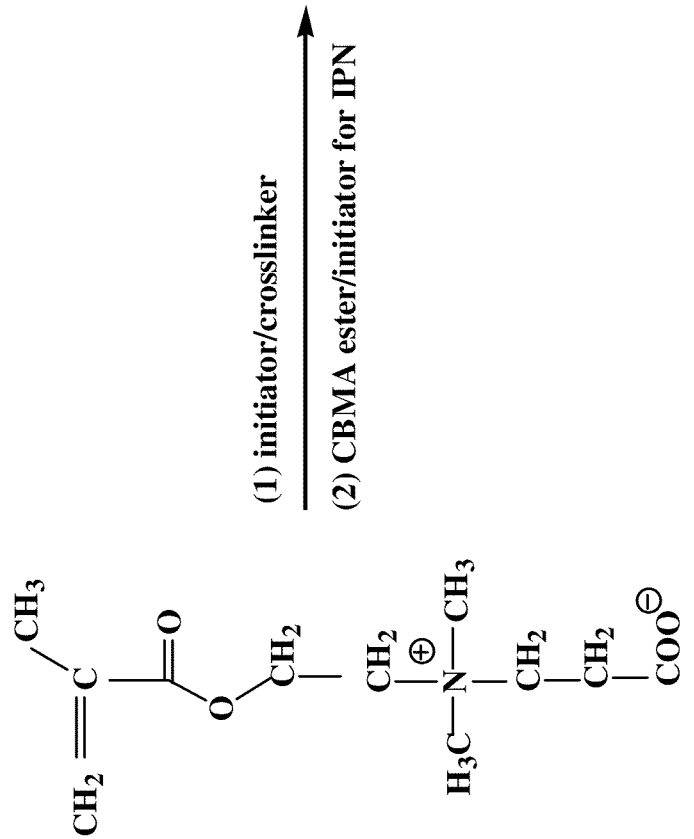

Representative interpenetrating network (IPN) hydrogels can be prepared from zwitterionic (e.g., CBMA) and cationic (e.g., CBMA ester) monomers. The polymerization of the monomers is illustrated schematically in FIG. 23. As a mixture of two or more crosslinked networks that are dispersed or mixed at a molecular segmental level, IPNs can help improve the mechanical strength and resiliency of the polymer gels. An example of the preparation of such an IPN hydrogel is as follows. CBMA and 4 mol % MBA (as a cross-linker) are dissolved in deionized water ([M] 10 wt %). To this solution, 0.2 wt % ammonium peroxodisulfate and 1.0 wt % TMEDA (as an accelerator) are added as redox initiators. Polymerization is performed at room temperature for 24 hr. After the gelation is completed, the gel is immersed in an excess amount of deionized water for 3 days to remove the residual unreacted monomer and initiator. The degree of crosslinking is defined as the molar ratio of the crosslinking agent (MBA) to CBMA.

Representative interpenetrating network (IPN) hydrogels can be prepared from zwitterionic (e.g., pCBMA) and cationic (e.g., pCBMA ester) polymers. pCBMA/pCBMA ester IPN gels are prepared according to the following procedure. A pCBMA gel is immersed in 10 ml of the pCBMA ester monomer solution of the prescribed concentration containing redox initiators mentioned above, and left for 5 days at 4° C. to let pCBMA ester penetrate into pCBMA gel. pCBMA ester inside the pCBMA gel is polymerized at 30° C. for 24 hr to give the IPN gels comprising pCBMA ester linear polymer and pCBMA gel. After the polymerization, the gel is immersed in an excess amount of deionized water for 3 days to remove the residual unreacted monomer and initiator. These samples are dried with freeze drying method or in vacuum oven for 2 days at 60° C.

While the mixed (chemical or IPN) hydrogel from zwitterionic (e.g., CBMA) and cationic (e.g., CBMA ester) monomers can be prepared in a controllable way, it is possible to achieve mixed zwitterionic and cationic hydrogels from a single cationic (e.g., CBMA ester) monomer. This is done by preparing cationic (e.g., pCBMA ester) hydrogel first and then partially hydrolyzing the hydrogel to a mixed cationic/zwitterionic hydrogel (e.g., pCBMA ester/pCBMA).

Hydrophilic cationic (e.g., pCBMA ester) hydrogels can be used as antimicrobial wound dressing once they are partially hydrolyzed. The gels after partial hydrolysis are a mixture of zwitterionic pCBMA and cationic pCBMA ester compounds, which integrates both hemostatic, antimicrobial, and water-adsorbent functions.

Figure 24:
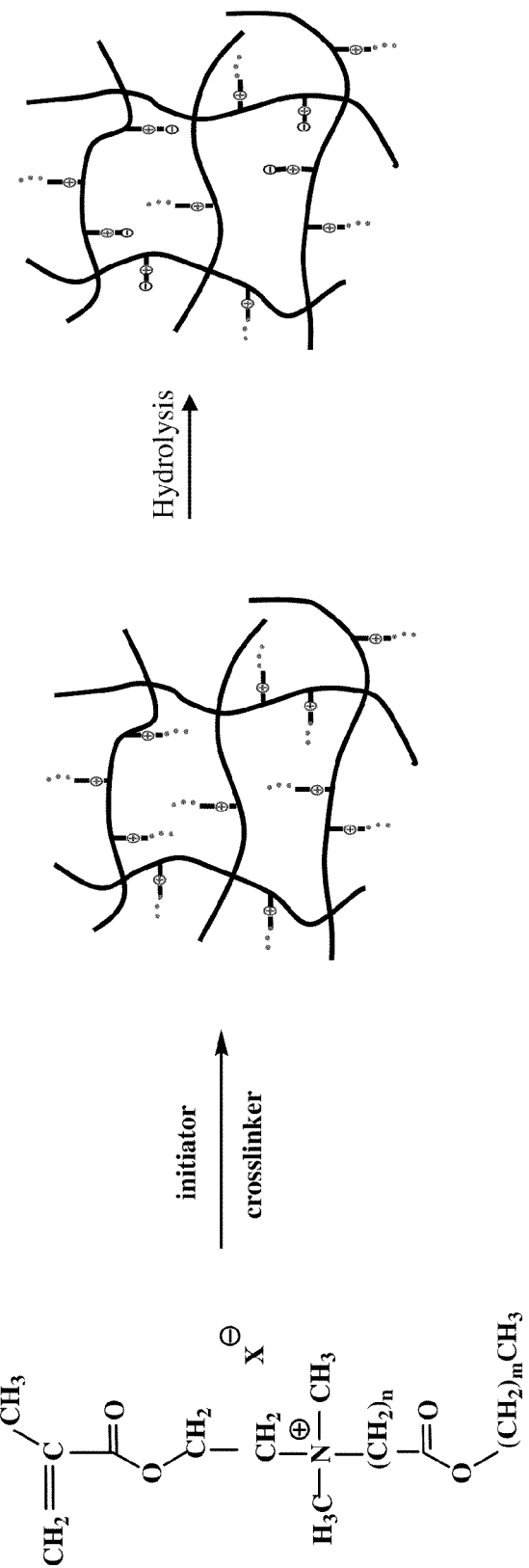
FIG. 24 is a schematic illustration of the preparation of representative hydrogels of the invention from the cationic monomer illustrated in FIG. 21 by partial hydrolysis: partially hydrolyzed pCB ester hydrogels.

A representative procedure for preparing to a partially hydrolyzed cationic (e.g., pCBMA ester) hydrogel is described below and illustrated schematically in FIG. 24. CBMA and 4 mol % MBA as crosslinker) is dissolved in deionized water ([M] 10 wt %). To this solution, 0.2 wt % ammonium peroxodisulfate and 1.0 wt % TMEDA (as an accelerator) are added as redox initiators. Polymerization is performed at room temperature for 24 hr. After the gelation is completed, the gel is immersed in an excess amount of deionized water for 3 days to remove the residual unreacted monomer and initiator. Then, the gel is immersed in the buffer solution (pH 8~12) for 3 to 12 hr, then is washed with deionized water, and immersed in an excess amount deionized water and left for 5 days at 4° C. to remove the residual salts. These samples are dried with freeze drying method or in vacuum oven for 2 days at 60° C.

The hydrogels of the invention prepared as described above can be optimized and evaluated for their antimicrobial, hemostatic, water-adsorbent, and other physical/chemical properties in vitro by adjusting the degree of crosslinking, the ratio of cationic polymer (e.g., pCBMA ester to pCBMA, and hydrolysable groups. Hydrogel pastes are coated onto a polymeric pad to form wound dressing-pad assemblies (or bandages) for in vivo experiments and practical applications. Standard gauze dressing and commercial HC dressing will be used as negative and positive controls whenever is possible.

In one embodiment, the invention provides a wound dressing-pad assembly that includes the wound dressing of the invention. The wound dressing-pad assembly is sized and configured for easy manipulation by the caregiver's fingers and hand. The backing isolates a caregiver's fingers and hand from the dressing gels. The backing permits the dressing matrix to be handled, manipulated, and applied at the tissue site, without adhering or sticking to the caregiver's fingers or hand. The backing can include low-modular meshes and/or films and/or weaves of synthetic and naturally occurring polymers. For temporary external wound applications, the backing includes a fluid impermeable polymer material, e.g., polyethylene (3M 1774T polyethylene foam medical tape, 0.056 cm thick). Other polymers may be used, including cellulose polymers, polyethylene, polypropylene, metallocene polymers, polyurethanes, polyvinylchloride polymers, polyesters, polyamides or their combinations. The backing can be attached or bonded by directed adhesion with a top layer of the wound dressing gel. The dried hydrogel samples can be moistened with 1-3 wt % of sterile physiological saline, which can turn into a sticky paste and have sufficient adhesive properties for attaching to the backing materials. If needed, an adhesive such as 3M 9942 Acrylate Skin Adhesive, or fibrin glue, or cyanoacrylate glue can be employed to enhance the adhesion between the wound dressing and the pad. The wound dressing matrix is desirably vacuum packaged before use with low moisture content, preferably 5% moisture or less, in an air-tight heat sealed foil-lined pouch. The antimicrobial wound dressing pad assembly is subsequently terminally sterilized within the pouch by the use of gamma irradiation. Once removed from the pouch, the wound dressing pad assembly is immediately ready to be adhered to the targeted tissue site. These wound dressings are non-irritating and non-sticky to the wound, absorb wound exudate, enhance the sterile environment around the wound, stem blood loss, and promote wound healing. The wound dressing gels can be removed without leaving any gel residue on the wound due to the nonfouling properties of these wound dressing hydrogels.

Figure 26:
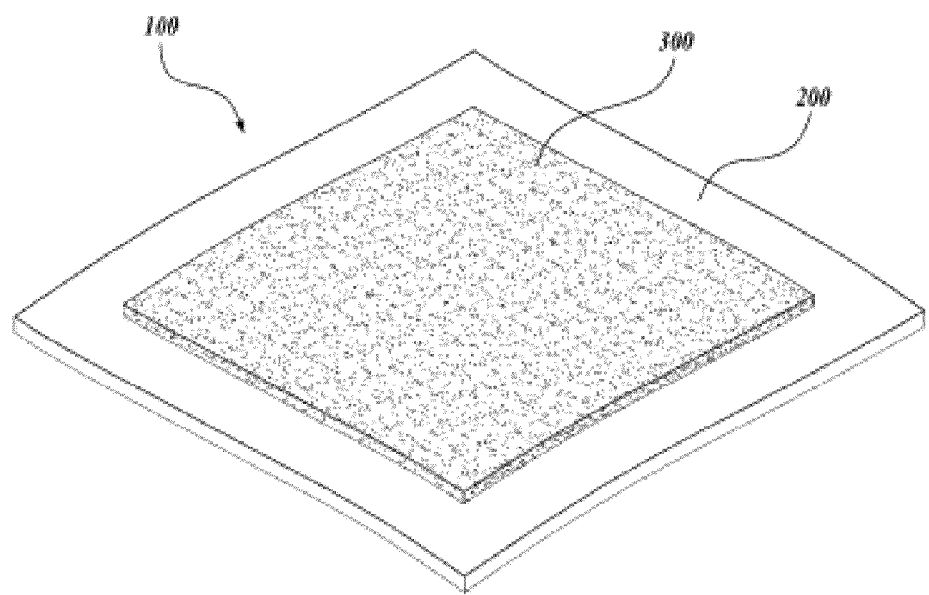
FIG. 26 illustrates a representative wound dressing of the invention.

A representative wound dressing of the invention is illustrated in FIG. 26. Referring to FIG. 26, representative wound dressing 100 includes backing 200 and gel 300.

Figure 25:
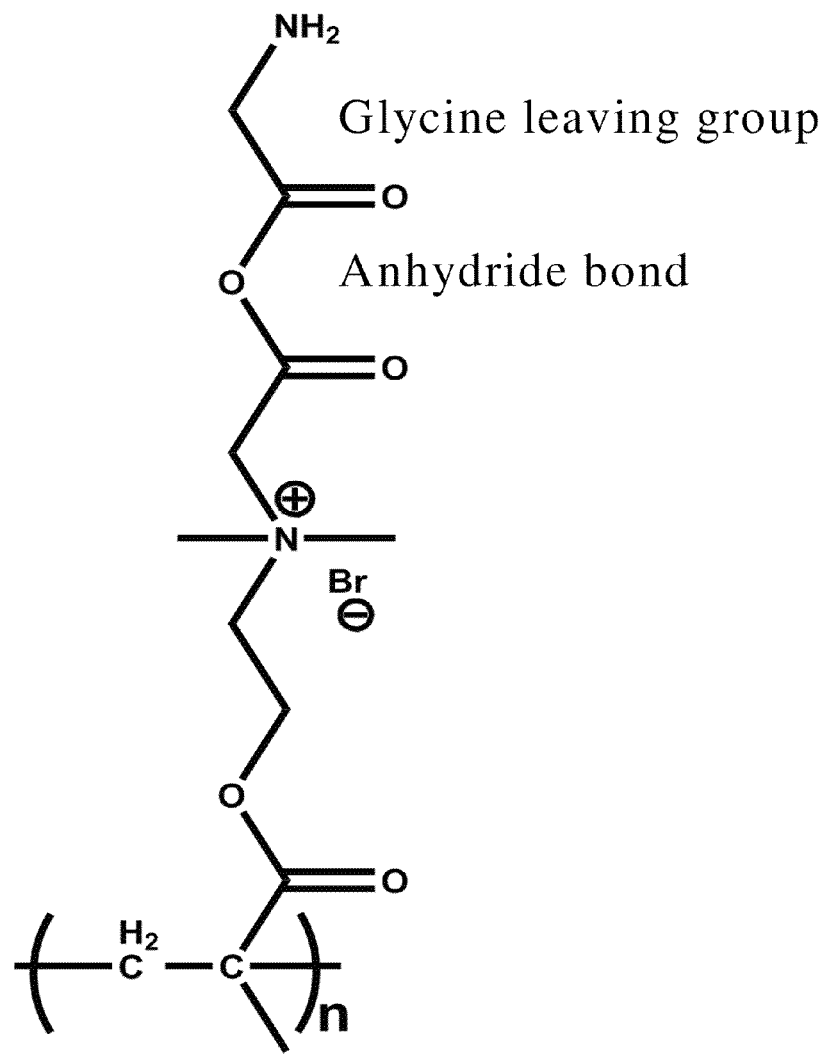
FIG. 25 illustrates the chemical structure of a representative cationic polymer of the invention having a glycine leaving group: pCBMA with a glycine leaving group.

The hydrolysis rate of the cationic polymers (e.g., esters) is influenced by several factors, such as the length of the spacer between the quaternary amine and the carboxyl group, the type of the hydrolyzable group, temperature, and pH. For a representative cationic polymer, pCBMA ester with n=1, the ester is an ethyl ester that produces ethanol on hydrolysis. A limited amount of ethanol will be generated upon hydrolysis, some of which will be trapped within the hydrogel, and some ethanol will be released, but will not affect wound healing. Alternatively, in one embodiment, the cationic polymer has a glycine leaving group (hydrolyzable bond is an anhydride) as illustrated in FIG. 25.

In one aspect, the invention provides a hydrogel prepared from a cationic polymer of the invention. In one embodiment, the hydrogel is a crosslinked hydrogel.

Hydrogel materials have been broadly used as implantable materials, catheters, and wound dressings due to their high water content and excellent biocompatibility. However, controlled release of small hydrophilic drugs from hydrophilic surfaces, such as hydrogel, has proven challenging, because encapsulated drugs are quickly released and depleted through diffusion.

In one embodiment, the hydrogel provide for the sustained release of an antimicrobial agent to inhibit the growth of planktonic bacteria and create a nonfouling surface to prevent protein absorption or bacterial accumulation upon the hydrolysis of the cationic polymers to zwitterionic groups. A representative hydrogel (poly(N,N-dimethyl-N-(ethylcarbonylmethyl)-N-[2-(methacryloyloxy)ethyl]ammonium salicylate hydrogel, referred to herein as pCBMA-1 C2 SA hydrogel) inhibits the growth of both Gram-negative *Escherichia coli* K12 and Gram-positive *Staphylococcus epidermidis* by 99.9%.

The preparation, characterization, and antimicrobial properties of a representative hydrogel of the invention (pCBMA-1 C2 SA hydrogel) is described in Example 5.

Figure 27:
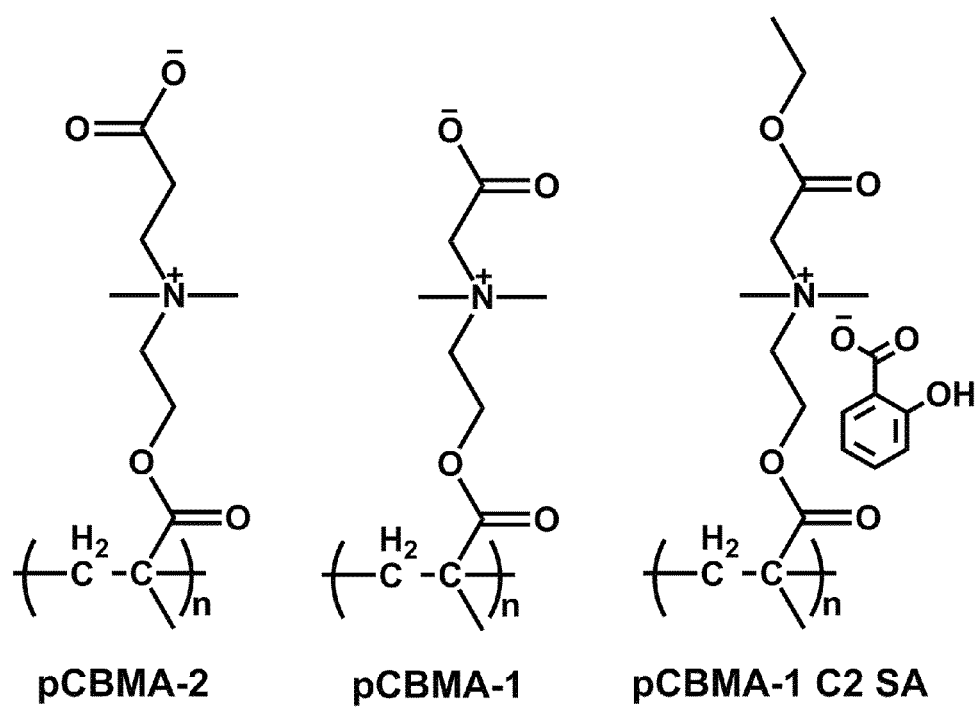
FIG. 27 illustrates the chemical structures of a representative cationic polymer of the invention, switchable pCBMA-1 C2, and pCBMA-1, and pCBMA-2.
Figure 28:
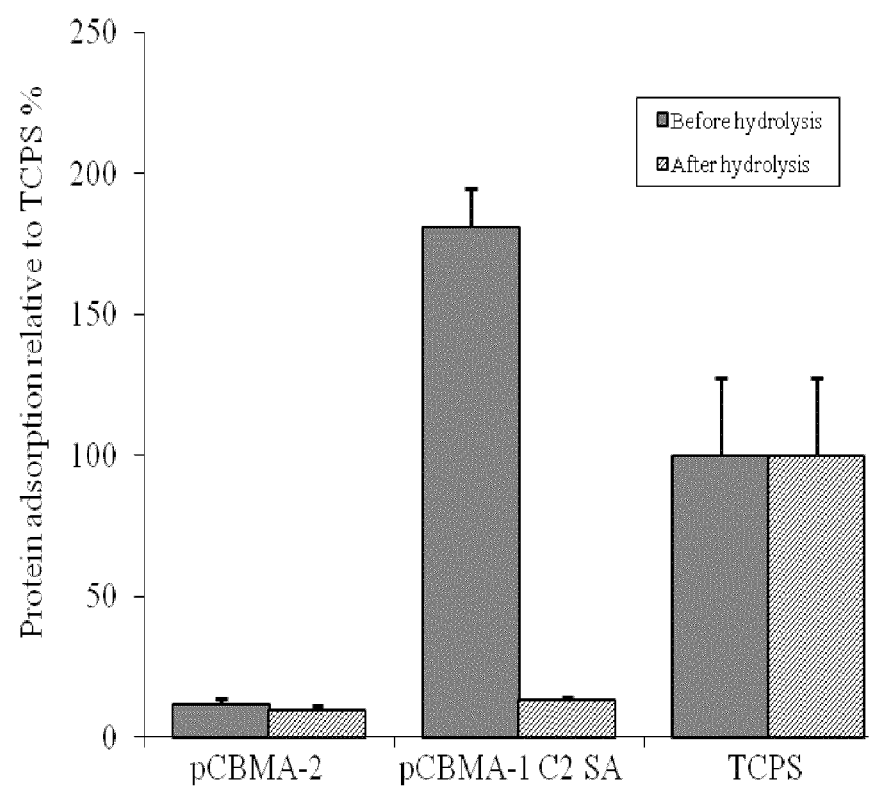
FIG. 28 compares fibrinogen adsorption on the surfaces grafted with polycarboxybetaine esters before and after hydrolysis: pCBMA-2, pCBMA-1 C2 SA, and TCPS. Hydrolysis was performed in CAPS buffer (pH 10.0) at 37° C. for 48 h. Protein adsorption on all surfaces was normalized to tissue culture polystyrene (TCPS). The results are averaged from three replicates.
Figure 29A:
FIGS. 29A-29D are photographs of accumulated $E.$ $coli$ K12 on (29A) pCBMA-2 and (29B) pCBMA-1 C2 SA surfaces, and $S.$ $epidermidis$ on (29C) pCBMA-2 and (29D) pCBMA-1 C2 SA surfaces after culture at 37° C. for 24 hours. These experiments are repeated three times.
Figure 29B:
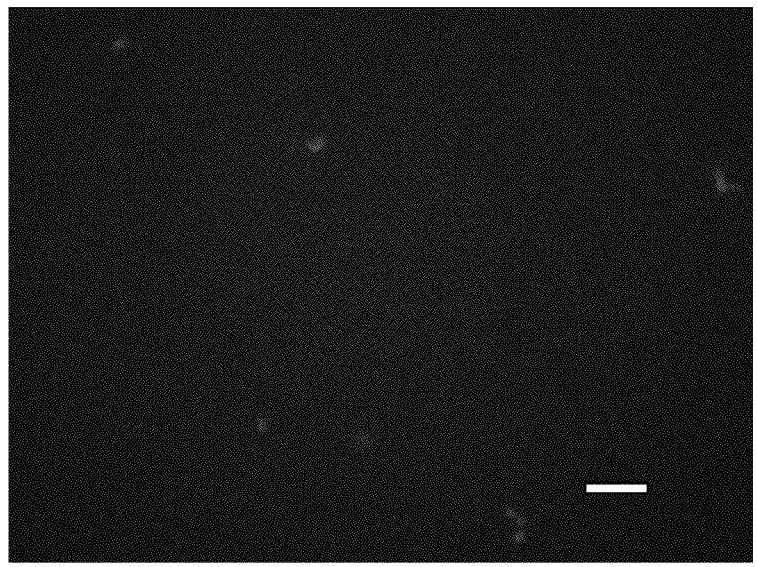
Figure 29C:
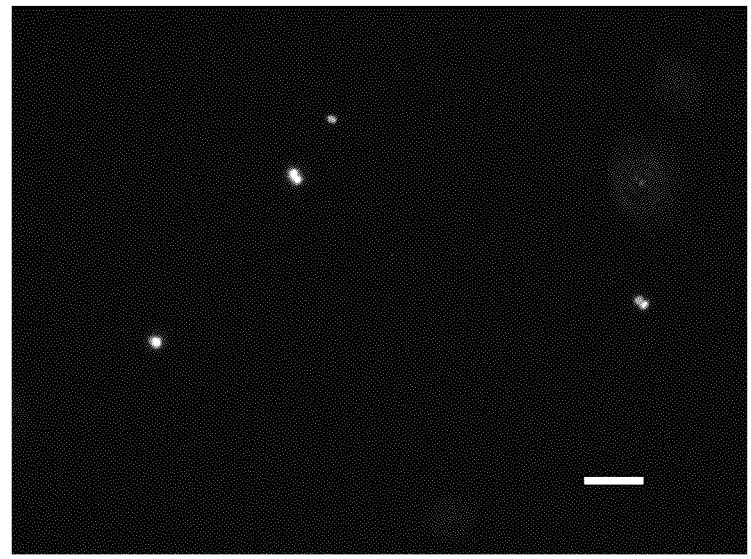
Figure 29D:
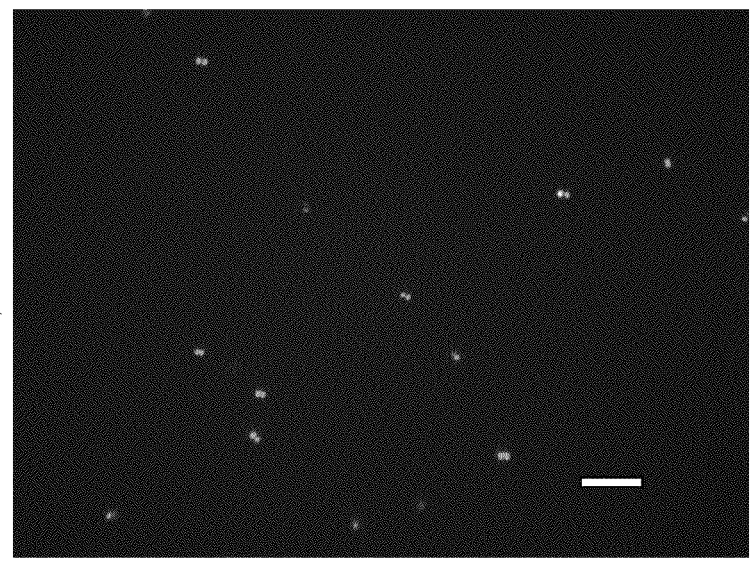

The structures of pCBMA-1, pCBMA-2, and pCBMA-1 C2 SA are shown in FIG. 27. The percentage of water was measured in the tested hydrogels. Zwitterionic pCBMA-2 hydrogel (93.71% water content) showed a lower swelling ratio than pCBMA-1 C2 SA hydrogel (96.57% water content). The lower swelling of the zwitterionic pCBMA-2 hydrogel in water is due to its anti-electrolyte properties. Increasing the solution ionic strength enhances the swelling of zwitterionic hydrogels. Unlike zwitterionic pCBMA-2, the cationic pCBMA-1 C2 SA exhibits polyelectrolyte properties with the higher swelling ratio of pCBMA-1 C2 SA in water. Non-specific protein adsorption on pCBMA-1 C2 SA hydrogels surface was measured by ELISA to determine the non-fouling characteristics of the hydrogel (FIG. 28). pCBMA-1 C2 SA hydrogels were hydrolyzed in N-cyclohexyl-3-aminopropanesulfonic acid (CAPS) buffer (pH 10.0) along with other control hydrogels. Fibrinogen adsorption on pCBMA-1 C2 SA hydrogels before hydrolysis was 180% relative to hydrophobic TCPS due to positively charged quaternary ammonium groups in pCBMA-1 C2 SA hydrogels. After 48-hour hydrolysis, protein adsorption on pCBMA-1 C2 SA hydrogels dropped to 13%, indicating that cationic pCBMA-1 C2 SA hydrogels were hydrolyzed to zwitterionic poly(1-carboxy-N,N-dimethyl-N-(2-methacryloyloxyethyl) methanaminium inner salt) (pCBMA-1). Under identical conditions, pCBMA-2 hydrogels exhibited excellent non-fouling properties with less than 12% protein adsorption at all conditions. After hydrolysis by incubating the surface with CAPS buffer at pH 10 or sodium hydroxide, the pCBMA-1 C2 surface switched to an ultralow fouling surface. However, protein adsorption on surfaces coated the permanently positively charged polymer with a methacrylate polymer backbone was high before and after its incubation with CAPS buffer at pH 10. The result indicated that the hydrolysis occurred on the terminal ester bond instead of the ester bond close to the polymer backbone. These results indicate that the obtained zwitterionic hydrogels effectively resist nonspecific protein adsorption, and are desirable as surface coatings for implantable medical devices. As shown in FIGS. 29A-29D, the accumulation of *S. epidermidis* and *E. coli* K12 on pCBMA-2 and pCBMA-1 C2 SA hydrogel surfaces was observed after 24 hour culture of both strains under static conditions. Although zwitterionic pCBMA-2 hydrogel cannot inhibit the growth of both *E. coli* and *S. epidermidis* in growth medium, the surface of pCBMA-2 hydrogels showed the low accumulation of bacterial cells due to its excellent non-fouling properties.

Figure 30A:
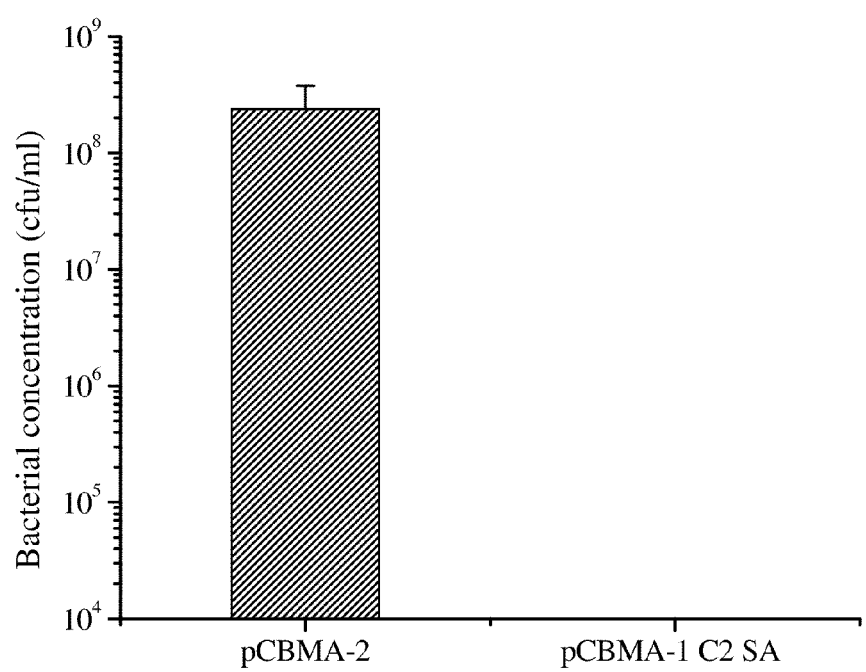
FIGS. 30A and 30B compare growth inhibition of pCBMA-1 C2 SA hydrogel against (30A) $E.$ $coli$ K12 and (30B) $S.$ $epidermidis$. Zwitterionic pCBMA-2 hydrogel with no salicylate was used as a control material. After culture at 37° C. for 24 hours, the concentrations of live bacteria in solutions with pCBMA-1 C2 SA hydrogel or pCBMA-2 hydrogel were measured by colony counting. The results are averaged from three replicates.
Figure 30B:
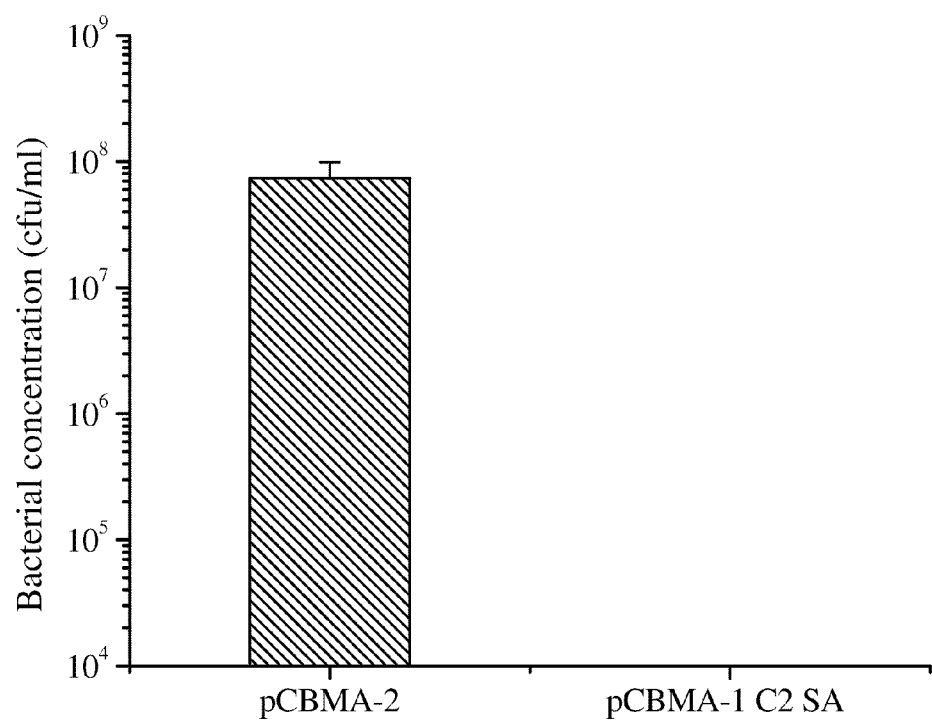

The antibacterial activities of pCBMA-1 C2 SA were evaluated against Gram-negative *E. coli* K12 and Gram-positive *S. epidermidis*. FIGS. 30A and 30B show that the growth of planktonic *E. coli* and *S. epidermidis* was inhibited by the presence of pCBMA-1 C2 SA hydrogel, but not by the presence of pCBMA-2. After 24 hour culture, the concentrations of *E. coli* K12 in the growth medium over pCBMA-2 and pCBMA-1 C2 SA hydrogels were $2.36 \times 10^8$ and below $10^4$ cfu/mL, respectively. Similarly, the concentrations of *S. epidermidis* in the growth medium over pCBMA-2 and pCBMA-1 C2 SA were $7.38 \times 10^7$ and below $10^4$ cfu/mL, respectively.

Salicylic acid is a naturally occurring compound and is produced by many plants to protect against the invasion of bacteria and fungi. Salicylic acid and its derivatives have been broadly used as non-steroidal anti-inflammatory drugs (NSAIDs), because these compounds are able to inhibit the inflammatory response of the body. Salicylate and other NSAIDs are also showed to be able to prevent bacterial adhesion onto medical devices, although the mechanism has not been identified. It has been reported that a low concentration of salicylic acid interferes biofilm formation, and salicylic acid inhibits the growth of *P. aeruginosa* at a high concentration. Salicylic acid has a global effect on the gene expression of *P. aeruginosa*. It interferes with the expression of over three hundred genes. Currently, the long-term administration of antibiotics is being limited due to the danger of generating drug-resistant strains. Unlike antibiotics, the possibility to generating microbial resistance to salicylic acid is small.

In one aspect, the invention provides an antimicrobial hydrogel integrating antimicrobial and non-fouling/biocompatible properties. A representative antimicrobial agent (salicylate) was incorporated into the hydrogel as its anionic counterion. Upon the hydrolysis of carboxybetaine esters to zwitterionic groups, the controlled release of salicylate was achieved and the resulting surface was non-fouling. The hydrogel not only inhibited the growth of planktonic bacteria, but also reduced bacterial adhesion. Through the use of an antimicrobial agent, the hydrogel can also promote wound healing and reduce inflammation. The switchable process and drug release profile from this antimicrobial-to-nonfouling surface can be tuned by adjusting the hydrolysis rate of these polymers for specific requirements of applications.

In another aspect, the invention provides a thermoresponsive hydrogel. In one embodiment, the thermoresponsive hydrogel is prepared from a ABA triblock copolymer. In the triblock copolymer, inner block B is a zwitterionic or cationic polymer flanked by thermo-responsive blocks.

Representative triblock copolymers of the invention have the formula A-B-A, wherein A is a thermoresponsive and B is a cationic polymer of the invention as described above.

In one embodiment, the triblock copolymer has formula (VIII):

$$PB-(L_1-N^+(R_a)(R_b)-L_2-A(=O)-OR_c)_n(X^-)_n \qquad (VIII).$$

In another embodiment, the triblock copolymer has formula (IX):

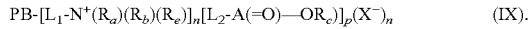

$$PB-[L_1-N^+(R_a)(R_b)(R_e)]_n[L_2-A(=O)-OR_c)]_p(X^-)_n \qquad (IX).$$

In formulas (VIII) and (IX), PB, $L_1$, $N^+$, $R_a$, $R_b$, $R_e$, $L_2$, $A(=O)$—$OR_c$, $X^-$, n and p are as described above for the cationic polymers. In formulas (VIII) and (IX), PB is the polymer backbone and, in the schematic representation, includes flanking thermoresponsive polymers: A-PB-A.

Figure 36:
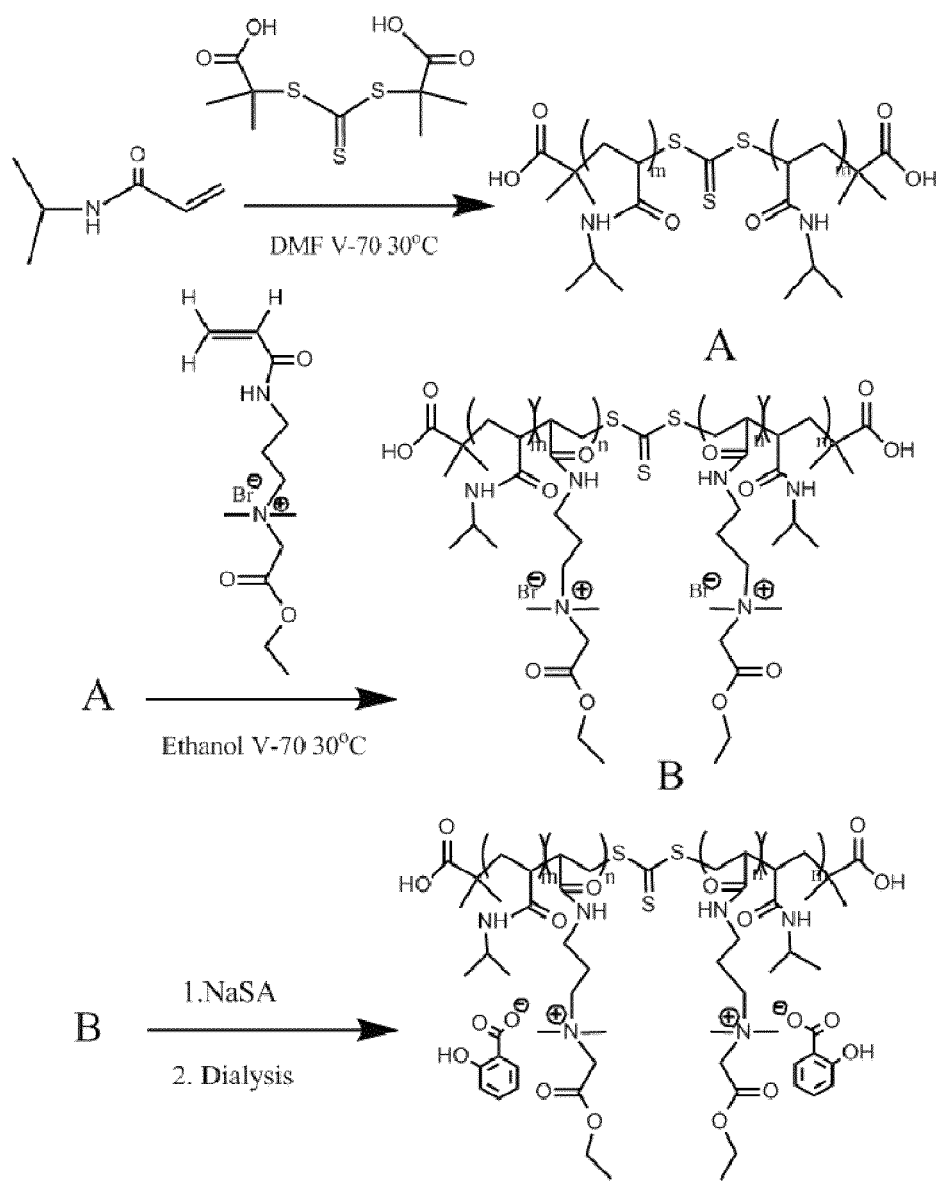
FIG. 36 is a schematic illustration of the preparation of a representative triblock copolymer of the invention.

FIG. 36 is a schematic illustration of the preparation of a representative triblock copolymer of the invention.

The nature of the thermoresponsive polymer is not critical. Suitable thermoresponsive polymers include those known in the art. Representative thermoresponsive polymers include poly(N-alkylacrylamides), poly(methyl vinyl ethers), poly(N-vinyl caprolactams), poly(N-ethyl oxazolines), elastin-like oligo- and polypeptides, poly(acrylic acid-co-acrylamides). Suitable thermoresponsive polymers have degrees of polymerization (DP) sufficient to render the triblock copolymer a liquid below physiological temperature (e.g., human body temperature) and a gel at physiological temperature. In one embodiment, the DP value is from 5 to 10,000. In another embodiment, the DP value is from 100 to 1000.

A representative ABA triblock copolymer was prepared by reversible addition fragmentation chain transfer (RAFT) polymerization. The inner B block was poly(N-1-(ethoxycarbonylmethyl)-N-(3-acryloylamino-propyl)-N,N-dimethyl ammonium salicylate) (PCBAA-C2 SA) flanked by thermoresponsive poly(N-isopropylacrylamide)(PNIPAM). The triblock copolymer aqueous solution remains liquid at ambient temperature and immediately forms physical hydrogel once heated to physiological temperature at 37° C. The salicylate counterion released from the hydrogel inhibits bacteria E. coli K12 growth in 12 h, while, at the same dosage, does not observably affect mammalian COS-7 cell metabolism. The drug release profile and fibroblast cell adhesion property of the hydrogel were also characterized. The in situ formation and antimicrobial feature of the hydrogel renders the hydrogel useful for wound dressing applications.

PNIPAM has a LCST close to human physical temperature. Above its LCST, PNIPAM quickly turns from water soluble to insoluble in a narrow temperature range enabling the block copolymer solution to immediately form a hydrogel at human physical temperature through physical crosslinking. The inner hydrophilic block PCBAA-C2 SA can release salicylate as a mild antimicrobial counter ion, while the cationic polymer backbone is designed to promote negatively charged fibronectin adsorption and thus, in turn, accelerate fibroblast cell adhesion and re-epithelialization. PNIPAM LCST is known to vary as a result of copolymerization with a second monomer. For this reason the phase transition temperature of block copolymers with different monomer composition are measured using dynamic light scattering (DLS). The antimicrobial activity and biocompatibility of the hydrogel after phase transition are characterized with E. coli K12 growth inhibition assay and mammalian COS-7 cell MTT assay, respectively.

The preparation, characterization, and properties of a representative triblock copolymer is described in Example 6.

ABA triblock copolymer was synthesized via a two-step RAFT polymerization utilizing a difunctional CTA. The GPC result using DMF as solvent showed low PDI and control over DP for the PNIPAM first block (Table 2).

TABLE 2

Polymer DP and PDI

| Polymer | Designed Polymer Structure | Exp. Determined Polymer Structure | PDI |
|---|---|---|---|
| pNIPAM I | (NIPAM) 200 | (NIPAM) 218 | 1.06 |
| pNIPAM II | (NIPAM) 400 | (NIPAM) 454 | 1.06 |
| Triblock I | (NIPAM) 100 (CBAA) 200 (NIPAM) 100 | (NIPAM) 109 (CBAA) 214 (NIPAM) 109 | * |
| Triblock II | (NIPAM)$_{200}$ (CBAA)$_{100}$ (NIPAM)$_{200}$ | (NIPAM)$_{227}$ (CBAA)$_{121}$ (NIPAM)$_{227}$ | * |

The DP for the second block (PCBAA-1 C2 Br) was calculated based on NMR characteristic peak comparison and agrees well with the theoretical molecular weight. Unfortunately, the triblock copolymer after extension aggregates in DMF as indicated by a more than two orders of magnitude increase in MW compared to the theoretical MW. For this reason, an aqueous phase GPC system with a relatively high ionic strength eluent was used to verify that the macro CTA can reinitiate the second step polymerization.

Salicylic acid (SA) counter ion is found to severely interfere with the living polymerization system used. To counter for this, the SA was incorporated into the polymer as a counter ion through ion exchange with excess NaSA after the polymerization process. The replacement of Br$^-$ with SA$^-$ was followed by dialysis against MiniQ water at 4° C. to remove any excessive SA$^-$ or NaSA. The NMR result after dialysis showed a 1:1 ratio between SA$^-$ and CBAA-1 C2 in the final polymer.

Figure 31A:
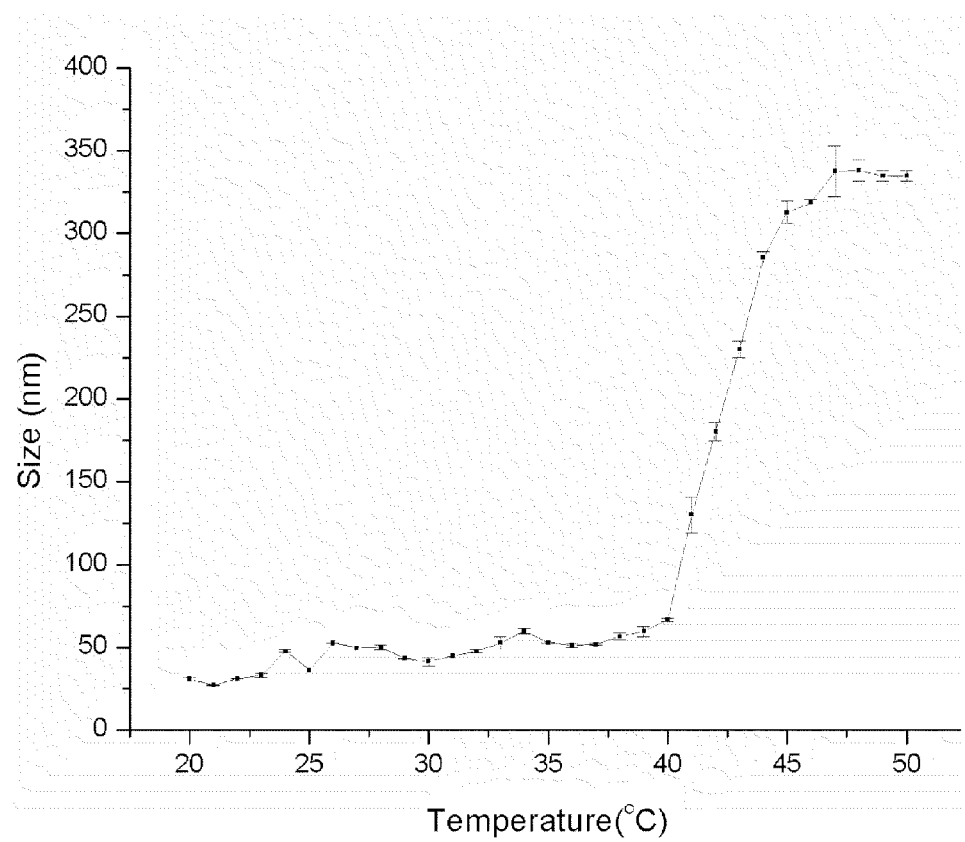
FIGS. 31A-31C compares the hydrodynamic radius of 0.1 wt % representative copolymers of the invention, Triblock I (31A) and Triblock II (31B), to control pNIPAM (31C) in water as temperature increases from 20° C. to 50° C.
Figure 31B:
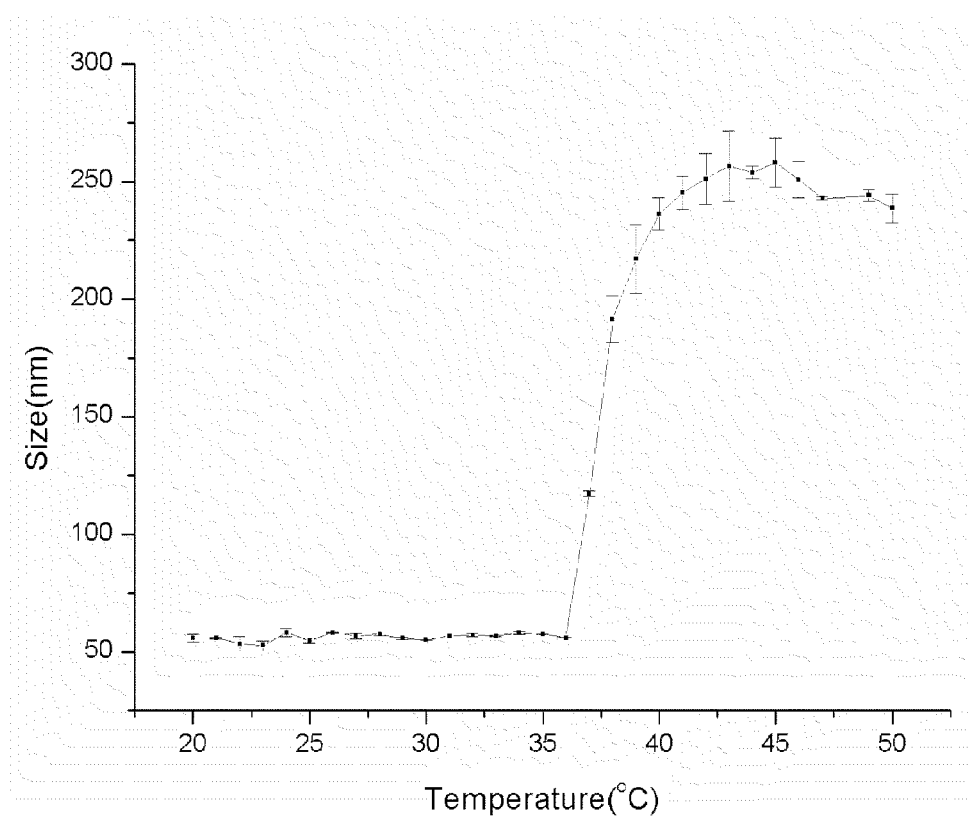
Figure 31C:
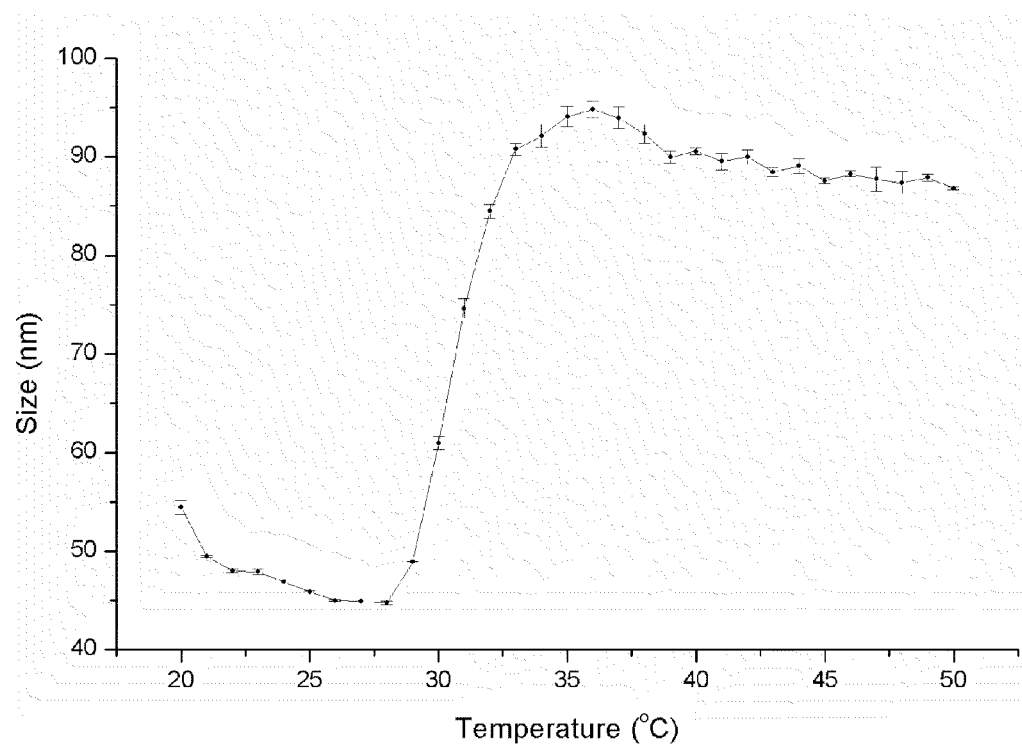

Previous studies have reported that copolymerization of NIPAM with other monomers can cause a significant shift of the original LCST of pNIPAM homopolymer at 32° C. DLS was used to monitor the copolymer phase transition behavior in water with varying composition of hydrophilic and hydrophobic blocks as well as pNIPAM homopolymer. The result (FIGS. 31A-31C) shows that the phase transition temperature (marked by the sudden increase in the particle size caused by aggregation) for Triblock I [(NIPAM)$_{109}$(CBAA-1 C2 SA)$_{214}$ (NIPAM)$_{109}$], Triblock II [(NIPAM)$_{227}$(CBAA-1 C2 SA)$_{121}$ (NIPAM)$_{227}$], and pNIPAM [(NIPAM)$_{218}$] were 41° C., 37° C., and 30° C., respectively.

The phase transition of polymer alone does not guarantee the formation of a physical hydrogel. The hydrophobic domain of the polymer is required to hold a sufficiently strong physical network and the hydrophilic domain is required to bind water to prevent phase separation from occurring. Direct gelation was evaluated at 37° C. for Triblock I, Triblock II, and pNIPAM and results are summarized in Table 3.

TABLE 3

Gelation property of polymers at 37° C. with different concentrations

| Polymer | 5% (w/v) | 10% (w/v) | 20% (w/v) |
|---|---|---|---|
| Triblock I* | No Gel Forming | No Gel Forming | No Gel Forming |
| Triblock II | No Gel Forming | Gelation | Gelation |
| PNIPAM** | Gelation | Gelation | Gelation |

Despite similar DP (about 500), Triblock I and Triblock II have different gelation behaviors. Triblock I does not have sufficient physical crosslinking even heated well above it's LCST. In contrast, pNIPAM forms a gel at 5% weight concentration, a phase separation follows within an hour owing to the pure hydrophobic nature of the homopolymer. Among the three, Triblock II is able to form physically free standing hydrogel at 10 and 20 wt % and remains stable after prolonged incubation at 37° C.

Figure 32:
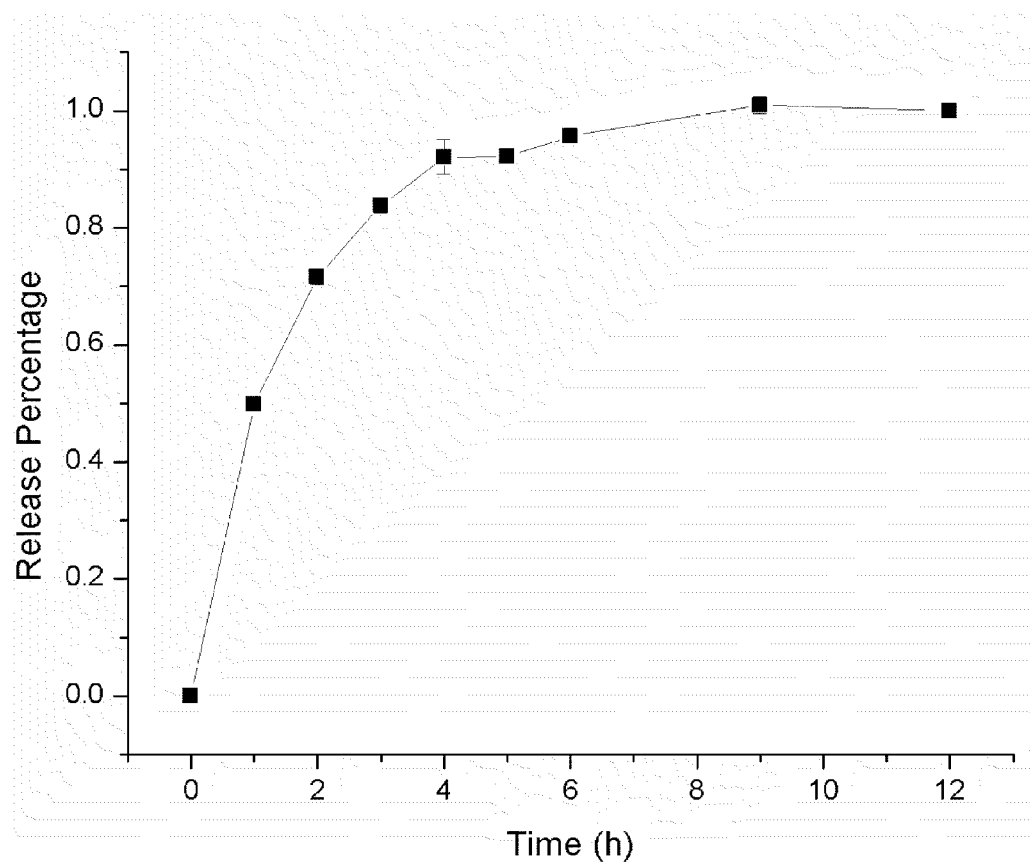
FIG. 32 illustrates salicylate release profile of a representative copolymer of the invention, Triblock II (20 wt %) hydrogel disc in 37° C. PBS from reverse phase HPLC.

FIG. 32 illustrates the release profile of SA$^-$ from the 20 wt % Triblock II hydrogel in PBS at 37° C. A burst release was observed in the first hour releasing 50% of the total SA$^-$ to the environment. The remaining antibiotic was then released in the next 5 hours at a reduced rate. As salicylate is a mild antibiotic, the initial quick release ensures it's antimicrobial effectiveness and serves well for the purpose of sterilizing the wound site.

Figure 33:
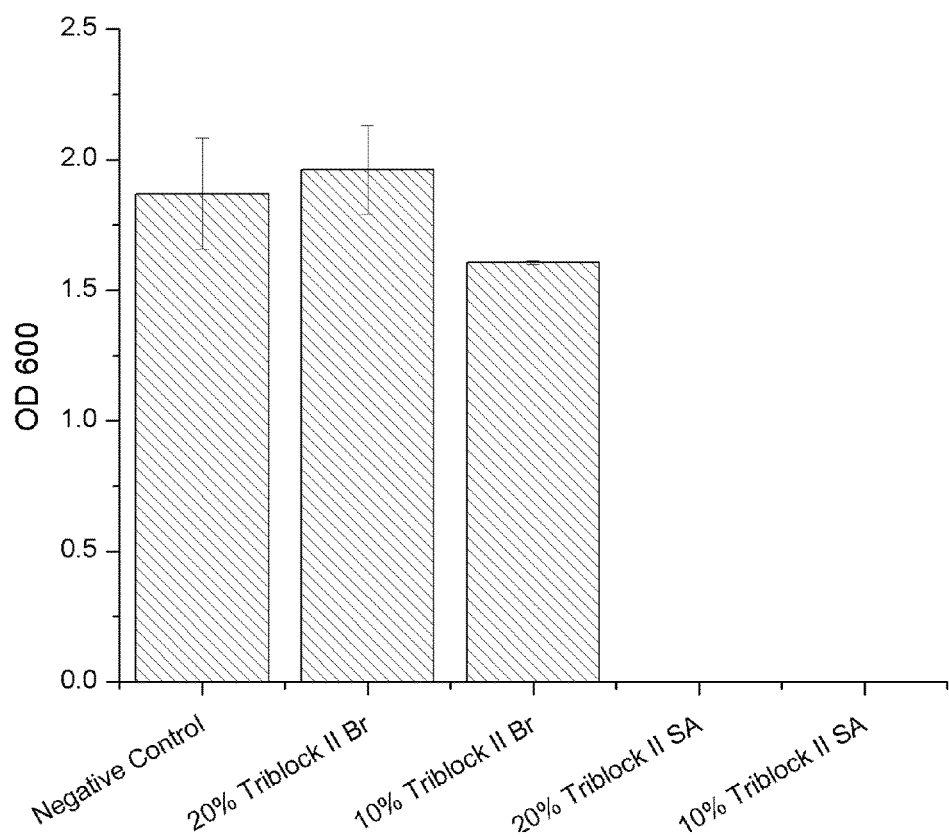
FIG. 33 compares $OD_{600}$ of $E.$ $coli$ K12 inoculated LB liquid media after 12 h co-incubation of a representative hydrogel of the invention (Triblock II SA) to controls (Negative and Triblock II Br).

One critical property for any wound dressing hydrogel is its biocidal or biostatic activity so as to reduce the risk of bacteria colonization and wound infection. A bacteria growth inhibition assay was devised to evaluate the hydrogel's actual antimicrobial activity using gram negative *E. coli* K12 strain as a model. Triblock II hydrogel having salicylic acid as the counter ion completely inhibits the bacteria growth, while bromine ion has no observable effect as compared to negative control (see FIG. 33), indicating the bulk antimicrobial activity is exclusively from the releasing of salicylate.

Figure 34:
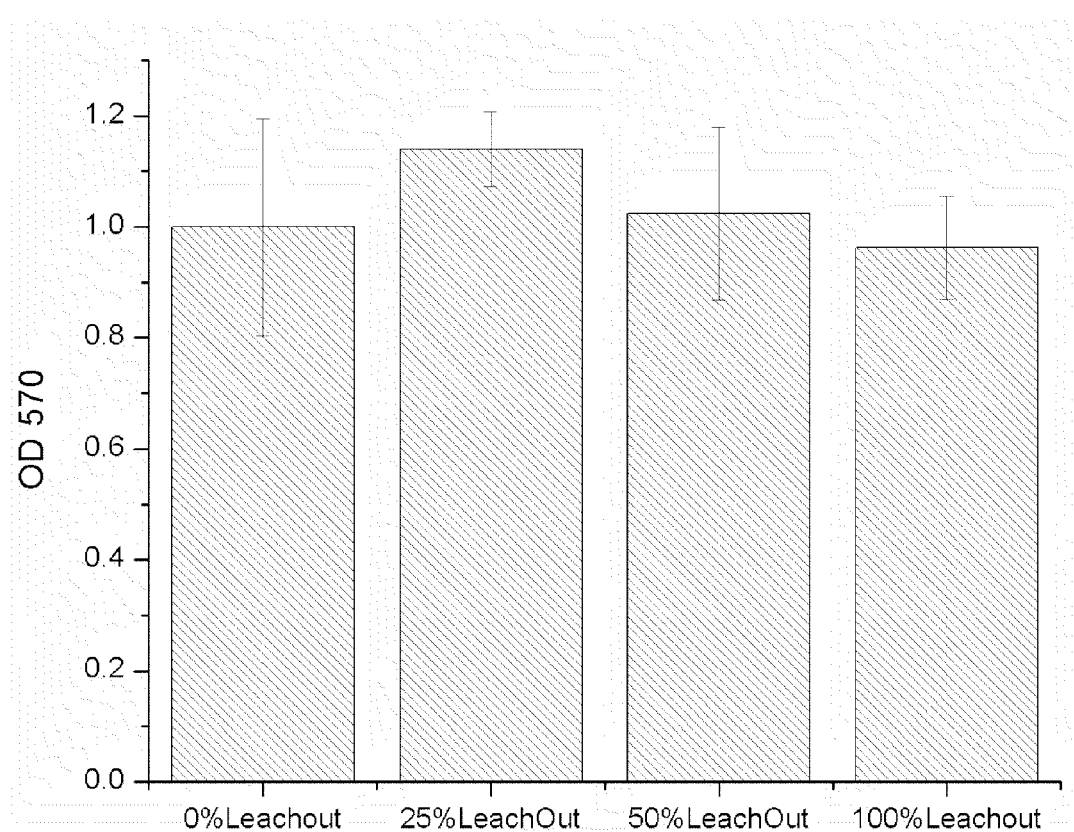
FIG. 34 compares cytotoxicity of a representative hydrogel of the invention (Triblock II SA) leach-out on COS-7 cell as determined by MTT assay.

A major concern with the use of antibiotics in biomaterials is its biocompatibility with mammalian cells. An MTT assay was used to determine the cytotoxicity of Triblock II on mammalian fibroblast cell line COS-7. As MTT is a colorimetry based assay, it is likely that hydrogel can absorb chromophore formed in the assay causing inaccuracy during plate reading. To prevent this problem, a leach out method was used in which leach out of 20% Triblock II hydrogel (with SA$^-$) in phenol-red-free cell culture media was used, diluted to 100%, 50%, and 25% solution for test. The relative hydrogel dosage for 100% leach out is the same as used in bacteria growth inhibition assay. Results (FIG. 34) show that no cytotoxicity was observed for hydrogel leach out at all three concentration tested.

Figure 35:
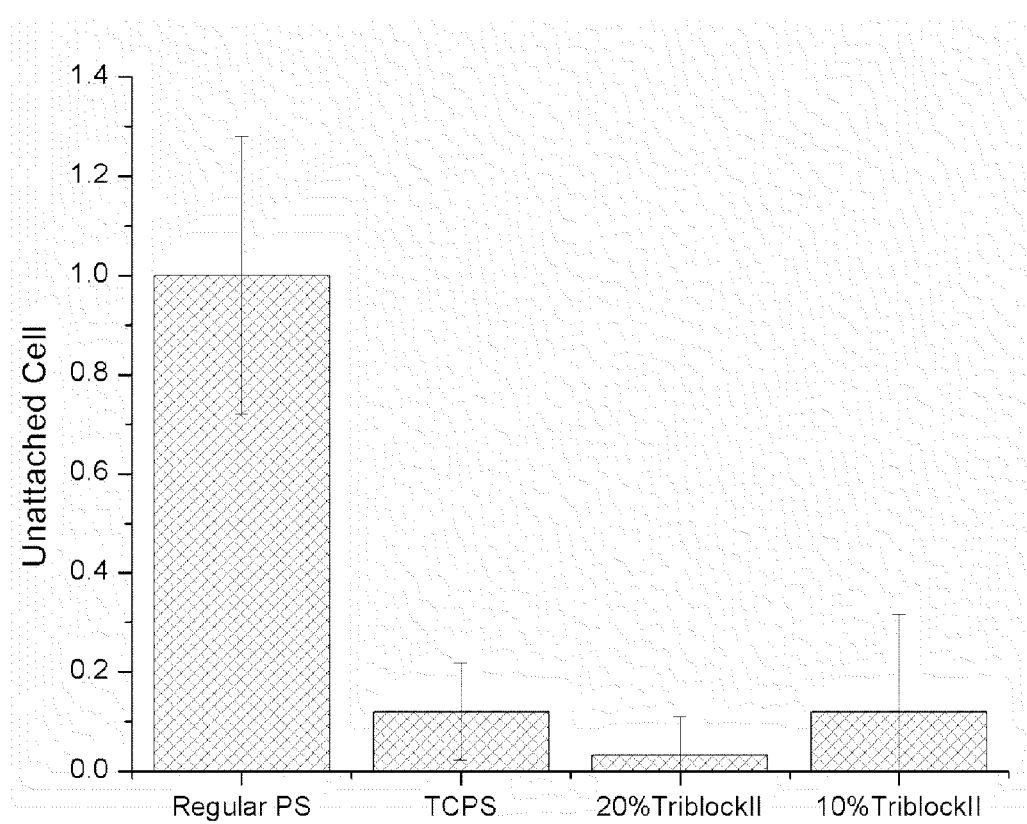
FIG. 35 compares COS-7 cell number remaining in cell culture supernatant after 2 hour cell culture for a surface treated with a representative hydrogel of the invention and polystyrene and tissue culture polystyrene surfaces.

In addition to the capacity to load a bioactive counter ion, another function for CBAA-1 C2 is a polymer backbone to impart a positive charge to the polymer. A cationic hydrogel is expected to favor the adsorption of negatively charged fibronectin, which in turn promotes fibroblast cell surface adhesion, which is crucial for wound healing and tissue regeneration. To verify this hypothesis, a short term cell adhesion experiment was performed with Triblock II hydrogel surface, regular polystyrene surface, and tissue-culture polystyrene surface. Because polystyrene surface is generally considered as not favoring cell adhesion and plasmon treated tissue culture polystyrene does promote cell adhesion, they are used as controls. To prevent background interference, hydrogel solution is added onto non-plasma-treated regular polystyrene surface and allowed to solidify to test its cell adhesion property. To circumvent the problem of hydrogel melting at room temperature, the supernatant was removed from each well while in the 37° C. incubator and the unattached cells were counted to indirectly characterize their surface behavior. FIG. 35 illustrates that cell adhesion for the representative hydrogel surface is comparable to that of tissue culture polystyrene surface, indicating the hydrogel favors fibroblast cell surface adhesion.

The following examples are provided for the purpose of illustrating, not limiting, the claimed invention.

EXAMPLES

Example 1

The Synthesis and Characterization of Representative Cationic Polymers

Materials.

N-(3-dimethylaminopropyl)acrylamide (>98%) was purchased from TCI America, Portland, Oreg. Methyl bromoacetate (97%), ethyl 4-bromobutyrate (≥97.0%), ethyl 6-bromohexanoate (99%), copper (I) bromide (99.999%), bromoisobutyryl bromide (BIBB 98%), 11-mercapto-1-undecanol (97%), and 2,2'-bipyridine (BPY 99%), and 2,2'-azobis(2-methylpropionitrile) (AIBN 98%) were purchased from Sigma-Aldrich. Fibrinogen (fraction I from bovine plasma) and phosphate buffer saline (PBS, pH7.4, 0.15 M, 138 mM NaCl, 2.7 mM KCl) were purchased from Sigma Chemical Co. Ethanol (absolute 200 proof) was purchased from AAPER Alcohol and Chemical Co. Water used in experiments was purified using a Millipore water purification system with a minimum resistivity of 18.0 MΩ.cm.

ω-Mercaptoundecyl bromoisobutyrate (1) was synthesized through reaction of BIBB and 2 using a method described in Ilker, M. F.; Nuesslein, K.; Tew, G. N.; Coughlin, E. B., "Tuning the Hemolytic and Antibacterial Activities of Amphiphilic Polynorbornene Derivatives," *Journal of the American Chemical Society* 126(48):15870-15875, 2004. $^1$H NMR (300 MHz, CDCl$_3$): 4.15 (t, J=6.9, 2H, OCH$_2$), 2.51 (q, J=7.5, 2H, SCH$_2$), 1.92 (s, 6H, CH$_3$), 1.57-1.72 (m, 4H, CH$_2$), and 1.24-1.40 (m, 16H, CH$_2$).

Cationic Monomer Syntheses

CBAA-1-ester: (2-carboxymethyl)-3-acrylamidopropyldimethylammonium bromide, methyl ester.

N-(3-dimethylaminopropyl)acrylamide (25 mmol), methyl bromoacetate (37.5 mmol), and acetonitrile (25 mL) were added into a 100-mL round-bottom flask. The mixture was stirred under a nitrogen atmosphere for 6 hr at room temperature. The precipitate was collected, washed with ca 500 mL of anhydrous acetone. The solvent was removed on a rotary evaporator to get a white powder (96% yield). $^1$H NMR (300 MHz, D$_2$O): 2.02 (m, 2H, —CH$_2$—), 3.25 (s, 6H, N$^+$(CH$_3$)$_2$), 3.37 (t, 2H, CH$_2$—N$^+$), 3.58 (m, 2H, CH$_2$—N), 3.79 (s, 3H, O—CH$_3$), 4.29 (s, 2H, CH$_2$—C=O), 5.77 (m, 1H, CH=C—CON-trans); 6.19 (m, 1H, CH=C—CON—cis), 6.23 (m, 1H, =CH—CON—).

CBAA-3-ester: (4-carboxypropyl)-3-acrylamidopropyldimethylammonium bromide, ethyl ester.

N-(3-dimethylaminopropyl)acrylamide (50 mmol), ethyl 4-bromobutyrate (60 mmol), and acetonitrile (25 mL) were added into a 100-mL round-bottom flask. The mixture was stirred under a nitrogen atmosphere for three days at room temperature. The solvent was removed on a rotary evaporator to get a colorless oil (92% yield). $^1$H NMR (300 MHz, D$_2$O): 1.22 (t, 3H CH$_3$), 2.00 (m, 4H, C—CH$_2$—C), 2.47 (t, 2H, CH$_2$—C=O), 3.06 (s, 6H, N$^+$(CH$_3$)$_2$), 3.28-3.35 (6H, CH$_2$—N and CH$_2$—N$^+$—CH$_2$), 4.14 (q, 2H, O—CH$_2$), 5.75

(m, 1H, CH=C—CON-trans); 6.19 (m, 1H, CH=C—CON— cis), 6.26 (m, 1H, =CH—CON—).

CBAA-5-ester: (6-carboxypentyl)-3-acrylamidopropyldimethylammonium bromide, ethyl ester.

N-(3-dimethylaminopropyl)acrylamide (50 mmol), ethyl 6-bromohexanoate (55 mmol), and acetonitrile (25 mL) were added into a 100-mL round-bottom flask. The mixture was stirred under a nitrogen atmosphere for five days at 45° C. The solvent was removed on a rotary evaporator to get a slightly yellowish oil (87% yield). $^1$H NMR (300 MHz, $D_2O$): 1.20 (t, 3H $CH_3$), 1.34 (m, 2H, C—C—$CH_2$—C—C), 1.60-1.72 (4H, C—$CH_2$—C—$CH_2$—C), 2.00 (m, 2H, N—C—$CH_2$—C—N), 2.34 (t, 2H, $CH_2$—C=O), 3.04 (s, 6H, $N^+(CH_3)_2$), 3.24-3.37 (6H, $CH_2$—N and $CH_2$—$N^+$—$CH_2$), 4.12 (q, 2H, O—$CH_2$), 5.75 (m, 1H, CH=C—CON-trans); 6.20 (m, 1H, CH=C—CON— cis), 6.24 (m, 1H, =CH—CON—).

Representative Cationic Polymer Syntheses

Surface-Initiated ATRP. Three monomers, CBAA-1-ester, CBAA-3-ester, and CBAA-5-ester, were grafted onto gold-coated SPR sensor chips or gold-coated silicon chips using surface-initiated ATRP. The preparation and characterization of the polymer brushes is described in Zhang, Z.; Chen, S.; Chang, Y.; Jiang, S., "Surface Grafted Sulfobetaine Polymers Via Atom Transfer Radical Polymerization as Superlow Fouling Coatings," *Journal of Physical Chemistry B* 110 (22): 10799-10804, 2006, and Zhang, Z.; Chen, S.; Jiang, S., "Dual-Functional Biomimetic Materials: Nonfouling Poly(carboxybetaine) with Active Functional Groups for Protein Immobilization," *Biomacromolecules* 7(12):3311-3315, 2006. previous publications. Briefly, CuBr (1 mmol) and a SPR chip or a gold disk with a Br-thiol SAM was placed in a nitrogen-purged reaction tube. Degassed solution (pure water and methanol in a 1:1 volume ratio, 10 mL) with CBAA ester (6.5 mmol), and BPY (2 mmol, in 5 mL degassed methanol) were transferred to the tube using a syringe. After reaction for more than 1 hour under nitrogen, the SPR chip or gold disk was removed and rinsed with ethanol, water and PBS solution. The samples were stored in PBS solutions before testing.

Polymer Synthesis and Characterization

CBAA-1-ester solution of ca. 0.3 M in methanol was purged with nitrogen for 30 min. The polymerization was then performed at 60° C. for ca 48 hours under nitrogen using 3 mol % AIBN as an initiator to provide polyCBAA-1-ester. Similar methods were applied for preparation of polyCBAA-3-ester or polyCBAA-5-ester using ethanol as a solvent. The polymers were washed with ethyl ether and the solvent was then removed. The structures of the polymers were confirmed by NMR. $^1$H NMR (300 MHz, $D_2O$): polyCBAA-1-ester: 1.62 (br, 2H), 2.05 (br, 3H), 3.25-3.32 (br, 8H), 3.62 (br, 2H), 3.83 (s, 3H), 4.38 (s, 2H); polyCBAA-3-ester 1.21 (t, 3H), 1.61 (br, 2H), 2.04 (br, 5H), 2.50 (t, 2H), 3.37 (br, 6H), 3.12 (s, 6H), 4.14 (q, 2H); polyCBAA-5-ester: 1.22 (t, 3H), 1.37 (m, 2H), 1.62-1.80 (br m, 6H), 2.01 (br, 3H), 2.39 (t, 2H), 3.03 (s, 6H), 3.24 (br m, 6H), 4.12 (q, 2H).

The molecular weight of linear polyCBAA was estimated using a Waters Alliance 2695 Separations Module equipped with a Waters Ultrahydrogel 1000 column and detected with a Waters 2414 Reflex Detector. The mobile phase was an aqueous solution at a flow rate of 0.5 mL/min. The instrument and column were calibrated with poly(ethylene oxide) standards from Polymer Laboratories. All measurements were performed at 35° C. The molecular weight of the polymer was calculated using Empower Pro from Waters.

Example 2

Representative Cationic Polymer Hydrolysis

The cationic polymers prepared as described in Example 1 were dissolved in NaOH solutions with different concentration (10 mM, 100 mM, and 1 M) in a concentration of 50 mg/mL. After an appropriate time interval, the polymer solutions were neutralized with dilute HCl solution and the water was removed by vacuum $^1$H NMR spectroscopy ($D_2O$) was performed to measure the degradation rate by determining the amount of intact ester groups and comparing with other non-hydrolyzable pendant groups as inner standards. The results are illustrated in FIG. 3.

Example 3

Representative Cationic Polymer Protein Adsorption and Release

The cationic polymers prepared as described in Example 1 were evaluated for protein adsorption by surface plasmon resonance (SPR).

Protein adsorption was measured with a custom-built SPR sensor, which is based on wavelength interrogation. A SPR chip was attached to the base of the prism, and optical contact was established using refractive index matching fluid (Cargille). A dual-channel flow cell with two independent parallel flow channels was used to contain liquid sample during experiments. A peristaltic pump (Ismatec) was utilized to deliver liquid sample to the two channels of the flow cell. Fibrinogen solution of 1.0 mg/mL in PBS (0.15M, pH 7.4) was flowed over the surfaces at a flow rate of 0.05 mL/min A surface-sensitive SPR detector was used to monitor protein-surface interactions in real time. Wavelength shift was used to measure the change in surface concentration (mass per unit area). The results are illustrated in FIGS. 5A-5C.

Example 4

Representative Cationic Polymer Antimicrobial Properties

The cationic polymers prepared as described in Example 1 were evaluated for their antimicrobial properties.

Figure 6:
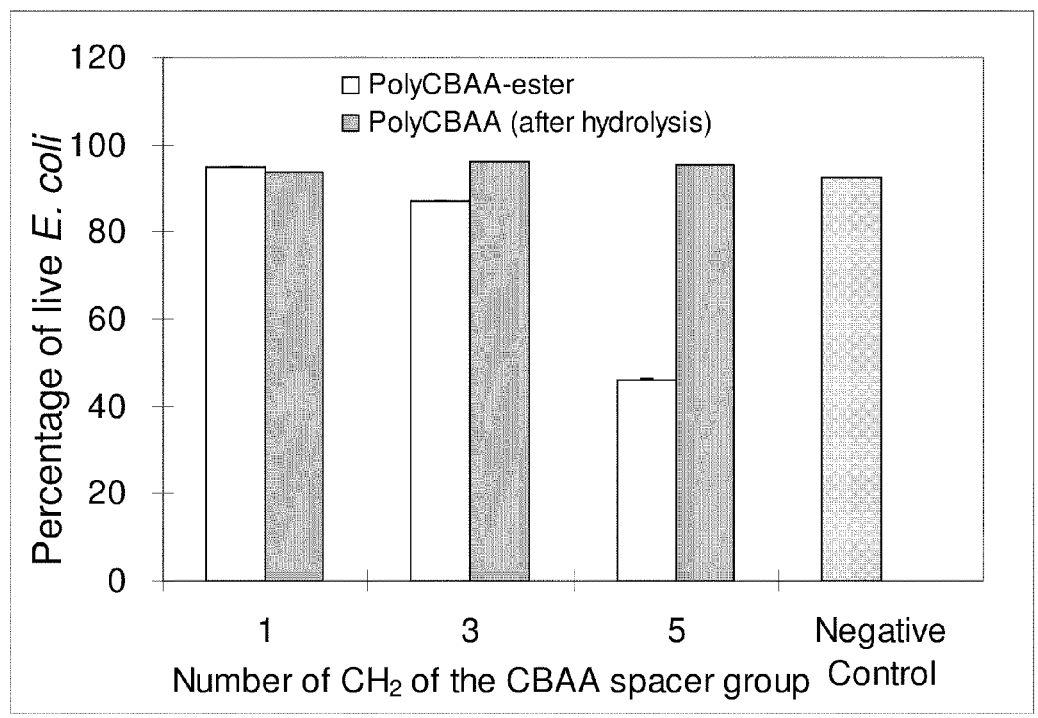
FIG. 6 is a graph comparing antimicrobial activities of three representative cationic polymers of the invention, poly-CBAA-esters, before and after hydrolysis. E. coli (10$^8$ cells/mL) was incubated with each polymer solution (repeat unit molar concentration: 2 mM) for 30 min. PBS buffer (pH 7.4 and 150 mM) is used as a negative control.

*E. coli* K12 were first cultured in separate pure cultures overnight at 37° C. on LB agar plates, which was then incubated with shaking at 37° C. for 24 h. Cultures on agar plates can be used for two weeks, if kept at 4° C. Several colonies were used to inoculate 25 ml of LB (20 g/L). These initial cultures were incubated at 37° C. with shaking at 100 rpm for 18 hours and were then used to inoculate a second culture of each species in 200 ml of appropriate medium. When the second suspended culture reached an optical density of 1.0 at 600 nm, bacteria were collected by centrifugation at 8,000×g for 10 min at 4° C. Cell pellets were washed three times with sterile phosphate buffered saline (PBS, pH7.4) and subsequently suspended in PBS to a final concentration of $10^8$ cells/mL Exposure of bacterial cells to representative polymer solutions was started when the culture containing bacterial cells was added to above polymer suspension which was pre-equilibrated and shaken at 30V, and the mixture were incubated at room temperature for 30 mM. The final solution contains ca. $10^8$ cells/mL *E. coli* and 2 mM repeat unit concentration, which is the molar concentration of the repeat unit of the polymers (ca. 0.6-0.76 mg/mL based on molecular weight of CBAAs and CBAA-esters). Bacteria were stained with Live/Dead BacLight™ (Invitrogen, USA), and bacterial suspension was subsequently filtered through a polycarbonate membrane filter with 0.2 µm pore size (Millipore, USA), and observed directly with a CCD-CoolSNAP camera (Roper scientific, Inc., USA) mounted on Nikon Eclipse 80i with 100× oil lens. The number of live and dead cells was determined, respectively, through FITC and Rhodamine filters with the same microscope described in Cheng, G.; Zhang, Z.; Chen, S.; Bryers, J. D.; Jiang, S., "Inhibition of Bacterial Adhesion and Biofilm Formation on Zwitterionic Surfaces," *Biomaterials* 28(29):4192-4199, 2007. The results are illustrated in FIG. 6.

Example 5

The Preparation, Characterization, and Properties of Representative Cationic Polymer Hydrogel: pCBMA-1-C2 SA In this example, the preparation, characterization, and properties of representative cationic polymer hydrogel (pCBMA-1-C2 SA) is described.

Materials.

2-(Dimethylamino)ethyl methacrylate (DMAEMA), tetraethylene glycol dimethacrylate (TEGDMA), ammonium persulfate (APS), sodium metabisulfite, ethyl bromoacetate, phosphate buffered saline (PBS), sodium salicylate, acetonitrile, ethyl ether, and methanol were purchased from Sigma-Aldrich Chemical Co. (MO, USA). N-cyclohexyl-3-aminopropanesulfonic acid (CAPS) was purchased from TCI America (OR, USA). 2-Carboxy-N,N-dimethyl-N-(2'-(methacryloyloxy)ethyl)ethanaminium inner salt (CBMA-2) was synthesized by the reaction of DMAEMA and β-propiolactone.

N,N-Dimethyl-N-(ethylcarbonylmethyl)-N-[2-(methacryloyloxy)ethyl]ammonium bromide (CBMA-1 C2)

Ethyl bromoacetate (16.6 mL, 150 mmole) was added to a solution of 2-(dimethylamino)ethyl methacrylate (16.9 mL, 99 mmole) in acetonitrile (100 mL), and stirred at 25° C. for 18 hours. The resulting residues were precipitated in ethyl ether, filtered, and subsequently washed twice by ethyl ether. The precipitate was dried in vacuum and analyzed. Yield was 90%. $^1$H NMR (300 MHz, $D_2O$): δ 7.71-7.67 (m, 1H), 7.35-7.28 (m, 1H), 6.86-6.79 (m, 2H), 5.97 (s, 1H), 5.64 (s, 1H), 4.49 (s, 2H), 4.27 (t, 2H, J=3.0 Hz), 4.16-4.09 (t, 2H, J=3.0 Hz), 3.93-3.90 (t, 2H, J=3.0 Hz), 3.24 (s, 6H), 1.78 (s, 3H), 1.17 (t, 3H, J=6.0 Hz).

N,N-Dimethyl-N-(ethylcarbonylmethyl)-N-[2-(methacryloyloxy)ethyl]ammonium salicylate (CBMA-1 C2 SA)

Sodium salicylate (1.64 g, 10 mmole) was dissolved in DI water (10 mL), and the sodium salicylate solution was added to a solution of N,N-dimethyl-N-(ethylcarbonylmethyl)-N-[2-(methacryloyloxy)ethyl]ammonium bromide (3.24 g, 10 mmole) in DI water (10 mL). The reaction was stirred at 25° C. for 24 hours. The product was extracted by chloroform and dried in vacuum and analyzed. $^1$H NMR (300 MHz, $D_2O$): δ 7.0-7.67 (m, 1H), 7.35-7.28 (m, 1H), 6.86-6.79 (m, 2H), 6.11 (s, 1H), 5.65 (s, 1H), 5.03 (s, 2H), 4.66 (t, 2H, J=3.0 Hz), 4.42 (t, 2H, J=3.0 Hz), 4.20 (q, 2H, J=7.2 Hz), 3.76 (s, 6H), 1.92 (s, 3H), 1.29 (t, 3H, J=6.0 Hz).

Chemical Hydrogel Preparation.

1 mmole of CBMA-2 or CBMA-1 C2 SA monomer in a 1 mL mixed solvent of ethylene glycol/ethanol/$H_2O$ (1.5:1:1.5) were mixed with 33 μL TEGDMA, 8 μl 40% ammonium persulfate (APS) and 8 μL 15% sodium metabisulfite (SMS). The reaction was carried out between a pair of glass substrates, separated with a polytetrafluoroethylene (PTFE) spacer with a thickness of 0.76 mm. The reaction mixture was sealed with parafilm and put into a 70° C. oven for 30 min, and left at room temperature for 3 hours. The hydrogels were removed from the glass substrates and soaked in deionized water for 24 hour at 4° C. and water was changed every three hours.

Hydrogel Characterization:

The water content of a hydrogel is a basic property of the hydrogel material for biomedical applications. Wet weight of the hydrogel samples were measured after removal of excess water from the samples. Dry weight was recorded after the samples had been dried at 65° C. under vacuum for 72 hours.

Protein Adsorption on Hydrogels by Enzyme-Linked Immunosorbent Assay.

pCBMA-2 and pCBMA-1 C2 SA hydrogels in water were transferred to PBS buffer and then punched into small disks of 10 mm (10 mm biopsy punch, Acuderm Inc., FL). pCBMA-2 and pCBMA-1 C2 SA hydrogel discs were incubated in CAPS (pH 10.0) at 37 C. After 48 hours, the samples were placed in PBS (pH 7.4) at room temperature for two hours. To measure protein adsorption, samples and tissue culture polystyrene (TCPS) were incubated with horseradish peroxidase (HRP)-conjugated anti-fibrinogen (20 μg/mL buffer) for 0.5 hours at room temperature, followed by 5 washes with PBS. The hydrogels surfaces and TCPS substrates were transferred to individual wells of 24 wells plates. 800 μL of 1 mg/mL o-phenylenediamine in 0.1 M citrate-phosphate pH 5.0 buffer, containing 0.03% hydrogen peroxide, was added. Enzyme activity was stopped by adding an equal volume of 2N $H_2SO_4$ after 15 minutes. The absorbance of the supernatant was measured at 492 nm Bacterial Culture Conditions.

*E. coli* K12 and *S. epidermidis* were cultured in separate pure cultures overnight at 37° C. on Luria-Bertani Medium (LB) (BD, USA) and trypticase soy broth (TSB) (BD, USA) agar plates. Several colonies were used to inoculate 25 mL of LB (20 g/L) for *E. coli* K12 and TSB (20 g/L) for *S. epidermidis*.

Growth Inhibition Assay.

pCBMA-2 and pCBMA-1 C2 SA hydrogels in water were punched into small disks of 10 mm. The overnight cultures of *E. coli* K12 or *S. epidermidis* were washed three times with PBS and diluted in the sterile LB medium with the final concentration of $10^3$ cells/mL 1.0 mL of bacterial suspension was transfer into each well of 24-well plates, and each well contained two test or control hydrogel disks. The bacterial cultures containing hydrogel disks were incubated at 37° C. for 24 hours. After 24 hours, both the concentration of live bacteria in solution and the density of accumulated bacteria on hydrogels were measured. To determine the concentration of live bacteria in solution, bacterial cultures were diluted serially in water and spread on LB agar plates for *E. coli* K12 or TSB agar plates for *S. epidermidis*. After 18 hours at 37° C., the number of colonies on agar plates was recorded to calculate the concentration of live bacterial cells. To analyze the density of bacteria accumulated on hydrogel surfaces, samples were gently rinsed with water, and stained with 1 mL of water containing 20 μM of red fluorescent nucleic acid stain propidium iodide and 3.34 μM green fluorescent nucleic acid stain SYTO9 (Invitrogen, Carlsbad, Calif.). The total number of cells was determined with a CCD-CoolSNAP camera (Roper scientific, Inc., USA) mounted on Nikon Eclipse 80i with 100× oil lens through FITC and Texas Red filters.

Example 6

The Preparation, Characterization, and Properties of a Representative Triblock Copolymer In this example, the preparation, characterization, and properties of a representative triblock copolymer is described.

Materials.

Ethyl bromoacetate 98%, N-[3-(dimethylamino)propyl] acrylamide 99%, salicylic acid sodium salt (NaSA) 99%, dimethylformamide (DMF, HPLC grade) were purchased from ACROS and were used without further purification. N-Isopropylacrylamide 99% (NIPAM) was purchased from Sigma-Aldrich and was recrystallized before use. 2,2'-Azobis (4-methoxy-2.4-dimethyl valeronitrile) (V-70) initiator was purchased from WAKO. Ethanol (absolute 200 proof) was purchased from Decon. Water used in experiments was purified by a millipore purification system.

(N-1-(ethoxycarbonylmethyl)-N-(3-acryloylamino-propyl)-N,N-dimethyl ammonium bromide (CBAA-1-C2 Br) was synthesized by reacting ethyl bromoacetate with N-[3-(dimethylamino)propyl]acrylamide in dry acetonitrile at 60° C., the formed product precipitation was further washed with diethyl ether. Difunctional RAFT chain transfer agent (CTA) 2-(1-carboxy-1-methylethylsulfanylthiocarbonylsulfanyl)-2-methylpropionic acid was synthesized as described in Lai, J. T., D. Filla, and R. Shea, *Functional Polymers from Novel Carboxyl-Terminated Trithiocarbonates as Highly Efficient RAFT Agents*. Macromolecules, 2002. 35(18): p. 6754-6756.

Triblock copolymer NIPAM-co-CBAA-1 C2 SA.

NIPAM macroCTA was synthesized by RAFT as described in Convertine, A. J., et al., *Facile, Controlled, Room-Temperature RAFT Polymerization of N-Isopropylacrylamide*. Biomacromolecules, 2004. 5(4): p. 1177-1180. Briefly, deoxygenated 33 wt % NIPAM monomer was polymerized with CTA and V-70 at 30° C. for 24 h in DMF. CTA amount was changed to get homopolymer with different degree of polymerization (DP), while [CTA]/[I] was kept at 3:1 due to the relatively low reaction temperature. The resulting polymer was purified by dialysis against MiniQ water at 4° C. for 72 h. The purified product was then lyophilized and stored at 4° C. before use. MacroCTA chain extension with CBAA-1-C2 Br was carried out in deoxygenated 0.5 M monomer ethanol solution with macroCTA and V-70. [M]/[CTA] was varied in order to yield different DP while [CTA]/[I] was kept constant at 3:1 for each reaction. Synthesized NIPAM-co-CBAA-1-C2 Br was mixed with 20 volume 0.5 M NaSA in water, ethanol 1:1 mixed solvent. The solution was stirred for 3 h then dialyzed against MiniQ water at 4° C. for 120 h. Water was changed every 12 h. The dialyzed product was lyophilized and stored at 4° C. before use.

Gel Permeation Chromatography.

Gel Permeation Chromatography (GPC) was used to determine $M_n$, $M_w$, and polydispersity indices (PDIs). GPC analysis of PNIPAM homopolymer samples was obtained using a triple detection method (with angular correction) using a Viscotek I-Series Mixed Bed low-MW and mid-MW column running at 60° C. DMF flow rate of 0.5 mL/min, having refractive index, viscometer, and right angle laser light scattering (RALLS) detectors, the wavelength of the laser being 670 nm The DP of the inner block was calculated based on comparison between integration of character peaks from two copolymer blocks in NMR. Unfortunately, triblock copolymer aggregates in DMF and cannot be analyzed using previous method. Alternatively, an aqueous phase GPC system, Waters Alliance 2695 Separations Module equipped with a Waters Ultrahydrogel 1000 column and a Waters 2414 reflex detector, was used to verify the successful extension for macroCTA. The mobile phase 0.5 M $NaNO_3$ running at 25° C. with a flowrate of 0.5 mL/min. The relative high salt concentration was used to help solubilize the positively charged polymer.

Polymer Phase Transition Temperature Measurement.

The phase transition behavior of the polymer was characterized using a dynamic light scattering (DLS) particle sizer (Nano ZS, Zetasizer Nano, Malvern). Triblock copolymer (0.1 wt %) was dissolved in water, and the hydrodynamic radius of the polymer was measured continuously as the temperature being ramped from 20° C. to 50° C.

In vitro SA Release and HPLC Analysis.

Triblock copolymer (10 mL 20 wt %) was heated to 37° C. to form a gel. The hydrogel disk was immediately transferred to 10 mL pre-warmed PBS solution (37° C.) shaking at 40 rpm. 1 mL PBS was removed for HPLC characterization at desired time point and replaced by 1 mL pre-warmed fresh PBS solution.

The amount of salicylate released was monitored using a high performance liquid chromatography system (HPLC) (Waters, Mass.) consisting of a separation module (Model 2695) and a UV/Visible Detector (Model 2489). All separations were performed on an Econosil C18 5µ column (4.6 mm×250 mm) (Alltech, USA) using a mixture of 60% acetonitrile and 40% water. The flow rate of the mobile phase was 0.5 mL/min The elution was monitored at 280 nm. The cumulative fractional release at time t was then calculated based on a freshly prepared calibration curve ($R_2$>0.999).

Bacteria Growth Inhibition.

*E. coli* K12 single colonies were used to inoculate 25 mL of LB (BD, Franklin Lakes, N.J.) (20 g/L) liquid media cultured at 37° C. Exponential phase bacteria was later harvested and diluted with fresh LB to yield $OD_{600}$ about 0.001. Diluted bacteria culture was then added into 24-well plate at the volume of 1 mL/well. Different wells contain 0 or 100 µL hydrogel pre-warmed to 37° C. with different weight concentration and counter ion to be tested for antibacterial activity. After 12 h 37° C. incubation, 100 µL bacteria culture was carefully removed from each well for $OD_{600}$ reading with a spectrophotometer Smartspet™ 3000 (Biorad, USA). Each measurement had three replicate wells.

Mammalian Fibroblast COS-7 Cell Culture and Cytotoxicity Assay.

COS-7 cells (African Green Monkey fibroblast cells, American Tissue Culture Collection; Manassas, Va.) were cultured in Dulbecco's Modified Eagle Medium (Gibco, Invitrogen; Carlsbad, Calif.) supplemented with 10% Fetal BovineSerum, 1× non-essential amino acids, and penicillin streptomycin. Cells were incubated at 37° C. and 5% $CO_2$.

As hydrogels can absorb the chromophore used in a regular MTT assay thereby causing measurement inaccuracy, the MTT protocol was adapted similar to the method described in Makarand V. Risbud, R. R. B., *Polyacrylamide-Chitosan Hydrogels: In Vitro Biocompatibility and Sustained Antibiotic Release Studies*. Drug Delivery, 2000. 7(2): p. 69-75. Briefly, 20 wt % triblock polymer solution was added into 24-well tissue culture plate at 100 µL/well, incubated briefly at 37° C. to solidify. Then 1 mL cell culture media (without phenol red) was added into each well to incubate with hydrogel. Medium from each well was collected after 12 h culture and diluted to give 25%, 50%, and 100% hydrogel leach out to be tested in a standard MTT assay as described in Fotakis, G. and J. A. Timbrell, *In vitro cytotoxicity assays: Comparison of LDH, neutral red, MTT and protein assay in hepatoma cell lines following exposure to cadmium chloride*. Toxicology Letters, 2006. 160(2): p. 171-177. An MTT assay was carried out using a Vybrant MTT cell proliferation assay kit (Invitrogen, Carlsbad, Calif.). 100 µL COS-7 cells were seeded into 96-well tissue culture plate at a density of 10,000 cell/mL for 48 h. At the end of 48 h, regular cell medium was replaced by hydrogel leach out collected previously and incubated for 8 h. Then 100 µL fresh medium (without phenol red) supplemented with 10 µl 1.2 mg/ml MTT was changed to incubate for another 4 h. Finally, cell medium was removed and 50 µL DMSO was added each well to completely dissolve the crystals formed. The absorbance at 570 nm was read with a 96-well plate reader (Spectra Max M5, Molecular Devices, Sunnyvale, Calif.). Cell viability was expressed as the percentage of absorbance of hydrogel leach out treated cells relative to the absorbance of cells that were incubated with regular cell culture medium Each measurement had five replicate wells.

COS-7 Cell Surface Adhesion Assay.

As the thermo-responsive hydrogel dissolves into cell culture medium once at room temperature making directly counting the surface bound cells difficult, an indirect method was used to characterize COS-7 cell adhesion on to various surfaces: 1 mL pre-warmed COS-7 cell culture at the density of 100,000 cell/mL was seeded onto a 24-well plate of (1) tissue culture polystyrene (TCPS), (2) regular polystyrene (PS), and (3) regular polystyrene bottom coated with 100 µL pre-warmed thermo-responsive hydrogel. After 2 h culture, supernatant was carefully removed from each well and unattached cells were counted with Nikon Eclipse TE2000-U microscope. Each measurement had three replicate wells.

While illustrative embodiments have been illustrated and described, it will be appreciated that various changes can be made therein without departing from the spirit and scope of the invention.

The embodiments of the invention in which an exclusive property or privilege is claimed are defined as follows:

1. A polymer, comprising:
   (a) polymer backbone;
   (b) a plurality of cationic centers, each cationic center covalently coupled to the polymer backbone by a first linker;
   (c) a counter ion associated with each cationic center; and
   (d) a hydrolyzable group covalently coupled to each cationic center through a second linker, wherein the hydrolyzable group is hydrolyzable to an anionic center to provide a zwitterionic polymer having the anionic center covalently coupled to the cationic center through the second linker,
   wherein at least a portion of the counter ions are antimicrobial agents, antibacterial agents, or antifungal agents, and/or
   wherein at least a portion of the hydrolyzable groups release an antimicrobial agent, an antibacterial agent, or an antifungal agent.

2. The polymer of claim 1 having the formula:

PB-(L$_1$-N$^+$(R$_a$)(R$_b$)-L$_2$-A(=O)—OR$_c$)$_n$(X$^-$)$_n$ wherein
   PB is the polymer backbone having n pendant groups L$_1$-N$^+$(R$_a$)(R$_b$)-L$_2$-A(=O)—OR$_c$);
   N$^+$ is the cationic center;
   R$_a$ and R$_b$ are independently selected from hydrogen, alkyl, and aryl, or taken together with N$^+$ form a cationic center;
   A(=O)—OR$_c$ is the hydrolyzable group, wherein A is selected from the group consisting of C, S, SO, P, or PO, and R$_c$ is an alkyl, aryl, acyl, or silyl group that may be further substituted with one or more substituents;
   L$_1$ is a linker that covalently couples the cationic center to the polymer backbone;
   L$_2$ is a linker that covalently couples the cationic center to the hydrolyzable group;
   X$^-$ is the counter ion associated with the cationic center; and
   n is an integer from about 10 to about 10,000,
   wherein at least a portion of the counter ions are antimicrobial agents, antibacterial agents, or antifungal agents, and/or
   wherein at least a portion of the hydrolyzable groups release an antimicrobial agent, an antibacterial agent, or an antifungal agent.

3. The polymer of claim 1, wherein at least a portion of the counter ions are selected from the group consisting of antimicrobial agents, antibacterial agents, and antifungal agents.

4. The polymer of claim 1, wherein at least a portion of the counter ions are selected from the group consisting of C1-C20 carboxylates and C1-C20 alkylsulfonates.

5. The polymer of claim 1, wherein at least a portion of the counter ions are selected from the group consisting of nucleic acids, amino acids, proteins, and peptides.

6. The polymer of claim 1, wherein the cationic center is selected from the group consisting of ammonium, imidazolium, triazaolium, pyridinium, morpholinium, oxazolidinium, pyrazinium, pyridazinium, pyrimidinium, piperazinium, and pyrrolidinium.

7. The polymer of claim 2, wherein R$_a$ and R$_b$ are independently selected from the group consisting of C1-C10 straight chain and branched alkyl groups.

8. The polymer of claim 2, wherein L$_1$ is selected from the group consisting of —C(=O)O—(CH$_2$)$_n$— and —C(=O)NH—(CH$_2$)$_n$—, wherein n is an integer from 1 to 20.

9. The polymer of claim 2, wherein L$_2$ is —(CH$_2$)$_n$—, where n is an integer from 1 to 20.

10. The polymer of claim 2, wherein A is selected from the group consisting of C, SO, and PO.

11. The polymer of claim 2, wherein R$_1$ is C1-C20 alkyl.

12. The polymer of claim 2, wherein X$^-$ is selected from the group consisting of halide, carboxylate, alkylsulfonate, sulfate; nitrate, perchlorate, tetrafluoroborate, hexafluorophosphate, trifluoromethylsulfonate, bis(trifluoromethylsulfonyl) amide, lactate, and salicylate.

13. The polymer of claim 1, wherein the polymer is crosslinked.

14. The polymer of claim 1, wherein the polymer is a hydrogel.

15. A polymer having a plurality of repeating units, the repeating units having the formula:

—[CH$_2$—C(R$_d$)]$_n$-L$_1$-N$^+$(R$_a$)(R$_b$)-L$_2$-A(=O)—OR$_c$X$^-$ wherein
   —[CH$_2$—C(R$_d$)]$_n$— defines a polymer backbone having n repeating units;
   R$_d$ is selected from the group consisting of hydrogen, fluorine, trifluoromethyl, and C1-C6 alkyl;
   n is 10 to 10,000;
   N$^+$ is a cationic center;
   R$_a$ and R$_b$ are independently selected from hydrogen, alkyl, and aryl, or taken together with N$^+$ form a cationic center;
   A(=O)—OR$_c$ is a hydrolyzable group, wherein A is selected from the group consisting of C, S, SO, P, or PO, and R$_c$ is an alkyl, aryl, acyl, or silyl group that may be further substituted with one or more substituents;

$L_1$ is a linker that covalently couples the cationic center to the polymer backbone;

$L_2$ is a linker that covalently couples the cationic center to the hydrolyzable group; and $X^-$ is the counter ion associated with the cationic center, wherein at least a portion of the counter ions are antimicrobial agents, antibacterial agents, or antifungal agents, and/or wherein at least a portion of the hydrolyzable groups release an antimicrobial agent, an antibacterial agent, or an antifungal agent.

16. The polymer of claim 15, wherein the polymer is a homopolymer.

17. The polymer of claim 15, wherein the polymer is a copolymer.

18. The polymer of claim 17, wherein the copolymer is a random copolymer.

19. The polymer of claim 17, wherein the copolymer is a block copolymer.

20. The polymer of claim 15, wherein the copolymer comprises a repeating unit selected from the group consisting of a hydrophobic repeating unit, an anionic repeating unit, and a zwitterionic repeating unit.

21. The polymer of claim 15, wherein the polymer is crosslinked.

22. The polymer of claim 15, wherein the polymer is a hydrogel.

23. A surface of a substrate, wherein the surface comprises a polymer of claim 1.

24. The surface of claim 23, wherein the substrate is selected from the group consisting of a particle, a drug carrier, non-viral gene delivery system, a biosensor, a membrane, an implantable sensor, a subcutaneous sensor, an implant, and a contact lens.

25. The surface of claim 23, wherein the substrate is an implantable medical device selected from the group consisting of an ear drainage tube, feeding tube, glaucoma drainage tube, hydrocephalous shunt, keratoprosthesis, nerve guidance tube, urinary catheter, tissue adhesive, x-ray guide, an artificial joint, artificial heart valve, artificial blood vessel, pacemaker, left ventricular assist device (LVAD), artery graft, tissue scaffold, and stent.

* * * * *

UNITED STATES PATENT AND TRADEMARK OFFICE
CERTIFICATE OF CORRECTION

PATENT NO. : 8,658,192 B2
APPLICATION NO. : 12/904341
DATED : February 25, 2014
INVENTOR(S) : S. Jiang et al.

Page 1 of 1

It is certified that error appears in the above-identified patent and that said Letters Patent is hereby corrected as shown below:

In the Claims

| Column | Line | |
|---|---|---|
| 39 (Claim 2) | 58 | In the equation, the portion "$(X_-)_n$" should read --$(X^-)_n$-- |
| 40 (Claim 11) | 40 | "$R_1$" should read --$R_c$-- |

Signed and Sealed this
Twenty-eighth Day of July, 2020

Andrei Iancu
*Director of the United States Patent and Trademark Office*